US006930169B2

(12) United States Patent
Monteiro et al.

(10) Patent No.: US 6,930,169 B2
(45) Date of Patent: Aug. 16, 2005

(54) METHOD OF CONTROLLING THE BINDING OF CALMYRIN TO PRESENILIN

(75) Inventors: Mervyn J. Monteiro, Baltimore, MD (US); Stacy Stabler, Baltimore, MD (US)

(73) Assignee: University of Baltimore Biotechnology Institute, Baltimore, MD (US)

( * ) Notice: Subject to any disclaimer, the term of this patent is extended or adjusted under 35 U.S.C. 154(b) by 20 days.

(21) Appl. No.: 09/878,454

(22) Filed: Jun. 11, 2001

(65) Prior Publication Data

US 2002/0064828 A1 May 30, 2002

Related U.S. Application Data

(60) Provisional application No. 60/210,939, filed on Jun. 12, 2000.

(51) Int. Cl.[7] .............................................. C07K 14/00
(52) U.S. Cl. ....................... 530/350; 530/827; 424/9.1; 514/2
(58) Field of Search ................................ 530/350, 827; 424/9.1; 514/2

(56) References Cited

PUBLICATIONS

Oltvai et al, 1994, Cell: 189–192.*
Drexler et al. Leukemia and Lymphoma, 1993, 9:1–25.*
Embleton et al. Immunol Ser, 1984, 23:181–207.*
Hsu. in: Tissue Culture Methods and Applications, Kruse and Patterson, Eds, 1973, Academic Press, NY, see abstract, p. 764.*
Freshney. Culture of Animal Cells, A Manual of Basic Technique, Alan R. Liss, Inc., 1983, New York, p4.*
Dermer. Bio/Technology, 1994, 12:320.*
Burgess et al. Journal of Cell Biology, 1990, 11:2129–2138.*
Lazar et al. Molecular and Cell Biology, 1988, 8: 1247–1252.*
Tao. et al. The Journal of Immunology, 1989, 143(8): 2595–2601.*
Gillies et al. Human Antibodies and Hybridomas, 1990, 1(1): 47–54.*
Seki N et al, 1988, Saito T et al, 1999, and Naik, MU et al, 1999, Genbank Sequence Database (Accession No: Q9Z0F4), and MPSRCH search report, 2002, us–09–878–454a–2.rsp, pp. 2–3.*
Blacker, D., M.A. Wilcox, N.M. Laird, L. Rodes, S.M. Horvath, R.C. Go, R. Perry, B.J. Watson, 5.5 Bassett, M.G. McInnis, et al. 1998. Alpha–2 macroglobulin is genetically associated with Alzheimer disease. *Nat. Gene.* 19;357–360.
Buscigho, J., H. Harmann, A. Lorenzo, C. Wong, K. Baumarn, B. Sommer, M. Staufenbiel, and B.A. Yanlcner. 1997. Neuronal localization of presenilin–1 and association with amyloid plaques and neurofibrillary tangles in AD. *J Neurosci.* 17:5101–5107.

Capell, A., R. Saffrich, J.C. Olivo, L. Meyn, J. Walter, J. Orunberg, P. Mathews, R. Nixon, C. Dotti, and C. Haass. 1997. Cellular expression and proteolytic processing of presenilin proteins is developmentally regulated during neuronal differentiation. *J Neurochem.* 69:2432–2440.
Caulin, C., G.S. Salvesen, and R.G. Oshima. 1997. Caspase cleavage of keratin 18 and reorganization of intermediate filaments during epithelial cell apoptosis. *J Cell Biol.* 138:1379–1394.
Corder, E.H., A.M. Saunders, W.J. Strittmatter, D.F. Schmechel, P.C. Gaskell, G.W. Small, A.D. Roses, J.L. Haines, and M.A. Pericak–Vance. 1993. Gene dose apolipoprotein E type 4 allele and the risk of AD in late onset families. *Science* 261:921–923.
Deng, G., C.J. Pike, and C.W. Cotman. 1996. Alzheimerassociated presenilin–2 confers increased sensitivity to apoptosis in PC12 cell. *FEBS Letts.* 397:50–54.
Dewji, N.N., C. Do, and S.J. Singer. 1997. On the spurious endoproteolytic processing of the presenilin proteins in cultured cells and tissues. *Proc. Natl Acad Sci.* 94:14031–14036.
Dewji, N.N., and S.J. Singer. 1997. Cell surface expression of the Alzheimer disease–related presenilin proteins. *Proc. Natl. Acad Sci. USA* 94:9926–9931.
Golemis, E., J. Gynris, and R. Brent. 1996. Interaction trap/two–hybrid system to identify interacting proteins. In Current Protocols in Molecular Biology, R. B. F.A. Ausubel, R.E. Kingston, D.D. Moore, J.G. Seidman, J.A. Smith, K, Struhl, ed. (New York: John Wiley & Sons), pp. 20.1.1–20.1.28.
Guo, Q., K. Jurukawa, B.L. Sopher, D.G. Pham, J. Xie, N. Robinson, G.M. Martin, and M.P. Mattson. 1996. Alzheimer's PS–1 mutation perturbs calcium homeostasis and sensitizes PC 12 cells to death induced by amyloid β peptide. *Neuroreport* 8:379–383.
Guo, Q., B.L. Sopher, K. Furukawa, D.G. Pham, N. Robinson, G.M. Martin, and M.P. Mattson. 1997. Alzheimer's presenilin mutation sensitizes neural cells to apoptosis induced by trophic factor withdrawal and amyloid beta–peptide: involvement of calcium and oxyradicals. *J Neurosci.* 17:4212–4222.

(Continued)

*Primary Examiner*—Minh-Tam Davis
(74) *Attorney, Agent, or Firm*—Marianne Fuierer; Steven Hultquist; Yongzhi Yang

(57) ABSTRACT

The present invention describes a calcium-binding myristoylated protein with homology to calcineurin B which interacts preferentially with presenilin 2 protein. Also, the present invention relates to methods that alter protein-protein interaction of the calcium-binding myristoylated protein with presenilin 2 thereby reducing deleterious effects of the protein-protein interaction, such as apoptosis. The present invention further relates to introducing and expressing a mutant presenilin 2 protein or mutant calcium-binding myristoylated protein to modulate cell functions relating to calcium signaling and apoptosis.

6 Claims, 40 Drawing Sheets

OTHER PUBLICATIONS

Guo, Q., N. Robinson, and M. Mattson. 1998. Secreted β–amyloid precursor protein counteracts the proapoptotic action of mutant presenilin–1 by activation of NF–κβ and stabilization of calcium homeostasis.

Guo, Q., S. Christakos, N. Robinson, and M.P. Mattson. 1998. Calbindin D28k blocks the proapoptotic actions fo mutant presenilin 1: reduced oxidative stress and preserved mitochondrial function. *Proc. Natl. Acad Sci. USA* 95:3227–3232.

Haass, C. 1997. Presenilins: Genes for life and death. *Neuron* 18:687–690.

Hardy, J. 1997. Amyloid, the presenilins and Alzheimer's disease. *TINS* 20:155–159.

Janicki, S., and M.J. Monteiro. 1997. Increased apoptosis arising from increased expression of the Alzheimer's disease–associated presenilin–1 mutation (N1411). *J. Cell Biol.* 139:485–495.

Janicki, S., and M.J. Monteior. 1999. Presenilin overexpression arrests cells in the Gi phase of the cell cycle: arrest potentiated by the Alzheimer's disease PS2(N1411) mutant. *Am. J Pathol.* 155, 135–144.

Janicki, S.M., S.M. Staler, and M.J. Monteiro. 2000. Familial Alzheimer's disease presenilin–1 mutants potentiate cell cycle arrest. *Neurobiol Aging.* 21:829–836.

Keller, J.N., Q. Guo, F.W. Holtsberg, A.J. Bruce–Keller, and M.P. Mattson. 1998 Increased sensitivity to mitochondrial toxin–induced apoptosis in neural cells expressing mutant presenilin–1 is linked to perturbed calcium homeostasis and enhanced oxyradical production. *J Neurosci.* 18:4439–4450.

Kim, T.W., W.R. Pettingell, Y.K. Jung, D.M. Kovacs, R.E. Tanzi. 1997. Alternative cleavage of Alzheimer–associated presenilins during apoptosis by a caspase–3 family protease. *Science* 277:373–376.

Kobayashi, M., K. Takamatsu, S. Saitoh, and T. Noguchi. 1993. Myristoylation of hippocalcin is linked to it calcium–dependent membrane association properties. *J. Biol. Chem.* 268(25): 18898–18904.

Kovacs, D.M., H.J. Fausett, K.J. Page, T.W. Kim, W.D. Moir, D.E. Merriam, R.D. Hollister, O.G. Hallmark, R. Mancini, K.M. Felsenstein, et al. 1996. Alzheimer–associated presenilins 1 and 2: neuronal expression in brain and localization to intracellular membranes in mammalian cells. *Nature Med* 2:224–229.

Lee, M.K., Z. Xu, P.C. Wong, and D.W. Cleveland. 1993. Neurofilaments are obligate heteropolymers in vivo. *J. Cell Biol.* 122:1337–1350.

Leissring, M.A., Parker, I. And LaFerla, F.M. 1999. Presenilin–2 mutations modulate amplitude and kinetics of inositol 1, 4,5–trisphosphate–mediated calcium signals. *J Biol. Chem.* 274, 32535–32538.

Li, J., M. Xu, H. Thou, J. Ma, and H. Potter. 1997. Alzheimer presenilins in the nuclear membrane, interphase kinetochores, and centrosomes suggest a role in chromosome segregation. *Cell* 90:917–927.

Loetscher, H., U. Deuschle, M. Broclchaus, D. Reinbardt, P. Nelboeck, J. Mous, J. Grunberg, C. Haass, H. Jacobsen. 1997. Presenilins are processed by caspase–type proteases. *J. Biol. Chem.* 272(33):20655–20659.

Mical, T.I., and M.J. Monteiro. 1998. The role of sequences unique to nuclear intermediate filaments in the targeting and assembly of human lamin B: Evidence for lack of interaction of lamin B with its putative receptor. *J Cell Sci.* 111:3471–3485.

Monteiro, M.J., C. Hicks, L. Gu, and S. Janicki. 1994. Determinants for intracellular sorting of cytoplasmic and nuclear intermediate filaments. *J Cell Biol* 127:1327–1343.

Monteiro, M.J., and T. Mical. 1996. Resolution of Kinase activities during the HeLa cycle: Identification of kinases with cyclic activities. *Exp. Cell Res.* 223:443–451.

Montoya, S.F., C.F. Aston, S.T. DeKosky, M. Ilyas Kamboh, J.S. Lazo, and R.E. Ferrell. 1998 Bleomycin hydrolase is associated with risk of sporadic Alzheimer's disease. *Nature Genet.* 18:211–212.

Naik, U.P., P.M. Patel, and L.V. Parise. 1997. Identification of a novel calcium–binding protein that interacts with the integrin alphaIIb cytoplasmic domain. *J Biol Chem.* 272:4651–4654.

Olshevskaya, E.V., R.E. Hughes, J.B. Hurley, and A.M. Dizhoor. 1997. Calcium–binding, but not a calcium–myristoyl switch, controls the ability of guanylyl cyclase–activating protein GCAP–2 to regulate photoreceptor guanylyl cyclase. *J Biol. Chem.* 272:14327–14333.

Pack–Chung, E., Myers, M.B., Pettingell, W.P., Cheng, I., Moir, R.D., Brownawell, A.M., Tanzi, R.E., and Kim, T.W., 2000. Presenilin 2 interacts with sorcin, a modulator of the ryanodine receptor. *J Biochem.* 275:14440–14445.

H. Payami, G.D. Schellenberg, S.,Zareparsi, J. Kay, G.J. Sexton, M.A., Head, S.S. Matsuyama, L.F. Jarvik, B. Miller, D.Q. McManus, et al., 1997. Evidence for association of HLA–A2 allele with onset age of Alzheimer's disease. *Neurology.* 49:512–518.

Pericak–Vance, M.A., M.P. Bass, L.H. Yammaoka, P.C. Gaskell, W.K. Scott, R.A. Terwedow, M.M. Menold, P.M. Conneally, G.W. Small, J.M. Vance, et al. 1997. Complete genomic screen in late–onset familial Alzheimer disease. Evidence for a new locus on chromosome 12. *JAMA* 278:1237–1241.

Peruz–Tur, J., S. Froelich, G. Prihar, R. Crook, M. Baker, K. Duff, M. Wragg, F. Busfield, C. Lendon. R.F. Clark et al. 1995. A mutation in Alzheimer's disease destroying a splice acceptor site in the presenilin–1 gene. *Neuroreport* 7:297–301.

Reynolds, A., and V. Lundblad. 1989. Yeast vectors and assays for expression of cloned genes in Current Protocols in Molecular Biology, R.B. F.A. Ausubel, R.E. Kingston, D.D. Moore, J.G. Seidman, J.A. Smith, K, Struhi, ed. (New York: John Wiley & Sons), pp. 13.6.1–13.6.4.

Stabler, Stacy M., Identification and Characterization of Calmyrin, a Presenilin 2 Interactor that Modulates Calcium Signaling and Apoptosis. PhD. Dissertation, Apr. 2001.

Smine, A., X. Xu, K. Nishiyama, T. Katada, P. Gambetti, S.P. Yadav, X. Wu, Y.C. Shi, S. Yasuhara, V. Homburger, and T. Okamoto. 1998. Regulation of brain G–protein Go by Alzheimer's disease gene presenilin–1. *J Biol. Chem.* 273:16281–16288.

Thinakaran, G., D.R. Borchelt, M.K. Lee, H.H. Slunt, L. Spitaer, G. Kim, T. Ratovitsky, F. Davenport, C. Nordstedt, M. Seeger, et al. 1996. Endoproteolysis of presenilin 1 and accumulation of processed derivatives in vivo. *Neuron* 17:181–190.

Vito, P., E. Lacana, and L.D. D'Adamio. 1996a. interfering with apoptosis: $Ca^{2+}$–binding protein ALG–2 and Alzheimer's disease gene ALG–3 *Science* 271:521–525.

Vito, P., B. Wolozin, J.K. Ganjei, K. Iwasaki, B. Lacana, and L.D. D'Adamino. 1996b. Requirement of the familial Alzheimer's disease gene P52 for apoptosis. *J Biol Chem.* 271:31025–31028.

Vito, P., et al. 1997. Generation of anti–apoptotic presenilin–2 polypeptides by alternative transcription, proteolysis, and caspase–3 cleavage. *J Biol. Chem.* 272:28315–28320.

Wilcox, C., J.S. Hu, and E.N. Olson. 1987. Acylation of proteins with myristic acid occurs cotranslationally. *Science* 238:1275–1278.

Wolozin, B., P. Alexander, and J. Palacino. 1998. Regulation of apoptosis by presenilin 1. *Neurobiol. Aging* 19:S23–S27.

Wolozin, B., K. Iwasaki, P. Vito, J.K. Ganjei, B. Lacana, T. Sunderland, B. Zhao, J.W. Kusiak, Wasco, W., and L. D'Adamio. 1996. Participation of presenilin 2 in Apoptosis: enhanced basal activity conferred by an AD mutation. *Science* 274:1710–1713.

Woo, R.A. K.G. McLure, S.P. Lees–Miller, D.E. Rancourt, P.W.K. Lee. 1998. DNA–dependent protein kinase acts upstream of p53 in response to DNA damage. *Nature* 394:700–704.

Wu, J.M., Y. Chen, S.M.L. Perruccio, M. Adbel–Ghany, and T.H. Carter. 1993. Phosphorylation of protein tau by double–stranded DNA–dependent protein kinase. *Biochem. Biophys. Res. Commun.* 193(1):13–18.

Ye, Y., and M.E. Fortini. 1998. Characterization of Drosophila Presenilin and its colocalization with Notch during development. *Mech. Dev.* 79:199–211.

Lessring, M.A., B.A. Paul, I.Parker, C.W. Cotman, and F.M. LaFeral. 1999. Alzheimer's presenilin–1 mutation potentiates inositol 1,4,5–triphosphate–mediated calcium signaling in Zenopus oocytes. *J Neurochem.* 72:1061–1068.

* cited by examiner

```
                         MYRISTOYLATION
                             SITE
CALMYRIN          1  MGGSGS RLSKELLAEY Q DLT FLTKQ E LLAHR RF CE L LPQEQRSVESSLR   50
CALCINEURIN       1  MGNEA S ----------YPLE MCS HFDAD EE KRLGK RF KK L DLDNS------   35

CALMYRIN         51  AQ V PF EQ I LSLPELKA NPF KER I CR V FST SPAKDS L SFEDF ID LL SVFSD  100
CALCINEURIN      36  GSL SV EE F MSLPELQQ NPL V QRV IDI LFD T D-GNGEV DFKEF IE GVSQFSV   84
                                                  Ca BINDING EF HAND

CALMYRIN        101  TATPD I KSHYAFR I F D F D DGT L NREDL SRLV NCL TGEGEDTR L SASEMK  150
CALCINEURIN      85  KGDKEQ KL RFAFRTY D MDKD GY I SNGEL F QVL KMM VG------ NN LKDTQLQ  130
                                                  Ca BINDING EF HAND

CALMYRIN        151  QL ID N IL EESD II DR D GT NLSEFQH VI SRSP D FASSFK II V L         191
CALCINEURIN     131  QIVD KT I NADKDG RI SFEE FCAM VG-GLD IHKKMV MDV                   170
```

FIG. 4

PERCENT RESPONDING

PERCENT OSCILLATING

SEQUENCE LISTING

<160> NUMBER OF SEQ ID NOS: 26

<210> SEQ ID NO 1
<211> LENGTH: 448
<212> TYPE: PRT
<213> ORGANISM: Homo sapiens

<400> SEQUENCE: 1

```
Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
            100                 105                 110

Thr Glu Lys Asn Gly Gln Leu Ile Tyr Thr Pro Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190
```

```
Lys Thr Tyr Asn Val Ala Met Asp Tyr Pro Thr Leu Leu Leu Thr Val
            195                 200                 205
Trp Asn Phe Gly Ala Val Gly Met Val Cys Ile His Trp Lys Gly Pro
            210                 215                 220
Leu Val Leu Gln Gln Ala Tyr Leu Ile Met Ile Ser Ala Leu Met Ala
225                 230                 235                 240
Leu Val Phe Ile Lys Tyr Leu Pro Glu Trp Ser Ala Trp Val Ile Leu
            245                 250                 255
Gly Ala Ile Ser Val Tyr Asp Leu Val Ala Val Leu Cys Pro Lys Gly
            260                 265                 270
Pro Leu Arg Met Leu Val Glu Thr Ala Gln Glu Arg Asn Glu Pro Ile
            275                 280                 285
Phe Pro Ala Leu Ile Tyr Ser Ser Ala Met Val Trp Thr Val Gly Met
            290                 295                 300
Ala Lys Leu Asp Pro Ser Ser Gln Gly Ala Leu Gln Leu Pro Tyr Asp
305                 310                 315                 320
Pro Glu Met Glu Glu Asp Ser Tyr Asp Ser Phe Gly Glu Pro Ser Tyr
            325                 330                 335
Pro Glu Val Phe Glu Pro Pro Leu Thr Gly Tyr Pro Gly Glu Glu Leu
            340                 345                 350
Glu Glu Glu Glu Arg Gly Val Lys Leu Gly Leu Gly Asp Phe Ile
            355                 360                 365
Phe Tyr Ser Val Leu Val Gly Lys Ala Ala Thr Gly Ser Gly Asp
370                 375                 380
Trp Asn Thr Thr Leu Ala Cys Phe Val Ala Ile Leu Ile Gly Leu Cys
385                 390                 395                 400
Leu Thr Leu Leu Leu Leu Ala Val Phe Lys Lys Ala Leu Pro Ala Leu
            405                 410                 415
Pro Ile Ser Ile Thr Phe Gly Leu Ile Phe Tyr Phe Ser Thr Asp Asn
            420                 425                 430
Leu Val Arg Pro Phe Met Asp Thr Leu Ala Ser His Gln Leu Tyr Ile
            435                 440                 445

<210> SEQ ID NO 2
<211> LENGTH: 191
<212> TYPE: PRT
<213> ORGANISM: Homo sapiens

<400> SEQUENCE: 2

Met Gly Gly Ser Gly Ser Arg Leu Ser Lys Glu Leu Leu Ala Glu Tyr
1               5                   10                  15
Gln Asp Leu Thr Phe Leu Thr Lys Gln Glu Ile Leu Leu Ala His Arg
            20                  25                  30
Arg Phe Cys Glu Leu Leu Pro Gln Glu Gln Arg Thr Val Glu Ser Ser
            35                  40                  45
Leu Arg Ala Gln Val Pro Phe Glu Gln Ile Leu Ser Leu Pro Glu Leu
        50                  55                  60
Lys Ala Asn Pro Phe Lys Glu Arg Ile Cys Arg Val Phe Ser Thr Ser
65                  70                  75                  80
Pro Ala Lys Asp Ser Leu Ser Phe Glu Asp Phe Leu Asp Leu Leu Ser
            85                  90                  95
Val Phe Ser Asp Thr Ala Thr Pro Asp Ile Lys Ser His Tyr Ala Phe
            100                 105                 110
Arg Ile Phe Asp Phe Asp Asp Asp Gly Thr Leu Asn Arg Glu Asp Leu
```

```
                115                 120                 125

Ser Arg Leu Val Asn Cys Leu Thr Gly Glu Gly Glu Asp Thr Arg Leu
        130                 135                 140

Ser Ala Ser Glu Met Lys Gln Leu Ile Asp Asn Ile Leu Glu Glu Ser
145                 150                 155                 160

Asp Ile Asp Arg Asp Gly Thr Ile Asn Leu Ser Glu Phe Gln His Val
                165                 170                 175

Ile Ser Arg Ser Pro Asp Phe Ala Ser Ser Phe Lys Ile Val Leu
                180                 185                 190

<210> SEQ ID NO 3
<211> LENGTH: 467
<212> TYPE: PRT
<213> ORGANISM: Homo sapiens

<400> SEQUENCE: 3

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
                20                  25                  30

Arg Glu Arg Gln Glu His Asn Asp Arg Arg Ser Leu Gly His Pro Glu
            35                  40                  45

Pro Leu Ser Asn Gly Arg Pro Gln Gly Asn Ser Arg Gln Val Val Glu
        50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Ile Thr Val Ala Leu Leu Ile Trp Asn Phe Gly Val Val
            195                 200                 205

Gly Met Ile Ser Ile His Trp Lys Gly Pro Leu Arg Leu Gln Gln Ala
        210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
        290                 295                 300
```

```
Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
            325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
            405                 410                 415

Gly Leu Cys Leu Thr Leu Leu Leu Ala Ile Phe Lys Lys Ala Leu
            420                 425                 430      Leu

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
    450                 455                 460

Phe Tyr Ile
465

<210> SEQ ID NO 4
<211> LENGTH: 34
<212> TYPE: DNA
<213> ORGANISM: Homo sapiens

<400> SEQUENCE: 4
gctgagtacg ctcgaggtag gggagctgga gggc                              34

<210> SEQ ID NO 5
<211> LENGTH: 31
<212> TYPE: DNA
<213> ORGANISM: Homo sapiens

<400> SEQUENCE: 5
cgcttctgga attccccaaa gggcctctga g                                 31

<210> SEQ ID NO 6
<211> LENGTH: 33
<212> TYPE: DNA
<213> ORGANISM: Homo sapiens

<400> SEQUENCE: 6
gctagcatcg ctcgagccac accatggcag atg                               33

<210> SEQ ID NO 7
<211> LENGTH: 29
<212> TYPE: DNA
<213> ORGANISM: Homo sapiens

<400> SEQUENCE: 7
cgcttctgga attccccacg gttggcatg                                    29

<210> SEQ ID NO 8
<211> LENGTH: 33
<212> TYPE: DNA
<213> ORGANISM: Homo sapiens
```

-continued

```
<400> SEQUENCE: 8
tatcgcttaa gtcgacgatg tagagctgat ggg                              33

<210> SEQ ID NO 9
<211> LENGTH: 28
<212> TYPE: DNA
<213> ORGANISM: Homo sapiens

<400> SEQUENCE: 9
cggtacgtga attcaagaag gcgctgcc                                    28

<210> SEQ ID NO 10
<211> LENGTH: 33
<212> TYPE: DNA
<213> ORGANISM: Homo sapiens

<400> SEQUENCE: 10
gctagcatcg ctcgagatac ttggaatttt tgg                              33

<210> SEQ ID NO 11
<211> LENGTH: 33
<212> TYPE: DNA
<213> ORGANISM: Homo sapiens

<400> SEQUENCE: 11
cgtcatcagc gaattcccga aaggtccact tcg                              33

<210> SEQ ID NO 12
<211> LENGTH: 33
<212> TYPE: DNA
<213> ORGANISM: Homo sapiens

<400> SEQUENCE: 12
ctcgcctagc ctcgagccac accattgttg agg                              33

<210> SEQ ID NO 13
<211> LENGTH: 37
<212> TYPE: DNA
<213> ORGANISM: Homo sapiens

<400> SEQUENCE: 13
tcgtgaggat cctcgagcta ctggagccgc gacaggc                          37

<210> SEQ ID NO 14
<211> LENGTH: 34
<212> TYPE: DNA
<213> ORGANISM: Homo sapiens

<400> SEQUENCE: 14
ctagacctga attcccaatg gcgactgcga cccc                             34

<210> SEQ ID NO 15
<211> LENGTH: 34
<212> TYPE: DNA
<213> ORGANISM: Homo sapiens

<400> SEQUENCE: 15
cgagtagcat gtcgaccagg acaatcttaa agga                             34

<210> SEQ ID NO 16
<211> LENGTH: 33
<212> TYPE: DNA
```

-continued

```
<400> SEQUENCE: 16
gctacactag ccgcgggaat tcggcacgag gcg                                  33

<210> SEQ ID NO 17
<211> LENGTH: 34
<212> TYPE: DNA
<213> ORGANISM: Homo sapiens

<400> SEQUENCE: 17
cgagtagcat gtcgactcac aggacaatct taaa                                 34

<210> SEQ ID NO 18
<211> LENGTH: 74
<212> TYPE: DNA
<213> ORGANISM: Homo sapiens

<400> SEQUENCE: 18
gctacactag ccgcggccac catggagcaa aagctcattt ctgaagagga cttgaatcgc     60
ggcggggcga tggg                                                       74

<210> SEQ ID NO 19
<211> LENGTH: 41
<212> TYPE: DNA
<213> ORGANISM: Homo sapiens

<400> SEQUENCE: 19
gcatgttcat ggatccgcgg ggcgatggcg ggctcgggca g                         41

<210> SEQ ID NO 20
<211> LENGTH: 34
<212> TYPE: DNA
<213> ORGANISM: Homo sapiens

<400> SEQUENCE: 20
cgagtagcat gtcgactcac aggacaatct taaa                                 34

<210> SEQ ID NO 21
<211> LENGTH: 27
<212> TYPE: DNA
<213> ORGANISM: Homo sapiens

<400> SEQUENCE: 21
ccttgaacag agaaaacctg agccggc                                         27

<210> SEQ ID NO 22
<211> LENGTH: 27
<212> TYPE: DNA
<213> ORGANISM: Homo sapiens

<400> SEQUENCE: 22
gccggctcag gttttctctg ttcaagg                                         27

<210> SEQ ID NO 23
<211> LENGTH: 27
<212> TYPE: DNA
<213> ORGANISM: Homo sapiens

<400> SEQUENCE: 23
ccatcaacct ctctcagttc cagcacg                                         27

<210> SEQ ID NO 24
```

```
<211> LENGTH: 27
<212> TYPE: DNA
<213> ORGANISM: Homo sapiens

<400> SEQUENCE: 24
cgtgctggaa ctgagagagg ttgatgg                                           27

<210> SEQ ID NO 25
<211> LENGTH: 2285
<212> TYPE: DNA
<213> ORGANISM: Homo sapiens
<220> FEATURE:
<221> NAME/KEY: misc_feature
<222> LOCATION: (2137)..(2137)
<223> OTHER INFORMATION: n can be a, c, t or g
<221> NAME/KEY: misc_feature
<222> LOCATION: (2144)..(2144)
<223> OTHER INFORMATION: n can be a, c, t or g
<221> NAME/KEY: misc_feature
<222> LOCATION: (2152)..(2152)
<223> OTHER INFORMATION: n can be a, c, t or g
<221> NAME/KEY: misc_feature
<222> LOCATION: (2157)..(2157)
<223> OTHER INFORMATION: n can be a, c, t or g
<221> NAME/KEY: misc_feature
<222> LOCATION: (2160)..(2160)
<223> OTHER INFORMATION: n can be a, c, t or g
<221> NAME/KEY: misc_feature
<222> LOCATION: (2163)..(2163)
<223> OTHER INFORMATION: n can be a, c, t or g
<221> NAME/KEY: misc_feature
<222> LOCATION: (2180)..(2180)
<223> OTHER INFORMATION: n can be a, c, t or g
<221> NAME/KEY: misc_feature
<222> LOCATION: (2203)..(2203)
<223> OTHER INFORMATION: n can be a, c, t or g
<221> NAME/KEY: misc_feature
<222> LOCATION: (2213)..(2213)
<223> OTHER INFORMATION: n can be a, c, t or g
<221> NAME/KEY: misc_feature
<222> LOCATION: (2216)..(2216)
<223> OTHER INFORMATION: n can be a, c, t or g
<221> NAME/KEY: misc_feature
<222> LOCATION: (2225)..(2225)
<223> OTHER INFORMATION: n can be a, c, t or g

<400> SEQUENCE: 25
gaattcggca cgagggcatt tccagcagtg aggagacagc cagaagcaag cttttggagc        60
tgaaggaacc tgagacagaa gctagtcccc cctctgaatt ttactgatga agaaactgag       120
gccacagagc taaagtgact tttcccaagg tcgcccagcg aggacgtggg acttctcaga       180
cgtcaggaga gtgatgtgag ggagctgtgt gaccatagaa agtgacgtgt taaaaaccag       240
cgctgccctc tttgaaagcc agggagcatc attcatttag cctgctgaga agaagaaacc       300
aagtgtccgg gattcaagac ctctctgcgg ccccaagtgt tcgtggtgct tccagaggca       360
gggctatgct cacattcatg gcctctgaca gcgaggaaga agtgtgtgat gagcggacgt       420
ccctaatgtc ggccgagagc cccacgccgc gctcctgcca ggagggcagg cagggcccag       480
aggatggaga gaatactgcc cagtggagaa gccaggagaa cgaggaggac ggtgaggagg       540
accctgaccg ctatgtctgt agtggggttc ccggcggcc gccaggcctg gaggaagagc       600
tgaccctcaa atacggagcg aagcatgtga tcatgctgtt tgtgcctgtc actctgtgca       660
tgatcgtggt ggtagccacc atcaagtctg tgcgcttcta cacagagaag aatggacagc       720
tcatctacac gccattcact gaggacacac cctcggtggg ccagcgcctc ctcaactccg       780
tgctgaacac cctcatcatg atcagcgtca tcgtggttat gaccatcttc ttggtggtgc       840
tctacaagta ccgctgctac aagttcatcc atggctggtt gatcatgtct tcactgatgc       900
```

```
tgctgttcct cttcacctat atctaccttg gggaagtgct caagacctac aatgtggcca      960
tggactaccc caccctcttg ctgactgtct ggaacttcgg ggcagtgggc atggtgtgca     1020
tccactggaa gggccctctg gtgctgcagc aggcctacct catcatgatc agtgcgctca     1080
tggccctagt gttcatcaag tacctcccag agtggtccgc gtgggtcatc ctgggcgcca     1140
tctctgtgta tgatctcgtg gctgtgctgt gtcccaaagg gcctctgaga atgctggtag     1200
aaactgccca ggagagaaat gagcccatat tccctgccct gatatactca tctgccatgg     1260
tgtggacggt tggcatggcg aagctggacc cctcctctca gggtgccctc cagctcccct     1320
acgacccgga gatggaagaa gactcctatg acagttttgg ggagccttca taccccgaag     1380
tctttgagcc tcccttgact ggctacccag gggaggagct ggaggaagag gaggaaaggg     1440
gcgtgaagct tggcctcggg gacttcatct tctacagtgt gctggtgggc aaggcggctg     1500
ccacgggcag cggggactgg aataccacgc tggcctgctt cgtggccatc ctcattggct     1560
tgtgtctgac cctcctgctg cttgctgtgt tcaagaaggc gctgcccgcc ctccccatct     1620
ccatcacgtt cgggctcatc ttttacttct ccacggacaa cctggtgcgg ccgttcatgg     1680
acaccctggc ctcccatcag ctctacatct gagggacatg gtgtgccaca ggctgcaagc     1740
tgcagggaat tttcattgga tgcagttgta tagtttttaca ctctagtgcc atatatttt      1800
aagactttc tttccttaaa aaataaagta cgtgtttact tggtgaggag gaggcagaac     1860
cagctctttg gtgccagctg tttcatcacc agactttggc tcccgctttg gggagcgcct     1920
cgcttcacgg acaggaagca cagcaggttt atccagatga actgagaagg tcagattagg     1980
gtggggagaa gagcatccgg catgagggct gagatgccca agagtgtgc tcgggagtgg     2040
cccctggcac ctgggtgctc tggctggaga ggaaaagcca gttccctacg aggagtgttc     2100
ccaatgcttt gtccatgatg tccttgttat tttattnccy ttanaaactg antcctnttn     2160
ttnttdcggc agtcacmctn ctgggragtg gcttaatagt aanatcaata aanagntgag     2220
tcctnttaga aaaaaaaaa aaaaaaaaa aaaaaaaaa aaaaaaaaa aaaaaaaaa           2280
aaaaa                                                                 2285

<210> SEQ ID NO 26
<211> LENGTH: 885
<212> TYPE: DNA
<213> ORGANISM: Homo sapiens

<400> SEQUENCE: 26
tctcccgaat tcggcacgag gcggcgtctc gaggcgagtt ggcggagctg tgcgcgcggc       60
ggggcgatgg ggggctcggg cagtcgcctg tccaaggagc tgctggccga gtaccaggac      120
ttgacgttcc tgacgaagca ggagatcctc ctagcccaca gccggttttg tgagctgctt      180
ccccaggagc agcggaccgt ggagtcgtca cttcgggcac aagtgccctt cgagcagatt      240
ctcagccttc cagagctcaa ggccaacccc ttcaaggagc gaatctgcag ggtcttctcc      300
acatccccag ccaaagacag ccttagcttt gaggacttcc tggatctcct cagtgtgttc      360
agtgacacag ccacgccaga catcaagtcc cattatgcct tccgcatctt tgactttgat      420
gatgacggaa ccttgaacag agaagacctg agccggctgg tgaactgcct cacgggagag      480
ggcgaggaca cacggcttag tgcgtctgag atgaagcagc tcatcgacaa catcctggag      540
gagtctgaca ttgacaggga tggaaccatc aacctctctg agttccagca cgtcatctcc      600
cgttctccag actttgccag ctccttttaag attgtcctgt gacagcagcc ccagcgtgtg      660
```

-continued

| | | | | | |
|---|---|---|---|---|---|
| tcctggcacc | ctgtccaaga | acctttctac | tgctgagctg | tggccaaggt | caagcctgtg | 720
| ttgccagtgc | gggccaagct | ggcccagcct | ggagctggcg | ctgtgcagcc | tcaccccggg | 780
| cagggcggc | cctcgttgtc | agggcctctc | ctcactgctg | ttgtcattgc | tccgtttgtg | 840
| tttgtactaa | tcagtaataa | aggtttagaa | gtttgaccct | aaaaa | | 885

METHOD OF CONTROLLING THE BINDING OF CALMYRIN TO PRESENILIN

CROSS REFERENCE TO RELATED APPLICATIONS

This application claims the benefit from U.S. Provisional Application Ser. No. 60/210,939, filed Jun. 12, 2000. +gi

GOVERNMENT RIGHTS IN INVENTION

Some aspects of the invention disclosed in this application were supported by the United States government, National Institute of Health Grant No. AG 11386. Accordingly, the U.S. Government has certain rights in the invention hereof.

BACKGROUND OF THE INVENTION

1. Field of the Invention

The present invention generally relates to protein-protein interaction, and more particularly, reducing protein-protein interaction between presenilin 2 and a calcium-binding protein to modulate apoptosis and calcium signaling.

2. Background of the Related Art

Alzheimer's disease (AD) is a degenerative disorder characterized clinically by progressive dementia and neuropathologically by the presence of senile plaques and neurofibrillary tangles (NFT). Genetic studies indicate the etiology of AD to be heterogeneous. It is well established that mutation in the genes including, presenilin 1(PS1), and presenilin 2(PS2) genes, cause the majority of early onset of familial Alzheimer's disease (FAD) (i.e., FAD before 65 years of age). Many other genes, including some that act as modifiers or risk factors, appear to be associated with late-onset AD (>65 yr; Corder et al., 1993; Payami et al., 1997; Pericak-Vance et al., 1997; Blacker et al., 1998; Montoya et al., 1998).

Approximately 50% of all FAD cases are linked to the presenilin genes where missense mutations are generally found in residues that are conserved between the two proteins with the rare exceptions of in-frame splice deletions and premature truncations. The mechanisms by which mutations in PS1 and PS2 cause AD are not known, although mutations in these genes appear somehow interconnected as they increase amyloidogenic Aβ fragment accumulation (reviewed by Hardy, 1997).

Human PS1 and PS2 genes are both ubiquitously expressed, but at low protein levels which have lead to difficulties and inconsistencies in their detection and localization. Upon overexpression, the presenilins have been localized to the endoplasmic reticulum (ER) and nuclear envelope (see Kovacs et al., 1996; Janicki and Monteiro, 1997 and references therein) with one group reporting evidence also for cell surface localization (Dewji and Singer, 1997). Endogenous PS1 and PS2 proteins, in turn, have been localized to a variety of structures, including the ER, vesicular structures of the somatodentritic compartment, within axons, at centrosomes and centromeres, and at the plasma membrane (Busciglio et al., 1997; Capell et al., 1997; Li et al., 1997; Ye and Fortini, 1998).

Human PS1 and PS2 proteins are 67% identical, sharing highest similarity in their COOH-terminal sequence and in multiple hydrophobic internal regions that are structurally predicted to form transmembrane domains (TMD). Assuming the presenilins are transmembrane proteins, their topography according to most models is of a protein that weaves through membranes eight times with the $NH_2$— and COOH-terminal domains and the large "loop" spanning the putative sixth and seventh TMD all facing the cytoplasm (see FIG. 1; Hardy, 1997).

Interestingly, presenilins have been implicated in the regulation of programmed cell death (apoptosis). Evidence for such a role was first shown when a cDNA fragment encoding the 103 COOH-terminal amino acids of mouse PS2, termed ALG-3, was isolated in a screen for cDNAs that could rescue T cells from receptor-induced apoptosis (Vito et al., 1996a). This rescue appears to be a consequence of the ALG-3 fragment acting in a dominant negative fashion, since expression of full-length PS2 leads to apoptosis (Vito et al., 1996b). Compared with the apoptosis induced by the overexpression of wild-type PS2 in PC12 and HeLa cells, the FAD PS2-(N141I) mutation causes even higher levels of apoptosis (Deng et al., 1996; Wolozin et al., 1996; Janicki and Monteiro, 1997). Likewise, PS1 overexpression also sensitizes cells to apoptosis (Guo et al., 1996, 1997; Wolozin et al., 1998).

The mechanisms by which presenilins induce apoptosis are not fully understood, but perturbations in calcium $Ca^{2+}$, oxidative stress (Guo et al., 1996; Keller et al., 1998), destabilization of β-catenin (Zhang et al., 1998), increased signaling by heterotrimeric GTP-binding proteins have been implicated (Wolozin et al., 1996; Smine et al., 1998) and G1 cell cycle arrest (Janicki and Monteiro, 1999; Janicki et al. 2000) have all been implicated.

It seems clear that expressed proteins of the presenilins are somehow built into the apoptotic machinery evidenced by several apoptotic characteristics e.g., cell shrinkage, increased DNA fragmentation, increased Bax expression and caspase activation that have been identified in postmortem brains of AD patients. Thus, it would be advantages to identify binding partners of the expressed presenilin proteins thereby linking these proteins to known pathways or structures and modulate the activity of the normal and mutant binding partners.

SUMMARY OF THE INVENTION

The present invention relates to identifying a calcium-binding myristoylated protein with homology to calcineurin B (hereinafter referred to as Calmyrin) that interacts with and/or binds to presenilin 2 to modulate apoptosis and calcium signaling.

This invention also relates to identifying a modulator of apoptosis to ameliorate the effects of Alzheimer's disease.

This invention further provides for a purified and isolated nucleic acid molecule encoding a mutated calcium-binding myristoylated protein with homology to calcineurin depicted in SEQ ID NO: 2.

This invention further relates to production of antibodies, including polyclonal and monoclonal, capable of binding to normal and/or mutant presenilin 2 and calmyrin.

In a first aspect, the invention provides for a method to reduce apoptosis mediated by protein-protein interaction, the method comprising:
  inhibiting protein-protein interaction of presenilin 2 protein comprising the amino acid sequence depicted in SEQ ID NO: 1 with a calcium-binding myristoylated protein having an homology to calcineurin B comprising the amino acid sequence depicted in SEQ ID NO: 2.

In another aspect, the invention provides for a calcium-binding myristoylated protein that exhibits a reduced protein-protein interaction with presenilin 1 having the amino acid sequence depicted in SEQ ID NO: 3 relative to an exhibited protein-protein interaction with presenilin 2.

In still another aspect, the invention provides for therapies to treat related presenilin associated diseases such as AD including: gene therapy based on administration of mutant calmyrin and/or PS2 genes that encode for proteins that exhibit reduced interaction with normal calmyrin and/or normal PS2; gene therapy based upon sequences that encode proteins that block the deleterious effects of normal or mutant PS2 genes; and immunotherapy based upon antibodies to reactive sites of presenilin 2 and normal and/or mutant calmyrin.

In another aspect, the present invention relates to disrupting specific presenilin 2 interactions with a calcium-binding protein by increasing cellular amounts of presenilin 2 protein having the amino acid sequence depicted in SEQ ID NO: 1 having at least one substitution of an amino acid residue at a biologically active loop of the PS2 wherein the amino acid substitution site may be selected from the site consisting of 287, 288 and 297.

In a further aspect, the invention provides for reducing protein-protein interaction between presenilin 2 and a calcium-binding protein comprising the amino acid residues of SEQ ID NO: 2 wherein the calcium binding protein is mutated with at least one substitution of an amino acid residue positioned in the calcium-binding EF-hands of SEQ ID NO: 2. Preferably, at least one acidic amino acid residue in the calcium-binding EF-hands of the calcium binding protein is substituted with its amine counterpart. Additionally, it has been discovered that a substitution at the penultimate N-terminal residue of the calcium-binding protein that comprises the amino acid residues of SEQ ID NO: 2 modulates interaction between presenilin 2 and the calcium-binding protein with a concomitant reduction of apoptosis. Preferably, the N-terminal glycine is substituted by alanine.

In yet another aspect, the invention relates to an isolated and purified nucleic acid molecule encoding the amino acid sequence of SEQ ID NO: 2 having at least one substitution in the calcium-binding EF-hands of the calcium binding protein and/or the penultimate N-terminal residue of the calcium-binding protein. The isolated and purified nucleic acid molecule may be incorporated into an expression vector for introduction into a host cell including, a bacterial cell, insect cell, plant cell, animal cell or human cell.

In a still further aspect, the invention relates to a method of reducing apoptosis in neuronal cells comprising:

administering an antisera specific for a calcium-binding myristoylated protein having an homology to calcineurin comprising substantially the amino acid sequence depicted in SEQ ID NO: 2 in a sufficient amount to effect protein-protein interaction with presenilin 2 having substantially the amino acid sequence depicted in SEQ ID NO: 1

In another aspect, the invention relates to a vector for transforming a mammalian tissue cell to express therapeutically effective amounts of a mutant calcium-binding protein comprising the amino acid residues of SEQ ID NO: 2 wherein at least one acidic amino acid residue in the calcium-binding EF-hands of the calcium binding protein is substituted with its amine counterpart and/or at least one substitution at the penultimate N-terminal residue of the calcium-binding protein. The vector may be delivered to the cells by a suitable vehicle, including but not limited to vaccinia virus, adeno associated virus, retrovirus, liposome transport, neuraltropic viruses and other vector systems.

Other features and advantages of the invention will be apparent from the following detailed description, drawings and claims.

BRIEF DESCRIPTION OF THE FIGURES

FIG. 4 shows the amino acid sequence of calmyrin in comparison to human calcineurin B.

DETAILED DESCRIPTION OF PREFERRED EMBODIMENTS

Figure 1:
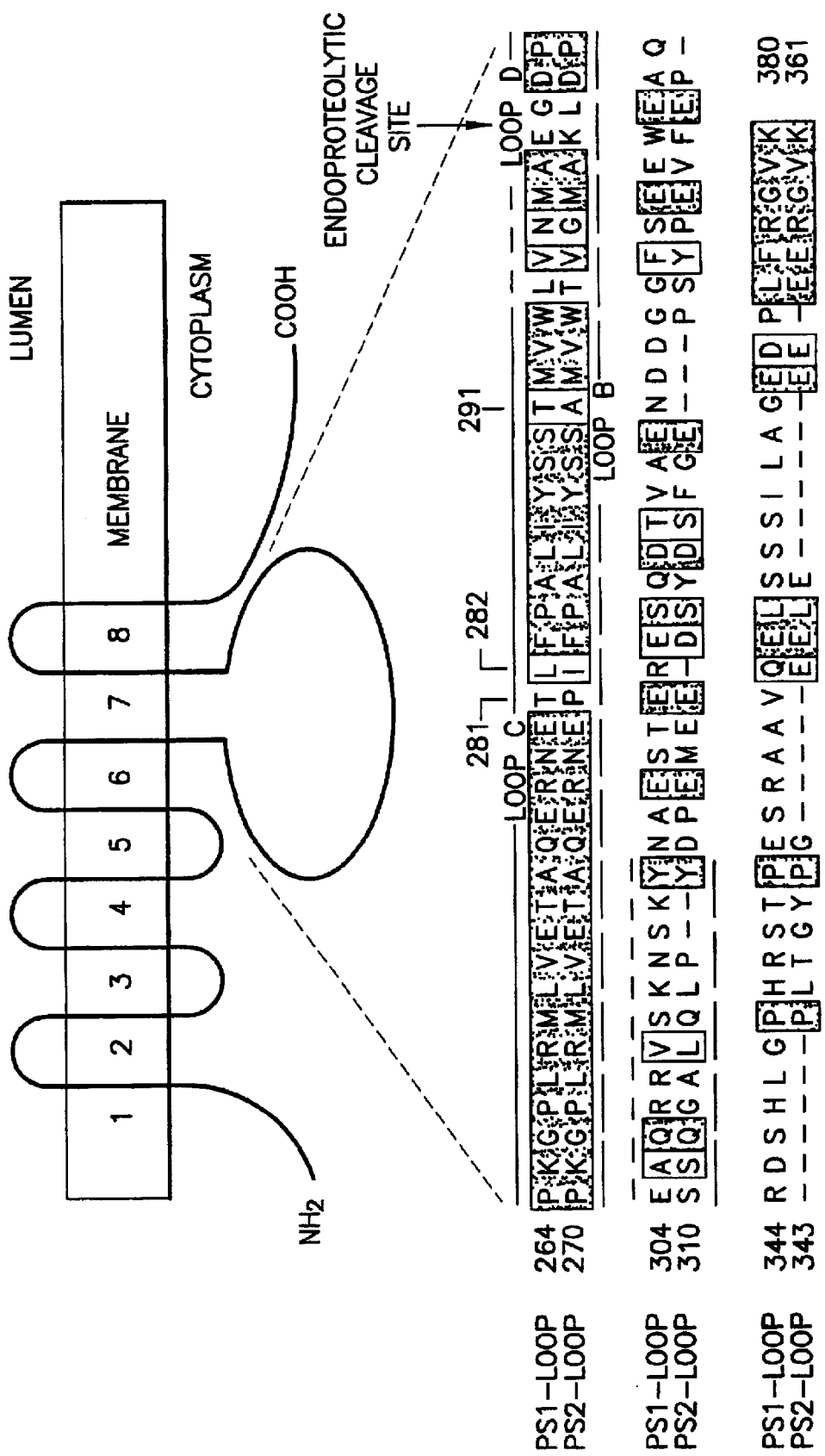
FIG. 1 shows the presenilin 1 and 2 loop construct (SEQ ID NO: 27 and 28, respectively).

In order to facilitate review of the various embodiments of the invention and provide an understanding of the various elements and constituents used in making and using the present invention, the following terms used in the invention description have the following meanings.

All publications mentioned herein are incorporated herein by reference for the all purposes.

Definitions

The term "nucleic acid sequence" as used herein refers to an oligonucleotide, nucleotide, or polynucleotide, and fragments or portions thereof, and to DNA, cDNA or RNA of genomic or synthetic origin which may be single- or double-stranded, and represent the sense or antisense strand.

The term "amino acid sequence" as used herein refers to an oligopeptide, peptide, polypeptide, or protein sequence, and fragments or portions thereof, and to naturally occurring or synthetic molecules.

The term "mutant", as used herein, refers to an amino acid sequence that is altered by one or more amino acids. The mutant may have "conservative" changes, wherein a substituted amino acid has similar structural or chemical properties, e.g., replacement of leucine with isoleucine or a variant may have "nonconservative" changes, e.g., replacement of a glycine with a tryptophan. Similar minor variations may also include amino acid deletions or insertions, or both. Guidance in determining which amino acid residues may be substituted, inserted, or deleted to maintain or abolishing biological or immunological activity may be found using computer programs well known in the art, for example, DNASTAR software.

The term "substitution", as used herein, refers to the replacement of one or more amino acids or nucleotides by different amino acids or nucleotides, respectively.

The term "immunologically active" refers to the capability of the natural, recombinant, or synthetic protein, or any oligopeptide thereof, to induce a specific immune response in appropriate animals or cells and to bind with specific antibodies.

The term "inhibitor", as used herein, refer to a molecule which, when bound to proteins, blocks or modulates the biological or immunological activity of the protein.

The term "modulate", as used herein, refers to a change or an alteration in the biological activity.

The term "biologically active", as used herein, refers to a protein having structural, regulatory, or biochemical functions of a naturally occurring molecule.

The term "homology", as used herein, refers to a degree of complementarity. There may be partial homology or complete homology.

The term "antisense", as used herein, refers to nucleotide sequences which are complementary to a specific DNA or RNA sequence. The term "antisense strand" is used in reference to a nucleic acid strand that is complementary to the "sense" strand.

The term "specific binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general.

As used herein, the term "antibody", refers to intact molecules as well as fragments thereof, such as Fa, $F(ab')_2$, and Fv, which are capable of binding the epitopic determinant.

The term "transformed cell", is a cell into which has been introduced, by means of recombinant DNA technique, a DNA molecule encoding a protein of interest.

The term "transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "substantially identical amino acid sequence" means an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). A "substantially identical nucleic acid sequence "codes for a substantially identical amino acid sequence as defined above.

The Invention:

The present invention is based on the discovery of a calcium-binding myristoylated protein with homology to calcineurin B which interacts preferentially with presenilin 2 proteins to induce apoptosis. Specifically, it has been discovered that mutation of the amino acid sequence of calcium-binding protein can reduce interaction with presenilin 2 thereby reducing apoptosis and/or calcium signaling.

Accordingly, the present invention provides for identifying substances that affect the interaction of PS2 with calmyrin. The present invention also provides for a vector system comprising a vector that expresses a mutant presenilin 2 protein or mutant calmyrin protein in a suitable host cell, such as prokaryotic and eukaryotic cells, e.g. bacterial cells, yeast cells, insect cells and animal cells, to effect protein-protein interaction. This invention also provides for production of antibodies, either polyclonal or monoclonal, capable of binding to wild-type or mutant calmyrin to reduce interaction of the calmyrin with PS2.

Experimental Procedures

1. Primer List region from human PS2 (Janicki and Monteiro, 1997) using primers B5' and B3'. The resulting 150-bp PCR fragment was double digested with EcoRI and XhoI and ligated into the corresponding sites of the pEG202 LexA fusion plasmid. This bait construct and the LacZ reporter plasmid pSH18-34 were cotransformed into yeast strain EGY48 which was then transformed with ~5 µg of human fetal brain cDNA library in pJG4-5. $1.5 \times 10^7$ of the resulting transformants were plated on Gal/Raf/CM-ura-his-trp-leu plates to screen for transcriptional activation of the chromosomally integrated LEU2 reporter gene. 100 Leu+ yeast colonies were picked to a Glu/CM-ura-his-trp master plate, then replica-plated to Glu/CM-ura-his-trp-leu, Gal/Raf/CM-ura-his-trp-leu, Glu/Xgal/CM-ura-his-trp and Gal/Raf/Xgal/CM-ura-his-trp plates to test for galactose-dependent leu2 and lacZ expression. Dual expression of the reporters was displayed by 15 colonies, from which the library plasmids were recovered in *Escherichia coli* strain JBe15 and subsequently transformed back into EGY48 containing pSH18-34 and the pEG202LexA/PS2-loop B bait or one of several negative controls to test the specificity of the interaction with PS2-loop B. The library plasmids that produced a strong and specific interaction with PS2-loop B were recovered in *E. coli* strain DH1 and the DNA sequence of their inserts was determined.

DNA and protein sequences were analyzed using MacVector 6.5(Oxford Molecular). Homology searches of the NCBI databases were performed using the BLAST program. Three of seven putative interactors were independent clonings of the same cDNA which we named calmyrin.

```
B3': 5'GCTGAGTACGCTCGAGGTAGGGGAGCTGGAGGGC3';          SEQ ID NO:4

B5': 5'CGCTTCTGGAATTCCCCAAAGGGCCTCTGAG3';             SEQ ID NO:5

C3': 5'GCTAGCATCGCTCGAGCCACACCATGGCAGATG3';           SEQ ID NO:6

D5': 5'CGCTTCTGGAATTCCCCACGGTTGGCATG3';               SEQ ID NO:7

E3': 5'TATCGCTTAAGTCGACGATGTAGAGCTGATGGG3';           SEQ ID NO:8

E5': 5'CGGTACGTGAATTCAAGAAGGCGCTGCC3';                SEQ ID NO:9

F3': 5'GCTAGCATCGCTCGAGATACTTGGAATTTTTGG3';           SEQ ID NO:10

F5': 5'CGTCATCAGCGAATTCCCGAAAGGTCCACTTCG3';           SEQ ID NO:11

G3': 5'CTCGCCTAGCCTCGAGCCACACCATTGTTGAGG3';           SEQ ID NO:12

L3': 5'TCGTGAGGATCCTCGAGCTACTGGAGCCGCGACAGGC3';       SEQ ID NO:13

L5': 5'CTAGACCTGAATTCCCAATGGCGACTGCGACCCC3';          SEQ ID NO:14

M3': 5'CGAGTAGCATGTCGACCAGGACAATCTTAAAGGA3';          SEQ ID NO:15

M5': 5'GCTACACTAGCCGCGGGAATTCGGCACGAGGCG3';           SEQ ID NO:16

N3': 5'CGAGTAGCATGTCGACTCACAGGACAATCTTAAA3';          SEQ ID NO:17

N5': 5'GCTACACTAGCCGCGGCCACCATGGAGCAAAAGC
TCATTTCTGAAGAGGAC TT GAAT CGCGGCGGGGCGATGGG3'.        SEQ ID NO: 18
```

Restriction enzymes sites incorporated into the primers to aid in cloning are underlined.

2. Yeast Two-Hybrid Library Screening

The yeast two-hybrid screen for PS2 interacting proteins was performed essentially as described by Golemis et al. (1996), with the necessary plasmids and cDNA library obtained from Dr. Roger Brent (Harvard Medical School, Cambridge, Mass.). The PS2-loop bait (designated PS2-loop B, see FIG. 1A) was constructed by PCR amplification of the For further experiments, clone 7, a library plasmid which contained full-length calmyrin cDNA was digested with EcoRI and XhoI and subcloned into pBluescript KS(−) or pGST/His T1 vector. (Pharmacia-Biotech, Inc.).

3. Yeast Two-Hybrid Liquid Assay

The specificity of the calmyrin interaction was tested against three PS2-loop region constructs, two different PS1-loop constructs of which one was further mutated to the corresponding PS2 sequence, one PS2 COOH-terminal construct, and a lamin control. A conserved 31-amino acid loop region (designated PS2-loop C) was obtained by using primers B5' (SEQ ID NO: 5) and C3' (SEQ ID NO: 6) to PCR generate a 93-bp fragment. The more divergent region of the loop (designated PS2-loop D) was generated using primers D5' (SEQ ID NO: 7) and B3' (SEQ ID NO: 4). A construct encoding the final 40 amino acids of PS2 (designated PS2-C term) was created using primers E5' (SEQ ID NO: 9) and E3' (SEQ ID NO: 8). The corresponding loop B and loop C regions in PS1 were PCR amplified using primers F5' (SEQ ID NO: 11) with F3' (SEQ ID NO: 10) or G3' (SEQ ID NO: 12), respectively, from a full-length PS1 clone. The PS1-loop C region, which differs by only three amino acids from the corresponding PS2-loop (containing a threonine instead of a proline at position 281[see FIG. 1 A, numbered according to PS1], a leucine in place of an isoleucine at position 282, and a threonine for an alanine at position 291), was mutated at each of the three divergent residues, singly, and in every possible combination to the corresponding PS2 sequence using appropriate PCR primers and the QuikChange site-directed mutagenesis method (Stratagene). A control bait construct which contained the first 31amino acids of lamin B was obtained by PCR with primers L5' (SEQ ID NO: 16) and L3' (SEQ ID NO: 15) from lamin B cloned in pBluescript KS(–) (Mical and Monteiro, 1998).

All PCR-amplified regions were digested with EcoRI and XhoI, cloned into pEG202, and confirmed by DNA sequencing. These various baits were transformed into EGY48 and found by immunoblotting of yeast extracts to express appropriately sized lexA-PS fusion polypeptides. Three isolates from yeast transformed with the calmyrin in pJG4-5 (clone 7) plus each PS bait or the control lamin bait were assayed for β-galactosidase enzyme activity in liquid cultures using ONPG (O-nitrophenyl β-D-galactopyranoside) as a substrate (Reynolds and Lundblad, 1989).

4. Northern Blot Analysis $^{32}$P-labeled DNA probes were prepared via standard random primer labeling of 100 ng of full-length calmyrin cDNA or human β-actin cDNA control. A human multiple tissue Northern (MTN) blot and a human brain multiple tissue Northern blot II (Clonetech Laboratories, Inc.) were hybridized with the calmyrin probe at 68° C. overnight, washed in 0.1×SSC at 50° C., and exposed to film. The blots were then stripped of the calmyrin probe and reprobed with the β-actin control (Clonetech Laboratories, Inc.).

5. Bacterial GST Fusion Protein Expression

The original pGST construct or the pGST construct containing the complete calmyrin sequence fused COOH-terminally and in-frame with GST was transformed into CAG456 bacteria. Unfused GST and GST/calmyrin fusion protein induction with IPTG, incubation with glutathione agarose, and elution with reduced glutathione were performed as described in Janicki and Monteiro (1997).

6. Cloning of Eukaryotic Expression Constructs

The pGEM-CMV vector, a CMV-driven expression plasmid containing a COOH-terminal myc-tag (described in Janicki and Monteiro, 1997), was used for protein expression in HeLa cells. A calmyrin construct containing an in frame COOH-terminal myc epitope was created by PCR amplifying the calmyrin fragment from pBS-calmyrin with primers M5' (SEQ ID NO: 16) and M3' (SEQ ID NO: 15) resulting in a ~600 bp PCR product that was digested with SacII and SalI and ligated into pGEM-CMV.

An NH$_2$-terminal myc-tagged calmyrin construct was also created by PCR using primer N5' (SEQ ID NO: 18) with primer N3' (SEQ ID NO: 17) to introduce eleven residues of the myc epitope (Monteiro et al., 1994) followed by four residues encoded by 5' untranslated calmyrin sequence linked to the complete calmyrin coding sequence. The resulting ~600 bp PCR product was digested with SacII and SalI and ligated into pGEM-CMV.

An untagged full-length calmyrin expression construct was created by digesting pBS-calmyrin with SacII and XhoI, gel isolating the ~650 bp fragment, and ligating it to SacII/SalI linearized pGEM-CMV. The cloning and expression of both full-length PS2 and the PS2 construct deleted of loop and COOH-terminal sequence [pPS2(268aa)+Myc] were described previously (Janicki and Monteiro, 1997). Expression of full-length wild-type neurofilament light (NF-L) subunit was achieved using the CMV-NF-L expression construct (Lee et al., 1993).

7. Polyclonal Antibody Production

Purified GST/calmyrin protein and GST/PS2(NH$_2$-terminal) fusion protein (described in Janicki and Monteiro, 1997) were sent to Covance Research Products for inoculation into rabbits. The specificity of these rabbit antibodies was determined by imunoblotting (Janicki and Monteiro, 1997) and immunofluorescent staining of HeLa cell transfected with calmyrin or PS2. For immunoblotting, the anti-calmyrin and anti-PS2 antibodies were used at a 1/500–1/700 dilution and detected with horseradish peroxidase-conjugated goat anti-rabbit secondary antibodies and Super-Signal Substrate (Pierce Chemical).

8. HeLa Cell Culture and DNA Transfection

HeLa cells were grown in DME supplemented with 10% FBS and transiently transfected with appropriate plasmid DNAs as calcium phosphate precipitates (Janicki and Monteiro, 1997). Alternatively, 20 μg of DNA and 2×10$^6$ HeLa cells were electroporated at 960 μF and 0.3 kV.

9. Cell Staining and Immunofluorescence Microscopy

HeLa cells were transfected directly on glass coverslips, fixed, and antibody stained as described in Janicki and Monteiro (1997). Antibodies used were rabbit anti-calmyrin serum (diluted 1:250), goat anti-PS2(NH$_2$-terminal) antibody (diluted 1:150; Santa-Cruz Biotechnology, Inc.), rabbit anti-lamin serum (diluted 1:200; Mical and Monteiro, 1998), rabbit anti-NFL serum (diluted 1:250; generated in this lab using recombinant-purified, bacterially expressed, mouse neurofilament light chain), M30 CytoDEATH mouse anti-cytokeratin 18 antibody (diluted 1:50; Boehringer Mannheim), fluorescein- and rhodamine-conjugated donkey anti-rabbit, anti-goat, and anti-mouse antibodies (Jackson ImmunoResearch Laboratories, Inc.). Fluorescence staining of cells was visualized on an inverted Leica DM IRB microscope and images were captured using a Photometrics SenSys camera and manipulated with IPLab Spectrum and Multiprobe software (Scanalytics) on a Power Macintosh. Confocal microscopy and image processing was performed using the ×100 objective of a Leica confocal and imaging system (Leica Inc.).

10. Mouse Tissue Lysates and Primary Cultures

Spleen, brain, kidney, liver, heart, and skeletal muscle tissues were dissected from an adult mouse, chopped with a razor blade in 1–2 ml lysis buffer (Monteiro and Mical, 1996), homogenized on ice, briefly sonicated on ice, and centrifuged at 2,000 rpm for 5 min. Tissue lysate supernatants were collected, their protein concentration was determined by the BCA Protein Assay (Pierce), and 100 μg of each sample was separated by SDS-PAGE, transferred to nitrocellulose filters, and immunoblotted with the rabbit anti-calmyrin antibody.

Kidney and heart tissues from 8–12 mice that were 2-days olds were chopped with a razor blade, resuspended in 2 ml 0.25% collagenase in PBS, vortexed, incubated at 37° C. for 15 min, centrifuged, and washed 3 times with PBS. Cells were cultured in EGM medium supplemented with BBE (Clonetics) and 10% FBS for 2–7 d. For immunofluorescence, cells were cultured directly onto coverslips and fixed and stained as described above.

11. Cell Fractionation

Nondetergent soluble and insoluble fractions of HeLa cells were prepared essentially as described by Gerace and Globel (1980). HeLa cells (~1×10$^6$) were collected 24 hrs. after transfection by scraping the cells in ice-cold PBS and centrifugation at 10,000 g. The cells were resuspended in 0.25 ml 10 mM triethanolamine-HCL (pH 7.4), 10 mM KCl, 1.5 mM MgCl$_2$, 5 mM iodoacetamide, and 1 mM Pefabloc (Boehringer-Mannheim). After 10 min. incubation on ice, the cells were disrupted with 10 gentle strokes in a 0.5 ml Potter-Elvehjem homogenizer. Next, 0.25 ml of 10 mM triethanolamine-HCL (pH 7.4), 270 mM KCl, 1.5 mM MgCl$_2$, 5 mM iodoacetamide, and 1 mM Pefabloc were added and after mixing, the homogenates were centrifuged at 100,000 g for 15 min. in a Beckman TLX ultracentrifuge. The supernatants were removed and the pellets resuspended in lysis buffer (Monteiro and Mical, 1996) to a volume equal that of their respective supernatants. Triton X-100-treated HeLa cell fractions were prepared by lysing the transfected cells in 0.5 ml ice-cold 1% Triton X-100, 10 mM triethanolamine-HCL (pH 6.9), 140 mM KCl, 1.5 mM MgCl$_2$, 5 mM iodoacetamide, and 1 mM Pefabloc. After 10 min. incubation the lysates were centrifuged at 140,000 g for 15 min. Supernatants were collected and the pellets resuspended in lysis buffer. Equivalent volumes of the supernatant and pellet fractions of the detergent-treated and untreated cells were separated by SDS-PAGE and immunoblotted using the rabbit anti-calmyrin antibody or the rabbit anti-lamin antibody. The same cell fractionation procedure was used on primary cell cultures prepared from mouse kidney.

12. Myristoylation Experiments

After transfection, sodium pyruvate to a final concentration of 1 mM and 0.1–0.2 mCi $^3$H-myristic acid (Amersham Life Science Inc.) were added to the fresh media in each cell culture dish. At ~24 hrs. after transfection, cells were scraped off the bottom of the dish and the media was collected and centrifuged 5 min. at 3,000 rpm. The cell pellet was washed with PBS, centrifuged, resuspended in 400 μl lysis buffer (50 mM Hepes, 100 mM KCl, 0.3% NP40, 1 mM EDTA, 1 mM EGTA, pH 7.5, +protease inhibitor cocktail with aprotonin, leupeptin, and PMSF; Boehringer Mannheim), and homogenized on ice. Insoluble material was pelleted and the supernatant was collected and diluted with an equal volume of dilution buffer (50 mM Hepes, 1 mM EDTA, and 1 mM EGTA, pH 7.5). 150 μl of the lysates were incubated with 5 μl of antibody (rabbit anti-calmyrin, rabbit anti-PS2, or rabbit control preimmune serum) for 2 hrs. at 4 C. 45 μl of a slurry of protein A-Sepharose beads (Pharmacia Biotech, Inc.) was then added to the lysates and incubated with rotamixing for another 1 hr. The beads were pelleted by centrifugation, and after removal of the supernatant, the beads were washed four times with lysis/dilution buffer. All of the immunoprecipitate and one-sixth of the supernatant sample were separated by SDS-PAGE. After Coomassie blue staining and destaining, the gel was soaked for three 15 min. changes in DMSO, immersed in 22% PPO (2,5-diphenyloxazole) for 90 min, washed in water, dried, and exposed to film by fluorography for 1 wk to 2 mo.

13. Affinity Chromatography

After ~24 h, mock or PS2-transfected HeLa cells (~1×10$^6$ cells) were washed in ice-cold PBS, scraped into PBS, and pelleted by centrifugation for 5 min. at 3,000 rpm. The cells were resuspended in 400 μl of lysis buffer (see myristoylation section), sonicated, and homogenized on ice. Insoluble material was pelleted and the supernatant was collected and diluted with an equal volume of dilution buffer. All of the soluble lysate was incubated overnight at 4° C. with CNBr-activated Sepharose beads (Pharmacia Biotech, Inc.) coupled with an equivalent amount (240 μg) of either purified GST or GST/calmyrin. The Sepharose beads were then pelleted by centrifugation and supernatant containing unbound protein was removed. The beads were washed with 2.5 M KCl, resuspended in Laemmli buffer, and ½ of the sample was separated by SDS-PAGE and immunoblotted for the presence of PS2 using a goat anti-PS2(NH$_2$-terminal) antibody.

14. Quantification of Cell Death

Duplicate dishes of HeLa cells (plated at ~3×10$^5$/100 mM dishes) were transfected with various combinations of pGEM-CMV-calmyrin, pGEM-CMV-PS2, and control vector (a CAT basic expression vector; Promega). After ~48 hrs, floating cells from each dish were harvested by collecting all of the media, centrifuging 5 min. at 3,000 rpm, and removing all but ~0.5 ml of the supernatant. After vortexing, the exact volume of each cell suspension was measured. Cell numbers were counted twice for each sample on a hemacytometer. These cell counts were adjusted according to the initial resuspension volume to give the total number of floating cells per dish. The counts for the two independent dishes of each transfection construct combination were averaged and graphed. There was a direct correspondence between floating cells and apoptotic cells, with ~85% of floating cells showing positive CytoDEATH staining.

Experimental Results

A. PS2-Loop Interaction Trap Identifies a Calcium-binding Protein, Calmyrin

Using the yeast two-hybrid system, a human fetal brain cDNA library was screened for proteins that bind the loop region of PS2. Full-length PS2 was unsuitable as bait presumably because it could not be transported into the nucleus due to the presence of hydrophobic transmembrane domains. After finding that the initial PS2-loop construct (residues 270–361) self-activated transcription, the bait was truncated reducing it to the first 50 amino acids of the PS2 loop in order to eliminate several acidic residues and this portion was designated as PS2-loop B (B for bait; FIG. 1). The PS2-loop B bait construct, the lacZ reporter plasmid, and human fetal brain cDNA library plasmids were transformed into yeast, and out of 1.5×10$^7$ primary transformants screened, 15 putative interactors were isolated. Isolated library prey plasmids were tested for their ability to reproduce the specific interaction phenotype when coexpressed with the loop bait but not with unrelated baits (such as human lamin B). Clones that produced the specific interaction phenotype were sequenced and identified via BLAST homology database search. Interestingly, three of the interactors were independent cDNAs all containing the full coding sequence of a recently identified calcium-binding protein, but with varying NH$_2$-terminal untranslated extensions.

Two other groups have recovered this calcium-binding protein in yeast two-hybrid screens and have named it CIB, for its calcium- and integrin IIb-binding ability (Naik et al., 1997), and KIP, due to its interaction with eukaryotic DNA-dependent protein kinase, DNA-PKcs (Wu and Lieber, 1997). Rather than pick between these two names this protein was named calmyrin (for calcium-binding myristoylated protein with homology to calcineurin)

because it describes its inherent properties without bias towards its multiple binding partners.

Figure 2:
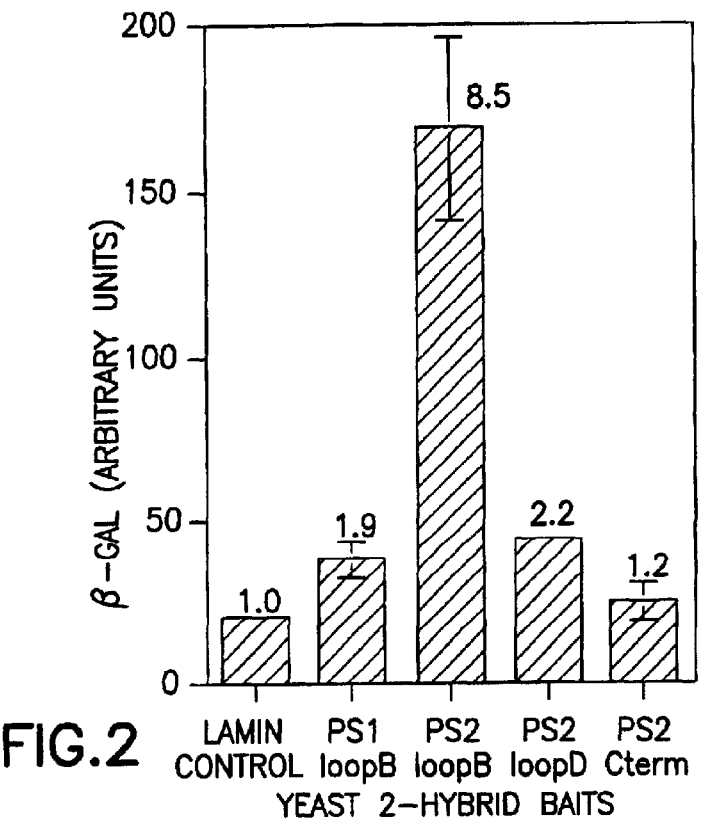
FIG. 2 and 3 shows the results of yeast two-hybrid liquid assay using the baits described in FIG. 1.

To quantify the binding specificity of calmyrin to the PS2-loop and to determine if this protein also interacts with the PS1 loop which is 45% identical in amino acid sequence, the galactosidase activity was measured in yeast liquid assays. When cotransformed with calmyrin, the PS2-loop B bait produced an 8.5-fold increase in-galactosidase activity over the lamin B negative control, while the corresponding region of PS1 (PS1-loop B) produced only a 1.9-fold increase in activity (FIG. 2). A PS2-COOH-terminal construct, containing the COOH-terminal 39-amino acid sequence downstream of the eighth TMD also did not appear to interact with calmyrin.

Figure 3:
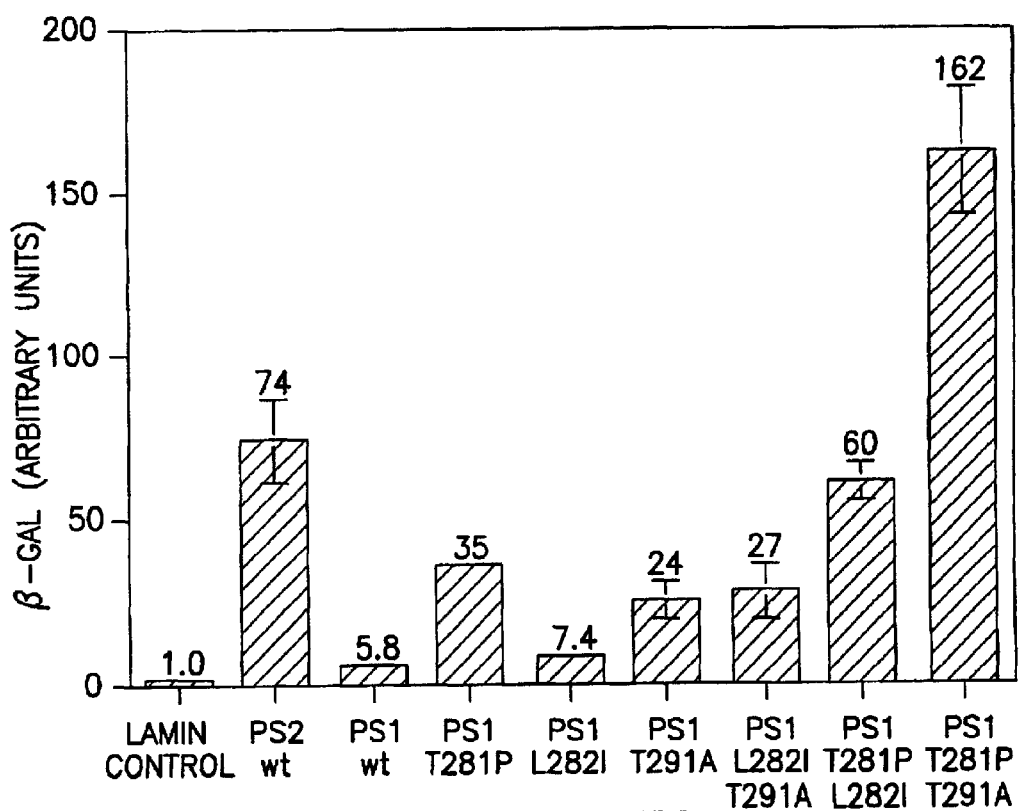

To further map the binding site of calmyrin within the PS2-loop, two new baits were constructed which divided the loop into a conserved portion, loop C (28 out of the 31 amino acids are identical to PS1 ), and a divergent region, loop D (only 33% identity to PS1; FIG. 1). Since calmyrin did not interact preferentially with the comparable loop region of PS1 (PS1-loop B) it was expected that the calmyrin binding would be within the divergent region of the PS2-loop sequence (PS2-loop D). Surprisingly, the PS2-loop D bait interacted very weakly with calmyrin, a 2.2-fold increase over control (FIG. 2). However, the highly conserved region of the PS2 loop, PS2-loop C, produced a 74-fold increase in activity (FIG. 3). In comparison, the corresponding PS1-loop C construct increased activity only 5.8-fold.

Although the two PS-loop C baits are highly conserved in sequence, they differ by three amino acids, with PS1 containing threonine residues at positions 281 and 291 instead of proline and alanine that are located at positions 287 and 297 of PS2 (see FIG. 1, numbered according to PS1), and a leucine at position 282 instead of an isoleucine that is located at position 288 of PS2. Further investigation was performed to determine how these three divergent residues influenced calmyrin interaction with the PS-loop C region in yeast two-hybrid assays. Accordingly, the PS2 amino acids at these respective sites on the loop (287, 288 and 297) were introduced into the PS1 bait at the corresponding sites (281, 282, and 291), so that each of the three divergent residues were mutated singly, and in every possible combination, to the corresponding PS2 sequence. These data indicated that all three residues contributed in different and complex ways towards the interaction (FIG. 3). with calmyrin. Interestingly, calmyrin interaction was restored to approximately half the PS2 level by a single mutation at residue 281 of PS1, that being, changing a threonine and replacing with a proline residue which would be predicted to introduce a kink in the loop. In comparison, a single mutation of residue 282 in PS1 from a leucine to an isoleucine did not increase binding to any significant extent, whereas mutation of residue 291 from a threonine to an alanine increased binding to a third of the PS2 level. Double mutants confirmed the importance of residues 281 and 291. When both proline and alanine were present together (T281P, T291A) they increased binding substantially, producing an approximately twofold higher level of binding compared with the wild-type PS2-loop bait. This mutant suggests that isoleucine at residue 281 in PS1 may actually compromise binding of calmyrin, as this would be equivalent to the triple substitution (T281P, L282I, T291A; i.e., turning it back to the PS2 sequence). Consistent with this expectation, isoleucine 282, when present together with alanine 291, both substituted on the PS1 protein, did not increase binding above that of the latter alone, whereas paradoxically when isoleucine 282 was substituted together with proline 281, on the PS1 protein, it increased binding 1.7-fold higher than when proline was substituted alone.

Thus, the replacement of amino acid residues at positions 281 and 291 on PS1 with those amino acids located at 287 and 297 of PS2 indicated that the positions of 287 and 297 are important and reactive sites that enhance interaction between PS2 and calmyrin. As such, amino acid substitution, deletion or insertion at sites 287 and 297 may reduce interaction of the PS2 protein with normal calmyrin. Further, this discovery provides for use of a mutant protein that can be administered or expressed to reduce interaction between presenilin 2 and calmyrin by several methods including competitive binding to reactive sites of either protein. Further, antibodies specific for normal presenilin 2 and calmyrin, specific for reactive sites may be raised for administration to reduce biological activity of the proteins and inhibit the deleterious effects of the protein-protein interaction.

B. Relevant Properties of Calmyrin

Figure 5:
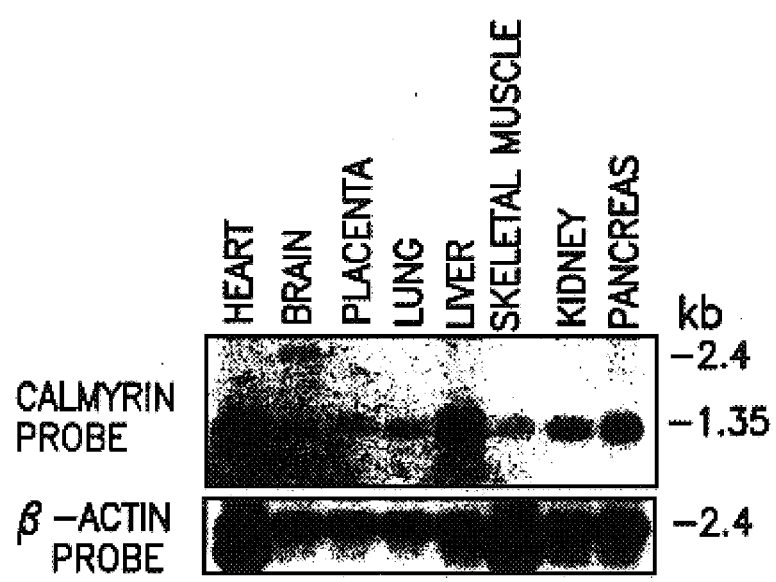
FIG. 5 shows the results of human multiple tissue Northern Blot.
Figure 6:
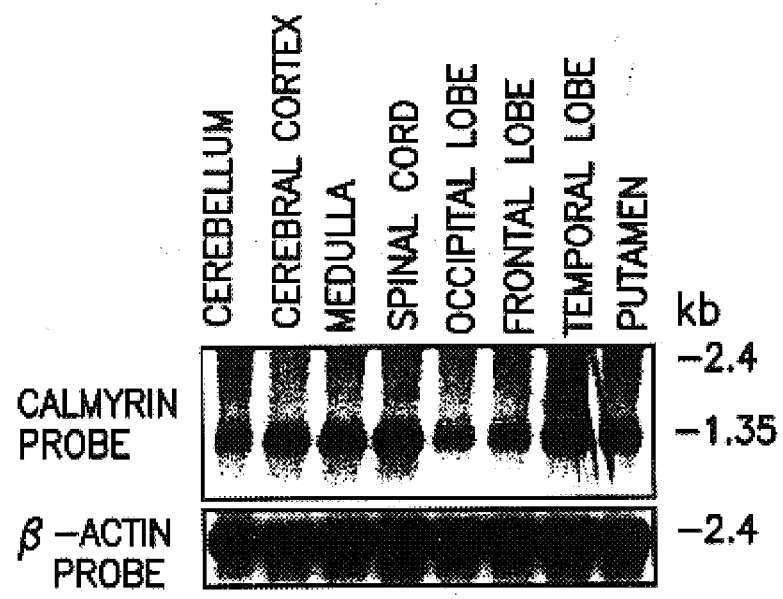
FIG. 6 shows the results of human brain multiple tissue Northern Blot.

The 191-amino acid sequence of calmyrin has a number of notable features (FIG. 4 and SEQ. ID NO: 2). Sequence comparison indicates that calmyrin is most closely related to human calcineurin B, the regulatory subunit of protein phosphatase 2B, sharing 25% identity and 44% overall similarity. The protein contains two complete EF-hands, a conserved motif involved in calcium binding, and in fact, was shown to bind radiolabeled calcium in blot overlay assays (Naik et al., 1997). The protein also contains an NH2 consensus myristoylation site, a cotranslational modification involved in targeting proteins to membranes. To verify the size and expression pattern of calmyrin transcripts, Northern blot analysis of poly(A)$^+$ RNA isolated from multiple adult human tissues was performed (FIG. 5). The calmyrin probe hybridized to a ~1.2 kb transcript was ubiquitously expressed in the tissues examined, extending the evidence that it is widely expressed (Naik et al., 1997; Wu and Lieber, 1997) and implying that it plays a common function in most if not all cells. Although mRNA expression was relatively low in brain, a Northern blot of specific brain regions showed that the expression of calmyrin transcripts was easily detectable and fairly uniform (FIG. 6).

Figure 7:
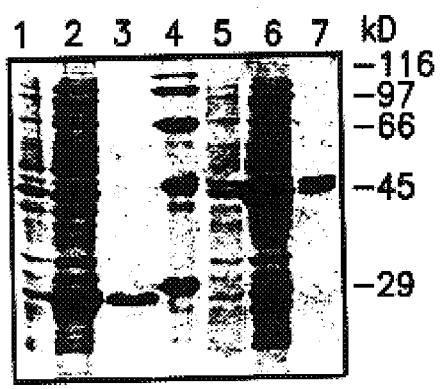
FIG. 7 shows Coomassie Blue stained gel documenting the induction and purification of GST (1–3) and GST/calmyrin (5–7).
Figure 8:
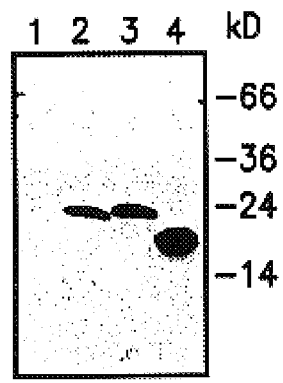
FIG. 8 shows the immunoblot of HeLa cell lysates probed with rabbit anti-calmyrin.
Figure 9:
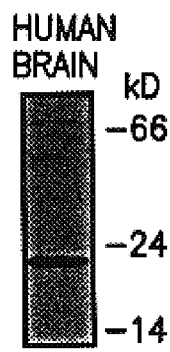
FIG. 9 shows the immunoblot of human brain lysates probed with rabbit anti-calmyrin.
Figure 10:
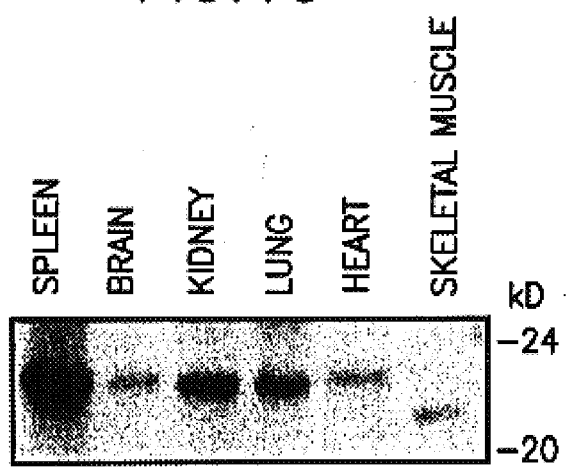
FIG. 10 shows the immunoblot of various mouse tissues probed with anti-calmyrin to detect endogenous levels of calmyrin.

C. Tissue Distribution and Subcellular Localization of Endogenous Calmyrin Protein To further study,the calmyrin protein, rabbit polyclonal anti-calmyrin antibodies were generated to affinity-purified GST/calmyrin fusion protein (FIG. 7, lane 7). By immunoblotting, these antibodies appeared to be highly specific for calmyrin as they reacted only with the appropriately sized polypeptides (~22–25 kD) in HeLa cells overexpressing calmyrin cDNAs (FIG. 8). Lane 1 of FIG. 8 shows that at the depicted exposure time the antibodies failed to detect any endogenous calmyrin in untransfected lysate. Only after prolonged exposure did a faint calmyrin band appear (data not shown), indicating that endogenous levels of this calcium-binding protein are relatively low in HeLa cells. However, consistent with our Northern blot analysis, an endogenous immunoreactive band at ~22 kD was detected in human adult brain lysate (FIG. 9). The anti-calmyrin antibodies also successfully detected the mouse form of this protein in several mouse tissue lysates (FIG. 10) due to the high conservation between the human and mouse calmyrin proteins (only five dissimilar residues; Saito et al., 1999).

Figure 11:
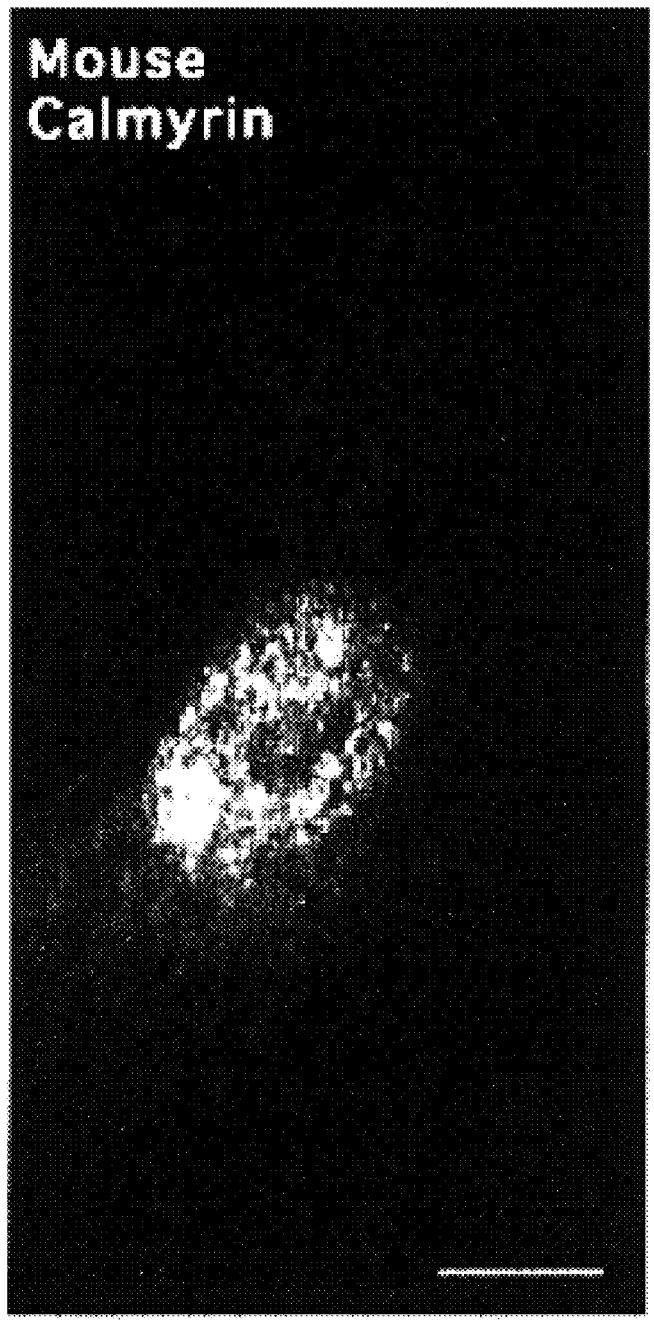
FIG. 11 shows immunofluorescent localization of endogenous calmyrin in mouse heart primary cell culture.

Since the subcellular localization of calmyrin was unknown, the anti-calmyrin antibody was used to determine its distribution in mammalian cells by indirect immunofluorescence microscopy. In primary cultures from mouse heart tissue endogenous calmyrin localized to the nucleus and in a reticular-like pattern throughout the cytoplasm (FIG. 11). This staining was clearly distinguishable from the nonspecific background produced when probing with rabbit preinoculation serum (data not shown), and moreover, this staining pattern was reproduced by overexpression of calmyrin upon transfection (see below).

D. Calmyrin Is Myristoylated and Membrane Associated

Figure 12:
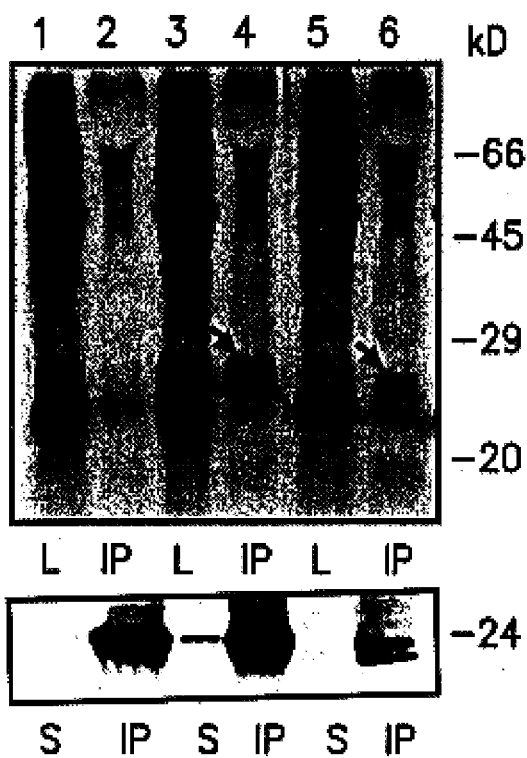
FIG. 12 shows a fluorograph of myristoylated proteins immunoprecipitated with rabbit anti-calmyrin from HeLa cells after transfection with N-myc calmyrin (1,2) C-myc calmyrin (3,4), or wild type calmyrin (5,6).

As PS2 is a transmembrane protein and the yeast two-hybrid findings indicated that calmyrin interacts with PS2, the membrane targeting potential of the consensus myristoylation site in calmyrin especially was intriguing. To determine whether calmyrin is myristoylated in vivo, $^3$H-myristic acid was added to the media of HeLa cells transfected with untagged calmyrin. For comparison, HeLa cells were also transfected with calmyrin constructs that had myc tags fused at either the $NH_2$- or COOH-terminal ends of the protein. The prediction was that the myc tag (MEQKLISEEDLN) (SEQ ID NO: 29) fused at the $NH_2$-terminal end would disrupt myristoylation since it moved the glycine residue that is essential for myristoylation more downstream (Olshevskaya et al., 1997). After 24 hrs., the cells were lysed and calmyrin was immunoprecipitated with the anti-calmyrin antibody. Myristoylated proteins were visualized by fluorography after SDS-PAGE (FIG. 12). The fluorograph of labeled HeLa cell lysates indicated immunoprecipitated C-myc- tagged calmyrin and untagged wild-type calmyrin were myristoylated as evident by incorporation of the radioactive $^3$H-myristic acid label (band in lanes 4 and 6 indicated by an arrows) while, as expected, the N-myc tagging of the protein prevented myristoylation (absence of band in lane 2). The lower panel of this figure contains an immunoblot of these same HeLa cell lysates to show that both $NH_2$— and COOH-terminally tagged calmyrin proteins were expressed efficiently and to equivalent levels, whereas untagged calmyrin accumulated at lower protein levels, explaining the fainter myristoylated calmyrin band seen in lane 6 as compared with lane 4. In fact, when the ratio of calmyrin protein to radioactive $^3$H-myristic acid labeling is compared for C-myc-tagged and wild-type calmyrin proteins they are similar, which is expected since myristoylation is thought to occur cotranslationally (Wilcox et al., 1987).

Figure 13:
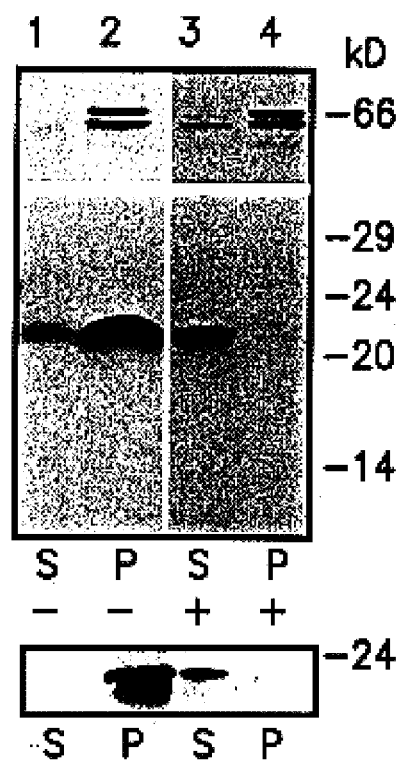
FIG. 13 shows immunoblotting of calmyrin expressing HeLa cell lysates for lamins A and C (68 and 66 kD) and calmyrin (22 kD) after fractionation in the absence (−) of detergent (1,2) or in the presence (+) of 1% Triton X-100 (3,4) into a soluble supernatant (S) and an insoluble pellet (P).

Once it was established that calmyrin was indeed myristoylated, next it was determined whether this protein was associated with the membranes of fractionated cells. Transfected HeLa cells were fractionated in the absence of any detergents into a soluble (cytosolic) supernatant and an insoluble (membrane and cytoskeletal) pellet. Equivalent amounts of supernatant and pellet cell fractions were separated by SDS-PAGE and immunoblotted for the presence of lamins and calmyrin (FIG. 13, lanes 1 and 2). Lamins A and C, cytoskeletal components used as a control of the fractionation process, were detected as 68 and 66 kD polypeptides in the insoluble pellet as expected (Gerace and Globel, 1980; Mical and Monteiro, 1998). The majority (>85%) of the calmyrin was found in the insoluble fraction. Since this manner of cell fractionation does not distinguish membrane components from other insoluble structures, the cells were also fractionated in the presence of 1% Triton X-100 which solubilizes membranes. After this procedure, the calmyrin protein shifted to the soluble (membrane) fraction whereas the lainins, as expected, remained insoluble (FIG. 13, lanes 3 and 4). The same fractionation was performed on primary cultures of mouse kidney and showed an analogous pattern of membrane localization for endogenous calmyrin (FIG. 13, lower panel). Interpreted together, these cell fractionation results provide strong biochemical evidence that calmyrin is associated with cell membranes.

Figure 14:
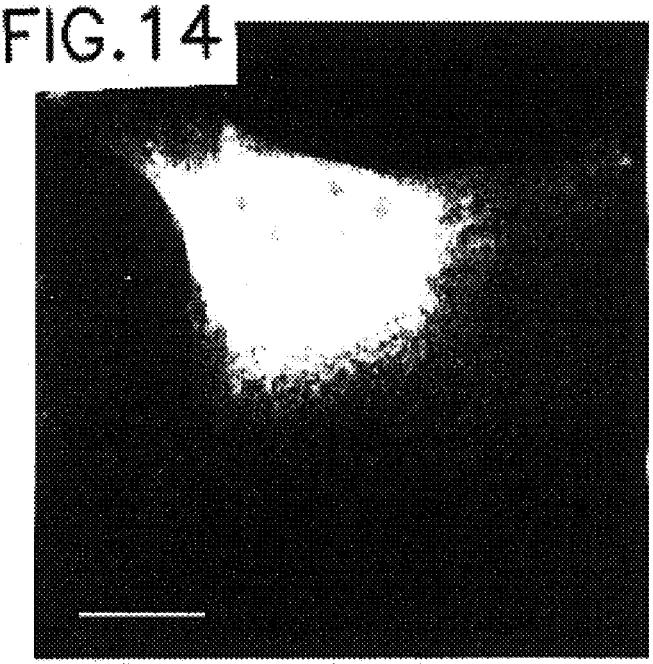
FIGS. 14–21 show immunofluorescent localization of calmyrin protein in transfected HeLa cells.
Figure 15:
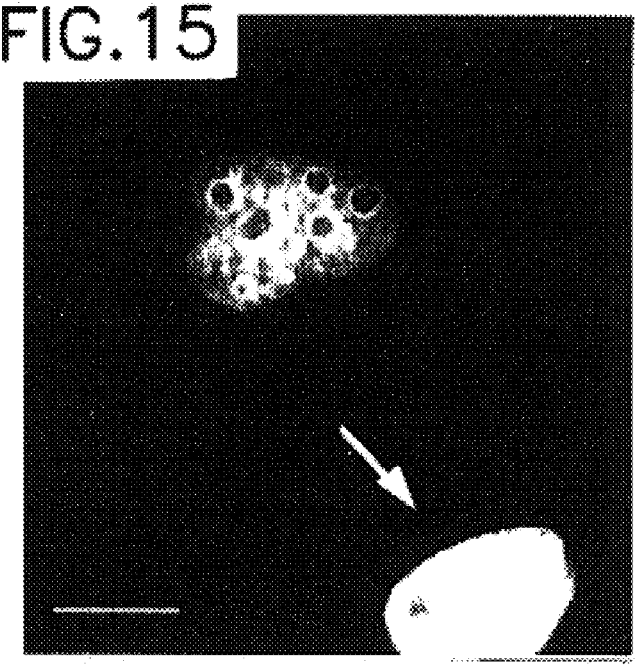
Figure 16:
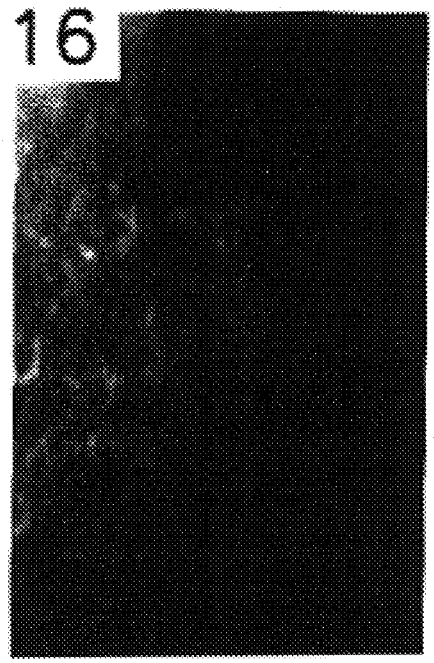
Figure 17:
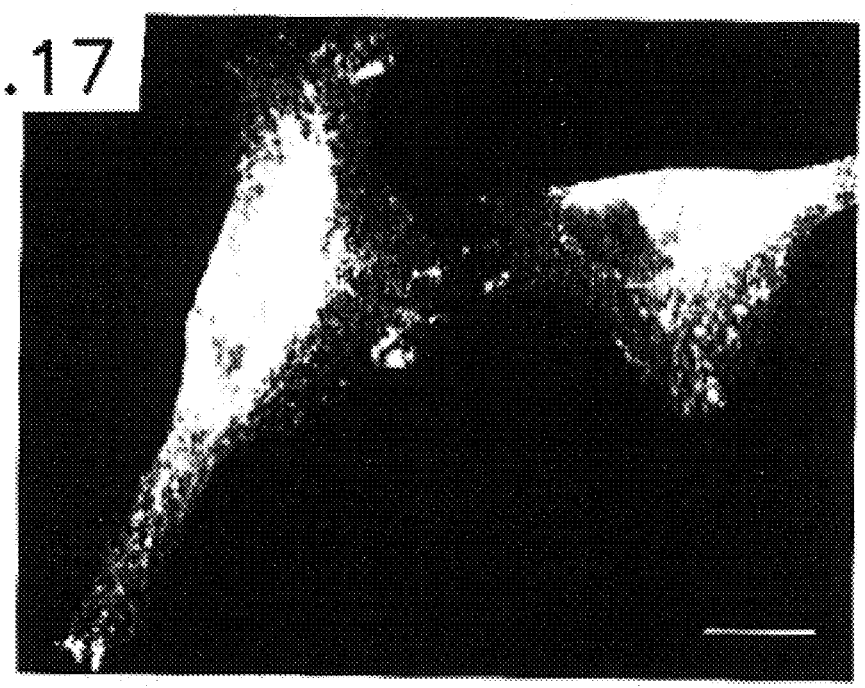
Figure 18:
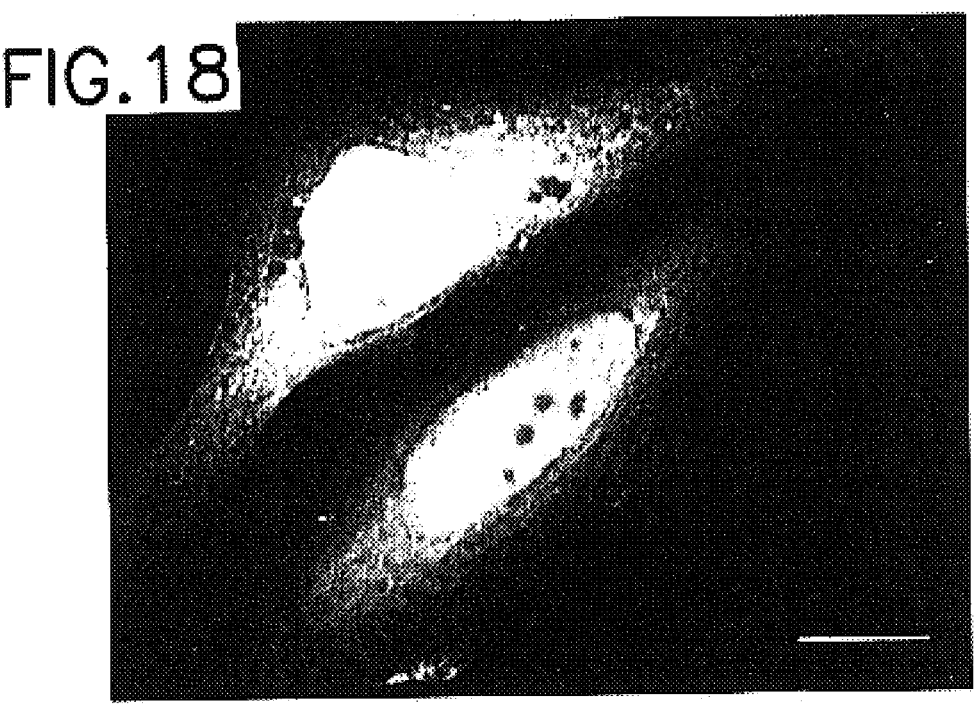
Figure 19:
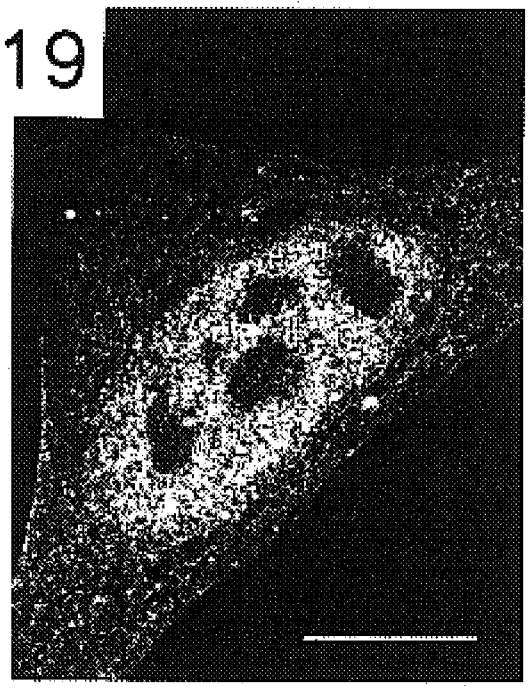
Figure 20:
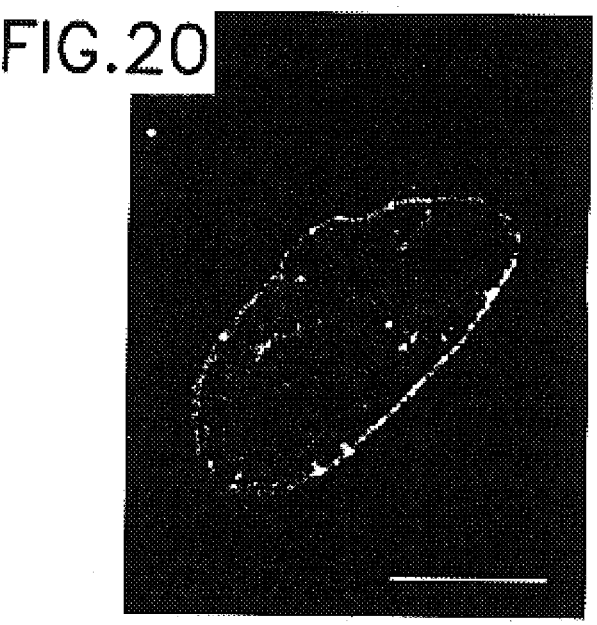
Figure 21:
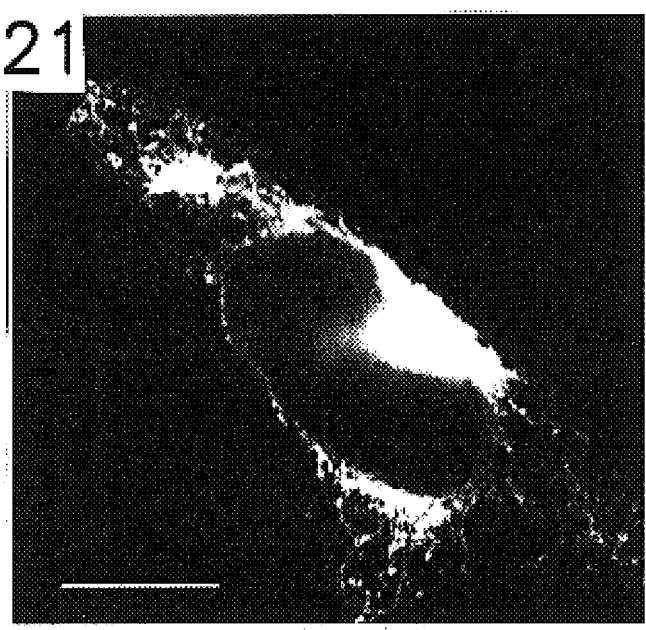

E. Calmyrin Accumulates in the Nucleus and Cytoplasm, but When Coexpressed with PS2 these Two Proteins Colocalize at the ER On account of the faint staining of endogenous calmyrin in primary and established cell cultures, calmyrin was forcibly expressed in HeLa cells by transient transfection of untagged and myc-tagged calmyrin constructs for further immunofluorescent localization studies. As seen in FIG. 14, cells expressing untagged calmyrin had strong staining in the nucleus and cytoplasm, a pattern very similar to the subcellular localization of endogenous calmyrin detected in mouse cells. At higher magnification, many of these transfected cells showed clear calmyrin staining of thin projections from the cell surface as well as a reticular staining in the cytoplasm consistent with membrane targeting to the plasma membrane and ER (FIG. 16). Cells expressing C-myc calmyrin had greater variation in staining with many showing prominent localization to the ER and plasma membrane and often less staining in the nucleus (FIG. 17). Double immunofluorescence staining for calreticulin, an ER marker protein, and calmyrin showed that within the cytoplasm a notable portion of calmyrin colocalized with calreticulin (data not shown), corroborating the impression that in these transfected cells calmyrin localization includes, but is not limited to, ER membranes. In contrast, cells expressing N-myc calmyrin showed predominant nuclear staining, more diffuse cytoplasmic staining, and less staining at the plasma membrane which was especially evident in low expressing cells (FIG. 18). This observed reduction in membrane association was not surprising considering previous finding showing that this $NH_2$-terminally tagged construct failed to be myristoylated. To address whether the bright nuclear staining was due to calmyrin localization within the nuclear envelope or throughout the nucleoplasm, wild-type calmyrin transfected HeLa cells was double stained for calmyrin and lamins A/C. According to confocal microscopy, lamins A and C had rim fluorescence (FIG. 20) consistent with their known localization as a caged meshwork of filaments tethered to the inner nuclear envelope (see Mical and Monteiro, 1998). In the same confocal Z-section (1.0-$\mu$m section) where lamins had rim fluorescence, calmyrin immunoreactivity was present throughout the cell and clearly within the nucleoplasm (FIG. 19). Overall, these results indicated calmyrin localizes to many different cellular compartments, consistent with the protein having dynamic targeting properties. Of particular interest was the comparison of calmyrin and PS2 staining patterns when overexpressed individually in HeLa cells. Although the two staining patterns overlapped in part, especially the ER reticular staining of untagged and C-myc calmyrin, PS2 staining was readily distinguishable by its exclusive ER and nuclear envelope staining pattern (FIG. 21).

Figure 22:
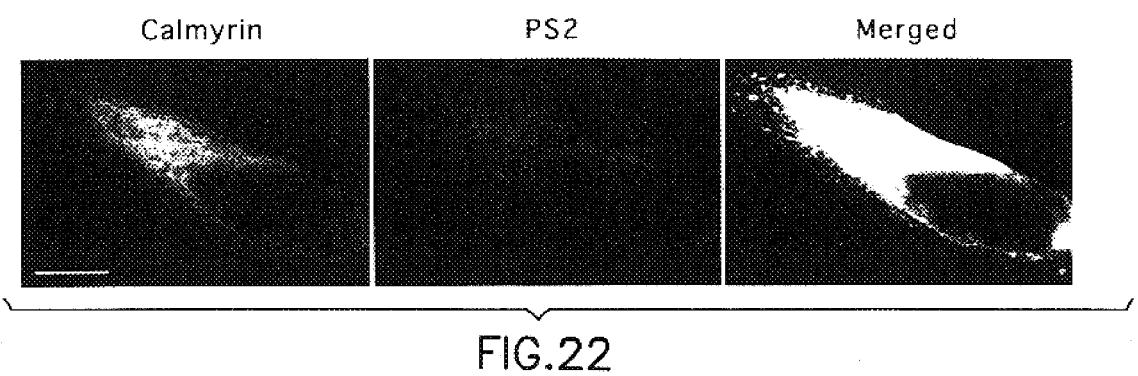
FIGS. 22–24 show immunofluorescent colocalization of calmyrin with PS2 in transfected HeLa cells, where the left hand panels show fluorescein labeled calmyrin, the center panels show rhodamine labeled PS2, and the right hand panels show a merged image indicating when the fluorescein and rhodamine signals colocalize.
Figure 23:
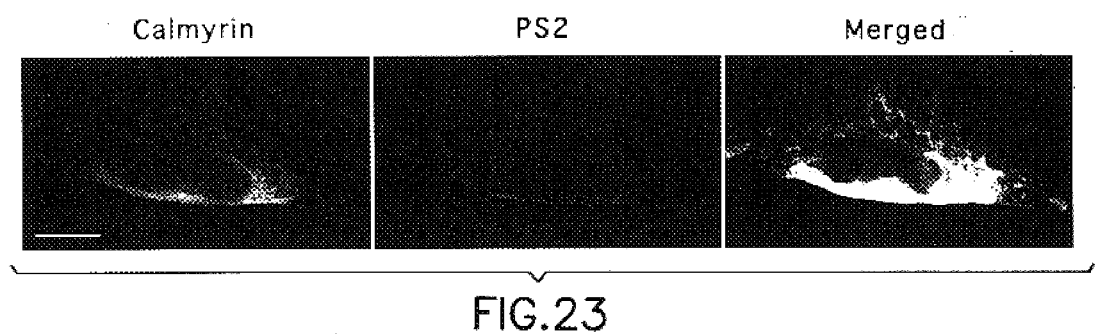
Figure 24:
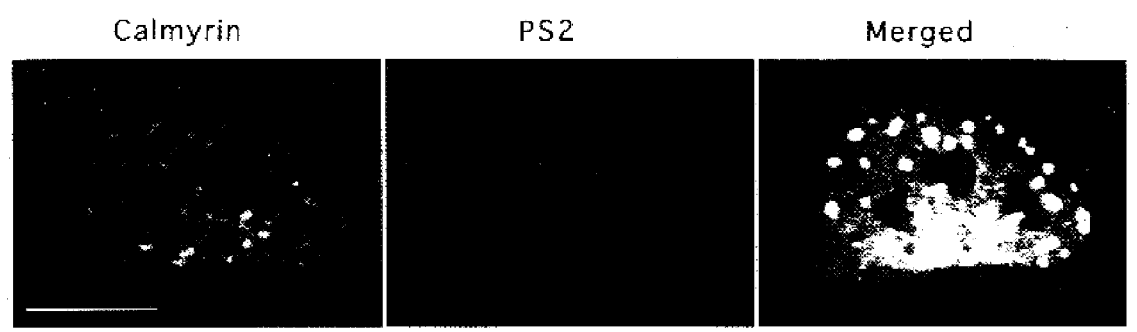

When calmyrin was coexpressed with PS2, its staining pattern was dramatically altered such that it colocalized almost completely with PS2 (FIGS. 22–23). As exemplified by the two cells shown in panels A and B, the calmyrin protein was less apparent in the nucleus in coexpressing cells than in cells transfected solely with calmyrin (FIG. 14). Another indication that these two proteins bind each other was seen in a small subset of cells where calmyrin and PS2 colocalized distinctively in unusual intranuclear spots (FIG. 24). The intranuclear spots did not colocalize with anti-centromere staining by double immunofluorescent microscopy (data not shown) suggesting that they are distinct from the PS-immunoreactive structures observed by Li et al.

Figure 25:
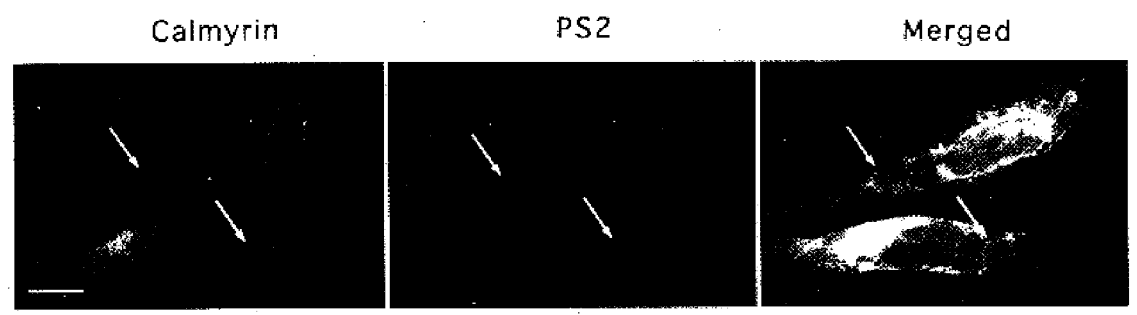
FIG. 25 shows similar staining of HeLa cells cotransfected with wild type calmyrin and loop/COOH deleted PS2.

(1997). The shift in calmyrin localization and the nearly identical staining patterns between PS2 and calmyrin (see merged images) in these coexpressing cells provide persuasive evidence that these two proteins interact in vivo. Furthermore, when calmyrin was cotransfected with a PS2 construct deleted of the loop and all sequence COOH-terminal of it, the staining patterns displayed significantly less overlap; as seen by patchy aggregates of PS2 which excluded calmyrin (FIG. 25, indicated by arrows). The failure of this PS2 deletion construct to completely colocalize with calmyrin in aggregates, which contrasts with the colocalization of the wild-type PS2 protein and calmyrin in nuclear inclusions, enhances speculation that the PS2-loop region facilitates binding of calmyrin.

F. Affinity Chromatography and Immunoprecipitation Confirm Binding between Calmyrin and PS2

Figure 26:
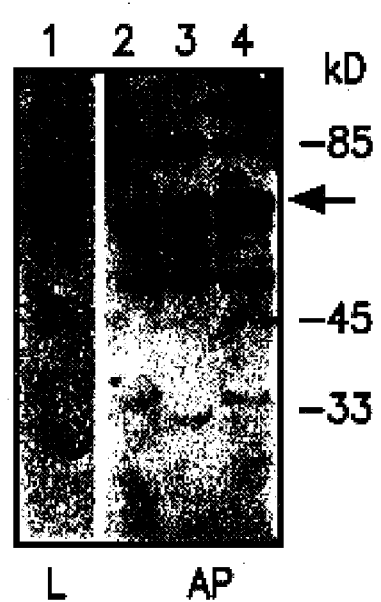
FIG. 26 shows an immunoblot of PS2 expressing HeLa cell lysates (L) which were affinity purified (AP) over OST-sepharose or GST/calmyrin sepharose probed with goat anti-PS2.
Figure 27:
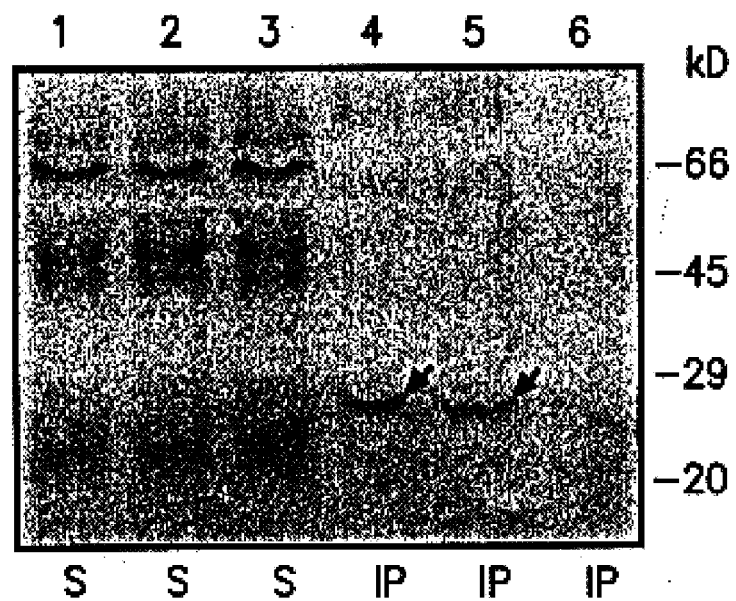
FIG. 27 shows a fluorograph of myristoylated proteins immunoprecipitated with rabbit anti-calmyrin (1,4), rabbit anti-PS2 (2,5), or rabbit preimmune serum (3,6) from C-myc calmyrin and PS2 cotransfected HeLa cells incubated for 24 hours with $^3$H-myristic acid.

To demonstrate interaction between calmyrin and PS2 in vitro, HeLa cell lysates of overexpressed PS2 were incubated with purified GST-calmyrin, or GST alone, (shown in FIG. 7) that had been covalently coupled to Sepharose. The two Sepharose columns were then washed, and retention of PS2 was determined by immunoblotting with anti-PS2 antibody. FIG. 26 shows that GST-calmyrin Sepharose bound PS2 with approximately threefold greater affinity (lane 4, see arrow) than control GST-coupled Sepharose (lane 3). The second verification of binding was the coimmunoprecipitation of myristoylated calmyrin protein from cotransfected HeLa cell lysates with anti-PS2 antibodies (FIG. 27, lane 5). The myristoylated calmyrin protein did not immunoprecipitate when the preimmune anti-PS2 serum was used (FIG. 27, lane 6) but, as expected, could be immunoprecipitated with the anti-calmyrin antibody (FIG. 27, lane 4).

G. Overexpression of Calmyrin Causes Apoptosis

Figure 34:
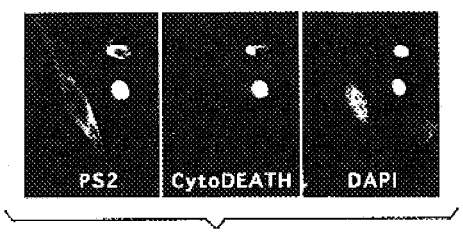
FIGS. 34–38 show immunofluorescent staining with CytoDEATH that indicates overexpression of PS2 and calmyrin increases HeLa cell apoptosis.
Figure 35:
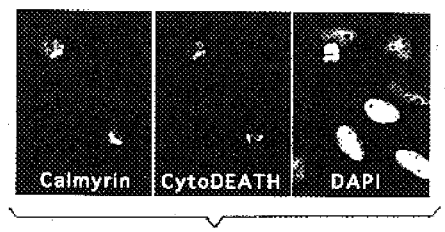

Since it was previously shown that overexpression of PS2 in HeLa cells causes apoptosis (Janicki and Monteiro, 1997), we wished to determine what effect overexpression of calmyrin would have on cell viability. To detect apoptosis we used the M30 CytoDEATH antibody. This mouse monoclonal binds an epitope of cytokeratin 18 which is exposed only after caspase cleavage, an early event in apoptosis (Caulin et al., 1997). Consistent with previous findings, FIG. 34 shows that a subset (two out of three) of cells overexpressing PS2 appeared apoptotic according to both CytoDEATH positive staining and condensed nuclei. Similarly, when calmyrin was overexpressed, analogous apoptosis was observed (FIG. 35).

Figure 36:
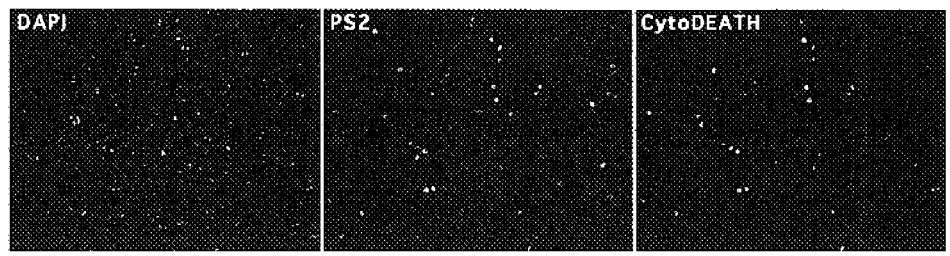

Cotransfection of PS2 and calmyrin induced even higher apoptosis. To convey more clearly the high levels of apoptosis that resulted from overexpressing these two proteins, example images captured at low magnification are provided. FIG. 36 shows that at 16 hrs. after cotransfection almost 13% of PS2-expressing cells (which presumably also expressed calmyrin since PS2 and calmyrin staining showed a near 1:1 correspondence [data not shown]) on coverslips were positive for CytoDEATH staining. By 40 hrs. the proportion of apoptotic cells had increased to ~50% of the PS2-stained cells. The high level of apoptosis seen on coverslips was striking, especially since this method only captured a brief "window" of the cells progression into apoptosis as during programmed cell death HeLa cells lose their adherence on coverslips and float away into the media.

Figure 37:
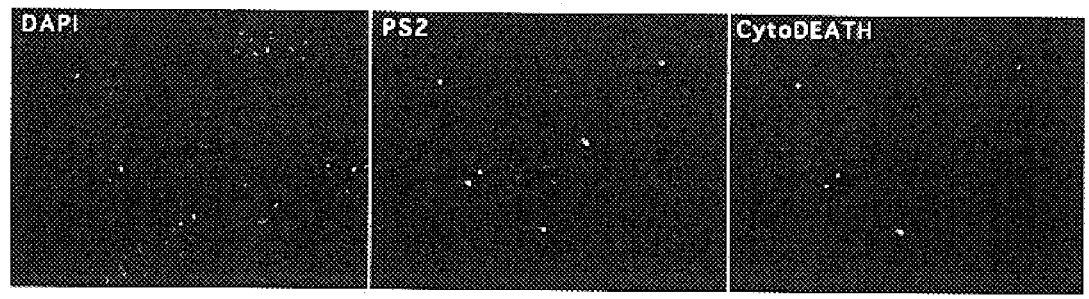
Figure 38:
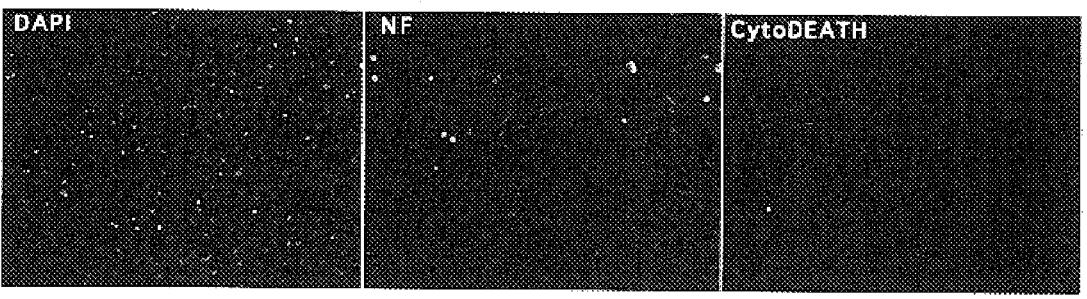

This phenomenon explains the reduction in total cells, and most notably PS-expressing cells (only 10 cells), remaining on the coverslip at 40 hrs. after cotransfection (FIG. 37). In the examples shown in FIGS. 34–37 only a subset of PS overexpressing cells were apoptotic, indicating a time-dependent process, whereas the corollary that all apoptotic cells were also overexpressers always held true. In contrast when a control protein, the neurofilament light (NF-L) subunit, was overexpressed in HeLa cells (FIG. 38), minimal apoptosis (<1%) was detected and total cell counts and expression levels remained high even at 40 hrs. It is remarkable that the single apoptotic cell in this field did not stain for NF-L and that, conversely, there are several rounded-up and highly expressing cells (presumably those in mitosis), none of which appeared apoptotic. Fields of cells overexpressing calmyrin or PS2 individually showed levels of apoptosis above the neurofilament background, but less than coexpressers.

Figure 39:
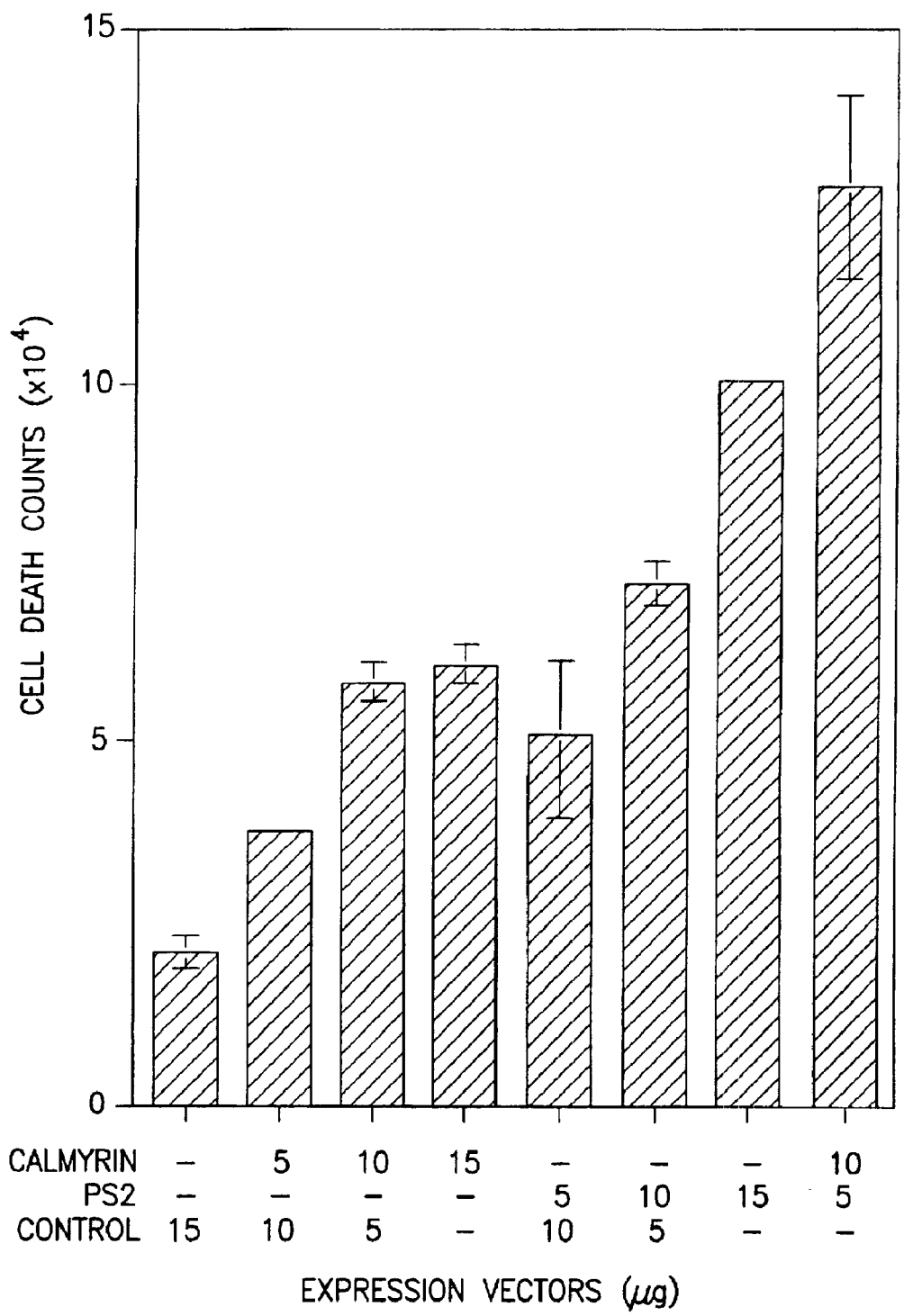
FIG. 39 is a graph quantifying cell death induced by overexpression of PS2 and calmyrin.

Because CytoDEATH labeling on coverslips only captured a narrow "window" of cells undergoing apoptosis, it was decided to quantify the total amount of cell death accumulated over time by counting the total number of floating cells in the media after transfection with various amounts of plasmid DNAs encoding calmyrin and PS2. It is believed that this simple method was more reliable in quantifying cell death. As graphed in FIG. 39, transient overexpression of PS2 increased cell death in a dose-dependent manner, whereas cell death induced by calmyrin overexpression reached a plateau at 10 $\mu$g of transfected DNA. More interestingly, when both proteins were coexpressed in the linear cell death range of their respective DNAs, cell death increased 5.9-fold over the control, compared with 2.7 and 2.4 fold for the same respective transfection amounts of calmyrin and PS2 individually, suggesting that these two proteins have additive effects in promoting cell death. When these floating cells were collected and stained with the CytoDEATH antibody, ~85% of the cells stained positive for this marker of apoptosis, bolstering beliefs that counting floating cells is a reliable measure of cell death.

Thus, it has been demonstrated, by several criteria, that human PS2 protein interacts with a calcium-binding protein which we named calmyrin. First, calmyrin interacts with PS2-loop sequence in yeast two-hybrid assays. Second, the two proteins bind to each other by affinity chromatography and can be coimmunoprecipitated. Third, the two full-length proteins colocalized when coexpressed in vivo. The interaction of calmyrin with PS2 is also noteworthy since it is the first protein, known to date, that interacts preferentially with PS2 suggesting distinct functions for the highly homologous presenilin proteins.

Two lines of evidence favor the PS2-loop region as the critical site of calmyrin interaction: reduced in vivo colocalization when calmyrin was coexpressed with a loop-deficient PS2 construct; and increased yeast liquid culture binding of calmyrin to the PS2-loop rather than the PS2-COOH-terminal domain. Deletion analysis indicated that calmyrin binding was mediated primarily by the $NH_2$-terminal 31 amino acids of the PS2-loop. Remarkably, despite only a three-amino acid difference, the comparable loop region of PS1 interacted with less than one-tenth the strength in similar yeast two-hybrid assays. Site-directed mutagenesis in which the three divergent PS2 residues were introduced singly and in double combinations into PS1 indicated that, in fact, all three amino acids produce variable affects on the specificity of calmyrin for PS2. Particularly interesting was the pronounced increased in binding between PS1 and calmyrin conferred by the conversion of a threonine at positions 281 and 291 in PS1 to proline and alanine, respectively. In contrast, the leucine at position 282 in PS1 when converted to isoleucine, as in PS2, caused pleotrophic effects, increasing, decreasing, and inducing no change in interaction depending on its context with the other two residues. These data suggest that minor alterations in the sequence of the PS loop induce conformational changes in this region with dramatic consequences to protein-protein interactions. Furthermore, the loop region is a site associated with several PS-processing phenomena, including proteolytic cleavage, caspase cleavage, as well as abnormal splicing (Perez-Tur et al., 1995; Thinakaran et al. 1996; Kim et al., 1997; Loetscher et al., 1997; reviewed by Hass, 1997). The data showing that minor (single amino acid) alterations in the loop sequence can produce dramatic changes in protein binding not only has implications in terms of calmyrin function, but may also have important consequences for the other processing events and binding partners associated with this region.

In addition to the importance of protein-protein interactions for localization, immunofluorescence microscopy and biochemical fractionation studies indicated that the myristoylation of calmyrin is important for the dynamic targeting of the calmyrin protein to several subcellular compartments including: the cytoplasm, long projections of the plasma membrane, and the nucleoplasm. Calcium-myristoyl switches are a known mechanism for protein targeting and signal transduction. Radiolabeling and biochemical studies show that calmyrin is myristoylated and associated with membranes.

Yeast two-hybrid assays with loop constructs containing site-directed mutations clearly show the importance of protein-protein interactions in mediating the association between calmyrin and the integral membrane protein, PS2. Additionally, fusion of the Gal4-acidic blob sequence at the $NH_2$-terminal end of calmyrin in the yeast two-hybrid clones would be expected to prevent this fatty acid modification suggesting that myristoylation is not essential for the interaction. Paradoxically, however, it is the myristoylated form of calmyrin that was shown to coimmunoprecipitated with PS2. Perhaps insertion of the myristoyl group into the lipid bilayer initiates a conformational change that enhances the affinity of calmyrin for PS2. Thus, conformational changes in calmyrin may reduce the affinity for PS2.

Cells overexpressing calmyrin proteins capable of being myristoylated showed greater variation in staining patterns often with increased targeting of calmyrin to the cytoplasm and plasma membrane suggesting that myristoylation may be involved in this dynamic behavior. The calmyrin that localized to the cytoplasm had a reticular-like staining pattern which colocalized with PS2 staining when the two proteins were coexpressed. It is believed that the reticular staining represents targeting of calmyrin protein to the ER since it has been shown that overexpressed PS2 was localized to the nuclear envelope and ER (see Kovacs et al., 1996; Janicki and Monteiro, 1997). Interestingly, in PS2 cotransfected cells, relatively little calmyrin was present in the nucleus, and instead, the entire population almost completely colocalized with PS2 at the ER. This redistribution to the ER is consistent with the stoichiometric change of binding sites available for calmyrin once PS2 was overexpressed.

Cell death findings imply that the binding of calmyrin to PS2 is related to PS2 function in apoptosis. The current findings that coexpression of calmyrin with presenilin 2 in HeLa cells increased apoptosis suggest that the two proteins act in concert in a pathway or pathways regulating cell death. Although the pathway through which the two proteins function during programmed cell death, is unknown, the fact that calmyrin is a calcium-binding protein (Naik et al., 1997) raises some obvious possibilities. First, calmyrin may "sense" $Ca^{2+}$ changes and subsequently regulate PS2 function. Alternatively, PS2 proteins (including FAD mutants) may alter calcium homeostasis resulting in a change in calcium binding by calmyrin which could then trigger a signal transduction cascade. This latter possibility is attractive since overexpression of presenilins has been shown to cause perturbations in calcium homeostasis (Guo et al., 1996; Keller et al., 1998). It could be argued that coexpression of any calcium-binding protein with presenilins would cause increased cell death. However, this is clearly not the case as overexpression of another calcium-binding protein, calbindin D28k, suppressed the proapoptotic functions of PS (Guo et al., 1998).

Having identified and verified calmyrin as a PS2 binding partner, the next logical step was to characterize the functional role of this interaction. The structural features of calmyrin and presenilins implicated apoptotic signaling and $Ca^{2+}$ regulation as playing potential roles in the PS2/calmyrin interaction. Therefore, further experiments were performed by generating and using myristoylation-deficient and reduced $Ca^{2+}$ affinity EF-hand mutants of the calmyrin protein. Subsequently, HeLa cells overexpressing these calmyrin constructs and/or PS2 were studied to observe the effect on intracellular localization, apoptosis, and $Ca^{2+}$ responses to histamine H. Generation and Localization of Calmyrin Mutants In order to determine the roles of myristoylation and $Ca^{2+}$ binding in calmyrin function, constructs with disrupted myristoylation site and EF-hands were generated by site-directed mutagenesis according to the following procedure.

The myristoylation site on pBS-calmyrin was mutated by PCR using primers MYR I (SEQ ID NO: 20) and 2 (SEQ ID NO: 21), to change the second base in the second codon from G to C resulting in the amino acid substitution Gly to Ala, as set forth below. Mutations in the two $Ca^{2+}$-binding EF-hands were created by the QuikChange site-directed mutagenesis method (Stratagene) using the pBS-calmyrin construct with PCR primers EF(N)1 (SEQ ID NO: 21) and 2 (SEQ ID NO: 22) or EF(C)1 (SEQ ID NO: 23) and 2 (SEQ ID NO: 24) to generate, respectively, the D127N mutation by changing the first base in the codon from G to A and the E172Q mutation by changing the first base in the codon from G to C. Nucleotide substitutions were confirmed by sequencing. Expression constructs were created by digesting the mutated pBS-calmyrin with SacII and XhoI gel isolating the ~650 bp fragment, and ligating it to SacII/Sal I linearized pGEM-CMV, a CMV-driven plasmid.

Primer List

| | | |
|---|---|---|
| MYR1 | 5'GCATGTTCATGGA<u>TCCGC</u>GGGCGATGGCGGGCTCGGGCAG3'; | SEQ ID NO:19 |
| MYR2: | 5'CGAGT<u>AGCATGT</u>CGACTCACAGGACAATCTTAAA3'; | SEQ ID NO:20 |
| EF(N)1: | 5'CCTTGAACAGAGAA<u>A</u>ACCTGAGCCGGC3'; | SEQ ID NO:21 |
| EF(N)2: | 5'GCCGGCTCAGGT<u>TTT</u>CTCTGTTCAAGG3'; | SEQ ID NO:22 |

-continued

EF(C)1:  5'CCATCAACCTCTCT_C_AGTTCCAGCACG3';     SEQ ID NO:23

EF(C)2:  5'CGTGCTGGAACT_G_AGAGAGGTTGATGG3';     SEQ ID NO:24

Nucleotides that have been changed to incorporate an amino acid mutation are underlined. Restriction enzymes sites incorporated into the primers to aid in cloning are denoted by the dashed underline.

In the calmyrin-MYR mutant the penultimate N-terminal glycine at position 2 of protein SEQ ID NO: 2 (G to C at position 71 of nucleotide SEQ ID NO: 26) was changed to an alanine because a similar substitution in hippocalcin prevented cotranslational addition of myristic acid (Kobayashi et al., 1993). In the calmyrin-EF-N mutant the aspartic acid at position 127 of protein SEQ ID NO: 2 in the first intact EF-hand in calmyrin was mutated to asparagines (G to A at position 445 of nucleotide SEQ ID NO: 26). Similarly, the calmyrin-EF-C mutant had the glutamic acid at position 172 of protein SEQ ID NO: 2 in the second intact EF-hand mutated to glutamine (G to C at position 584 of nucleotide SEQ ID NO: 26). It was speculated that replacing these acidic residues with their amine counterparts could lower the affinity for $Ca^{2+}$ about 1000 fold while maintaining structural integrity. Western blots of HeLa cells overexpressing these calmyrin mutant constructs showed that the EF-C mutant was expressed to near wild type levels, while the MYR and EF-N mutants accumulated lower levels of protein (data not shown). Thus, to better determine the protein stability of these calmyrin mutants, HeLa cells were labeled with a radioactively labeled precursor according to the following technique.

$2×10^6$ HeLa cells suspended in 0.4 ml OptiMEM (GIBCO BRL) were electroporated at 960 μF and 0.3 kV with 15 μg pGEM CIB constructs. Cells were diluted into OptiMEM+FBS and plated into 6-well plates, after they attached (2–3 hrs) the media was replaced with DMEM+FBS. The following day cells were washed 2 times in met/cys deficient DMEM+FBS (filtered) and returned to 37° C. incubator for 30 minutes. Following met/cys starvation, the cells were incubated with 6 Mbq Tran $^{35}$S-LABEL(met & cys) (ICN) in 1 mL deficient media for 15 minutes, washed 2 times with chase media (deficient DMEM+15 mg/mL met+15 mg/mL cys) and returned to incubator until harvesting (0–4 hrs.) at which point cells were washed 2 times in cold PBS, collected in 100 μL Tris IP buffer (50 mM Tris, 150 mM NaCl, 2 mM EDTA, 0.25% NP40, protease inhibitors) on ice, sonicated, and centrifuged at 14,000 rpm for 10 minutes to remove any insoluble material. The 100 μL labeled lysate was incubated with 3 μL rabbit anti-calmyrin serum for 1 hr. at 4° C. Protein A-Sepharose beads (Pharmacia Biotech, Inc.) were preblocked by incubating with non-labeled HeLa lysate for 2 hrs. at 4° C., washed 3 times in Tris IP buffer, and resuspended as 1:1 slurry. 50 μL of the slurry were added to the lysate+anti-calmyrin and incubated 2 hrs. on rocker at 4° C. The beads were pelleted by centrifugation, washed 4 times in Tris IP buffer, resuspended in Laemmli buffer and the immunoprecipitated proteins were separated by SDS-PAGE. After Coomassie blue staining and destaining, the gel was dried, exposed to film by autoradiography and/or exposed to a phosphor screen (Molecular Dynamics) for quantification of $^{35}$S labeled calmyrin protein.

Figure 28:
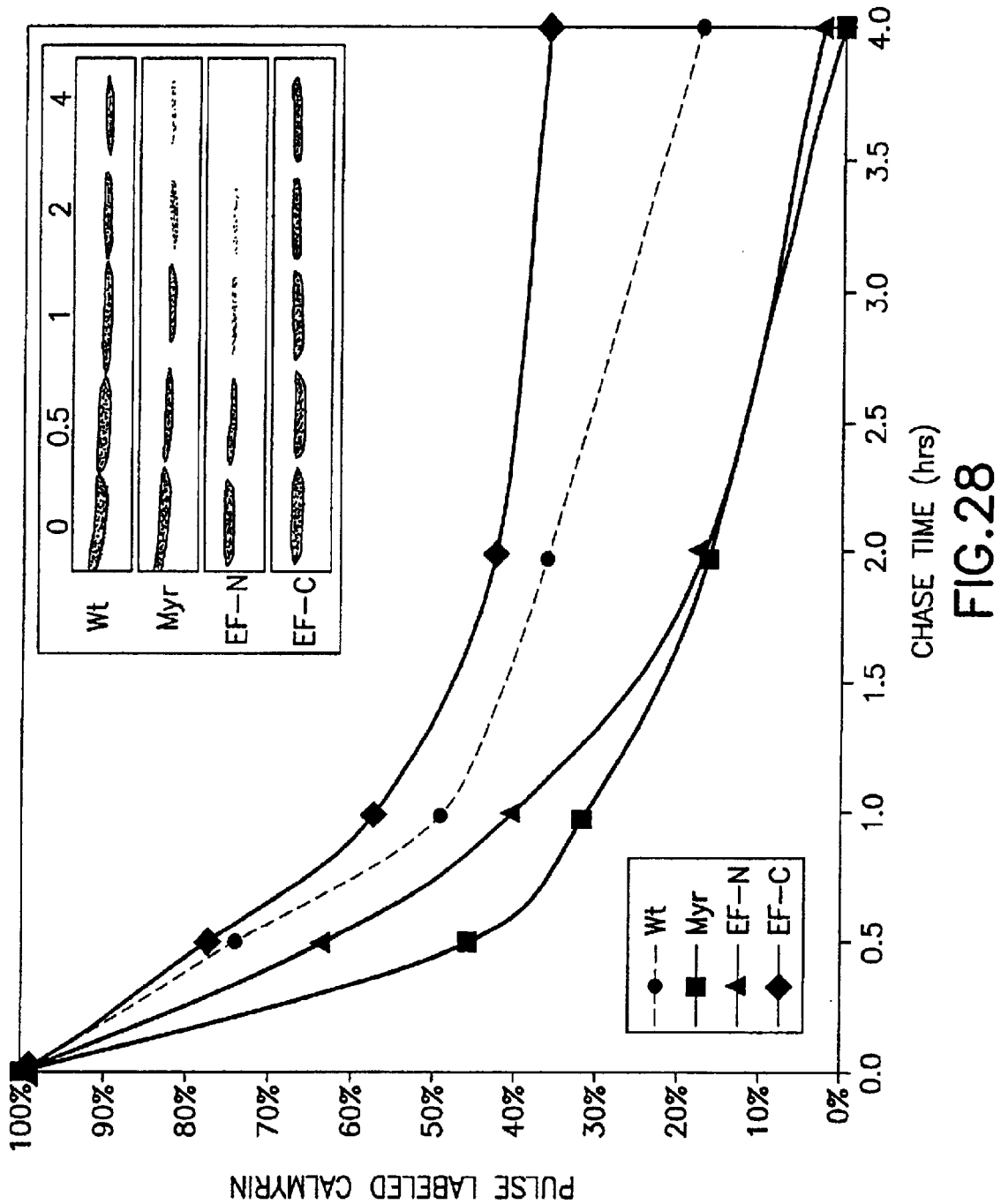
FIG. 28 is a graph illustrating protein stability of wild type and mutant calmyrin. The percentage of labeled calmyrin remaining after various chase times is plotted and indicates that preventing myristoylation and disrupting the central EF-hand reduces the half-life of calmyrin.

Lysates from $^{35}$S methione/cysteine pulse labeled HeLa cells overexpressing these three mutants or wild type calmyrin were immunoprecipitated with anti-calmyrin antibodies (FIG. 28). As seen previously, all three mutant proteins were successfully expressed, however, preventing myristoylation reduced the half-life from 60 minutes to 30 minutes. Disrupting the N-terminal EF-hand also reduced the half-life to 50 minutes, while disrupting the C-terminal EF-hand actually increased the half-life to 90 minutes. The successful generation and expression of these mutants allowed further study to determine the effect of the myristic acid and $Ca^{2+}$-binding on the localization and function of calmyrin.

Figure 29:
FIGS. 29–33 show immunofluorescent localization of wild type and mutant calmyrin proteins in HeLa cells.
Figure 30:
Figure 31:
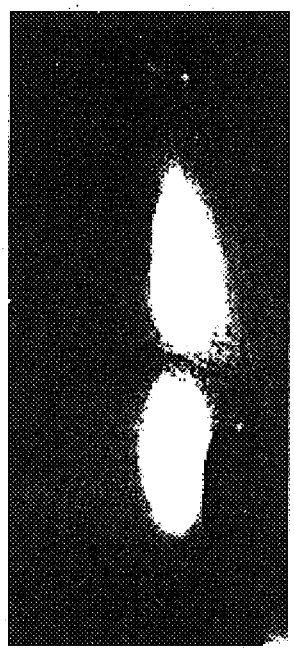
Figure 32:
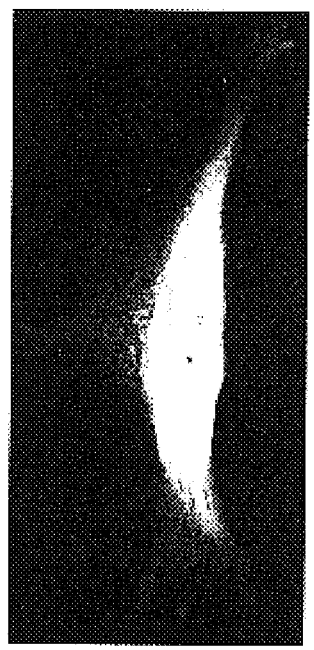
Figure 33:

HeLa cells overexpressing the calmyrin MYR and EF-mutants were immunofluorescent stained to confirm expression and to observe the effect these mutations had on the subcellular localization of calmyrin. In comparison to the low level endogenous and overexpressed wild type calmyrin (FIG. 29 and 30), overexpression of the MYR mutant shows significantly increased accumulation in the nucleus and more diffuse cytoplasmic staining (FIG. 31). The localization of this non-myristoylated calmyrin mutant was reminiscent of the staining found previously with a calmyrin construct that was myc tagged at its amino terminus, and hence also defective in myristoylation. In contrast, overexpression of the EF-C and EF-N mutants produced the inverse pattern of reduced nuclear localization and increased ER staining (FIG. 32 and 33). These results indicate that the presence of the myristic acid on calmyrin is essential for ER targeting, whereas, a reduced affinity for $Ca^{2+}$ does not hinder the localization of the protein to the ER.

I. Overexpression of Calmyrin Influences Apoptosis

As shown above, FIG. 34 shows that a subset (⅔) of cells overexpressing PS2 appeared apoptotic according to both CytoDEATH positive staining and condensed nuclei. Similarly, when calmyrin was overexpressed, analogous apoptosis was observed (FIG. 35). Cotransfection of PS2 and calmyrin induced even higher apoptosis. Fields of cells overexpressing calmyrin or PS2 individually showed levels of apoptosis above the neurofilament background, but less than that produced by the coexpressers.

In light of the fact that CytoDEATH labeling on coverslips only captured a narrow time "window" of cells undergoing apoptosis, the total amount of cell death accumulated over time was quantified by counting the total number of floating cells in the media after transfection with various amounts of plasmid DNAs encoding calmyrin and PS2. This simple method was more reliable in quantifying cell death.

Figure 40:
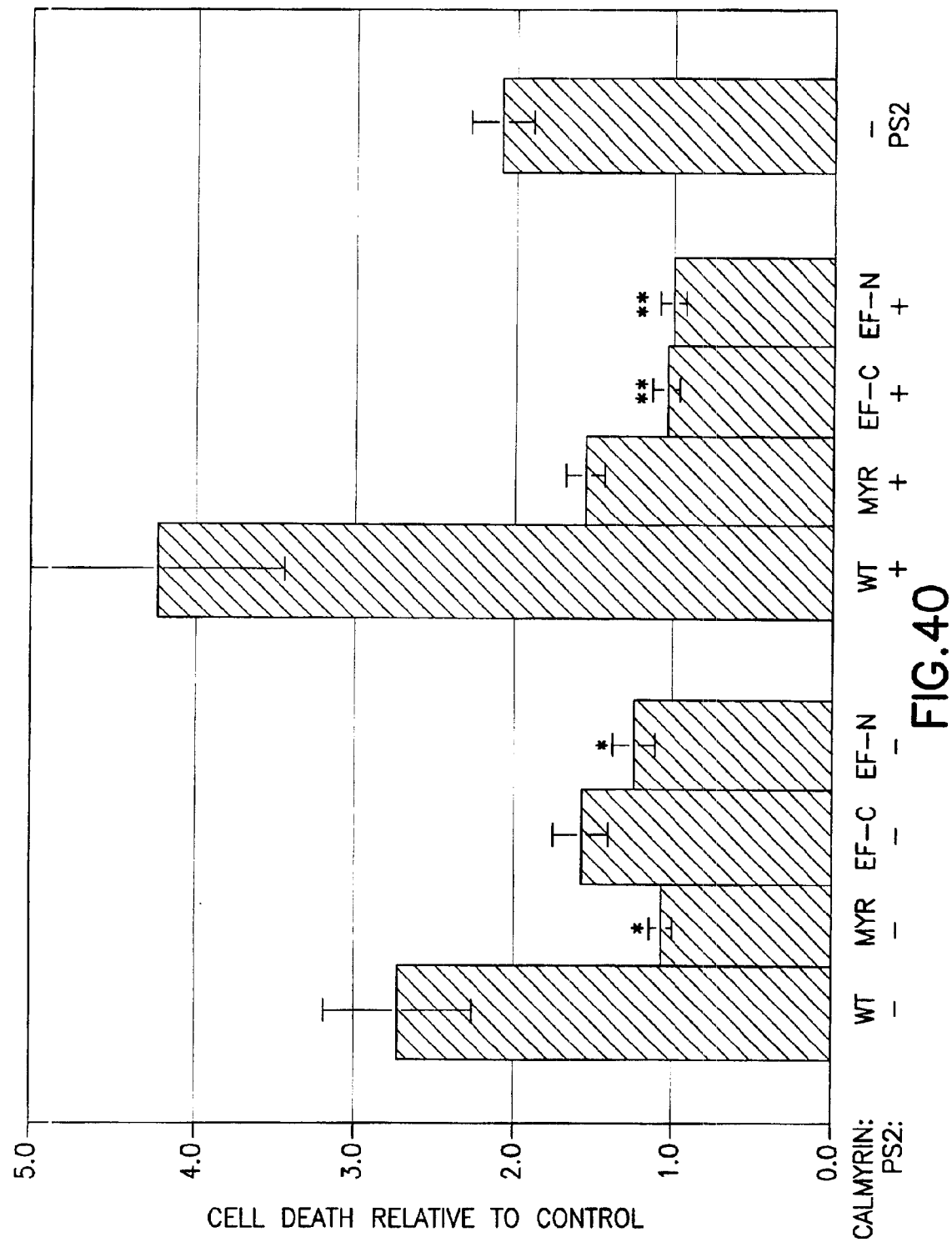
FIG. 40 is a graph quantifying cell death due to overexpression of calmyrin mutants.

This method was also used to quantify the cell death caused by overexpressing mutant calmyrin (FIG. 40). When expressed individually, all three calmyrin mutants failed to induce cell death at the levels seen with wild type calmyrin. Myristoylation-deficient calmyrin did not alter cell death from background levels and the mean of 1.04 was significantly less than the 2.73 fold increase of wild type (p-value=0.020). While both $Ca^{2+}$-binding EF-hand mutants produced less than wild type death, only EF-N (mean=1.23, p-value=0.030) reached significance. The 1.55 fold increase in death with the more stable EF-C mutant was intermediate between background and fully functional calmyrin levels. This data argues that disrupting $Ca^{2+}$ binding and especially myristoylation reduces the ability of calmyrin to cause cell death. An even more interesting effect on cell death emerged when the mutant calmyrin was cotransfected with PS2. Whereas, coexpression of wild type calmyrin with PS2 increased cell death additively (seen in both FIG. 39 and FIG. 40), coexpression of each of the three calmyrin mutants with PS2 decreased cell death below the 2.09 level seen with PS2 alone. When compared to PS2, the decrease in cell death from the coexpression of the EF-hand mutants reached statistically significance, EF-C mean=1.05 (p-value=0.006) and EF-N mean=1.00 (p-value=0.005). It is especially remarkable that cell death returned to control levels with the coexpression of PS2 and EF-C, two proteins that individually increase cell death 2.1 fold and 1.6 fold respectively. This unanticipated result suggests that the mutant calmyrin interferes with PS2 induced cell death, further indicating that these two proteins interact in a functionally significant manner. Thus, therapeutic treatment that includes introduction of a mutant calmyrin protein to compete with the wild-type calmyrin protein would affect and reduce apoptosis.

J. Overexpression of Calmyrin Alters Histamine Induced $Ca^{2+}$ Oscillations

Because the presenilins have been implicated in $Ca^{2+}$ regulation and calmyrin is a $Ca^{2+}$-binding protein, intracellular $Ca^{2+}$ imaging using Fura-2 was performed on HeLa cells overexpressing wild type and mutant calmyrin or the presenilins. Briefly, $Ca^{2+}$ imaging with Fura was performed according to the following regime.

$2\times10^6$ HeLa cells suspended in 0.4 ml OptiMEM were electroporated at 960 $\mu$F and 0.3 kV with 15 $\mu$g pGEM CIB or PS constructs and 3 $\mu$g pDsRed1-Mito (CLONTECH). Cells were diluted into OptiMEM+FBS(heat inactivated) and plated onto 25 mm circle glass coverslips, after they attached (2–3 hrs.) the media was changed back to DMEM+FBS(heat inactivated). 12–24 hrs. post-electroporation coverslips were gently washed 3 times in HBS (20 mM HEPES, 140 mM NaCl, 5.0 mM KCl, 0.7 mM $N_2HPO_{04}$, 6.0 mM glucose), loaded with cell permeant 1 $\mu$M fura-2-AM (Molecular Probes) in HBS+Ca (HBS with 1.8 mM $CaCl_2$, 1.0 mM $MgCl_2$) for 20 min. at RT, washed very gently 2 times with HBS+Ca, and incubated 10–30 min. before beginning capture at 2 second intervals for 2 minutes with 500 uM histamine added 5 seconds into capture sequence. Alternatively, for imaging in $Ca^{2+}$ free buffer, after the loading/washing/incubation in HBS+Ca the cells were washed 2 times with HBS-Ca (HBS with 10 $\mu$M EGTA, 1.0 mM $MgCl_2$) and incubated exactly 3 min. before beginning capture sequence with histamine. Fields with a high percentage of red fluorescing cells were selected for imaging on a Zeiss Axiovert 135 inverted microscope (40× objective) coupled to the C-Imaging system (Compix, Mars, Pa.). Cytosouce $Ca^{2+}$ fluctuations are plotted as the ratio of the 510 nm emissions produced by excitations at 340 nm ($Ca^{2+}$ bound) and 380 nm ($Ca^{2+}$ unbound) for each individual red fluorescing cell in a selected field from a minimum of three different coverslips/stimulations. The mean fura ratios at field 2, field 60, and the peak at fields 6–8 were calculated and graphed on excel with standard errors shown. ANOVA and Scheffe's F post hoc analysis (StatView) were performed to determine significance.

To identify live cells that were successfully expressing transiently transfected constructs, a red fluorescent protein (RFP) marker, pDsRed1-Mito, was included in all electroporations at a 1:5 ratio with the calmyrin or PS constructs. Approximately 70–85% of the red fluorescing cells also expressed high levels of their cotransfected calmyrin or PS construct according to immunofluorescent staining after fixation (data not shown).

Figure 41:
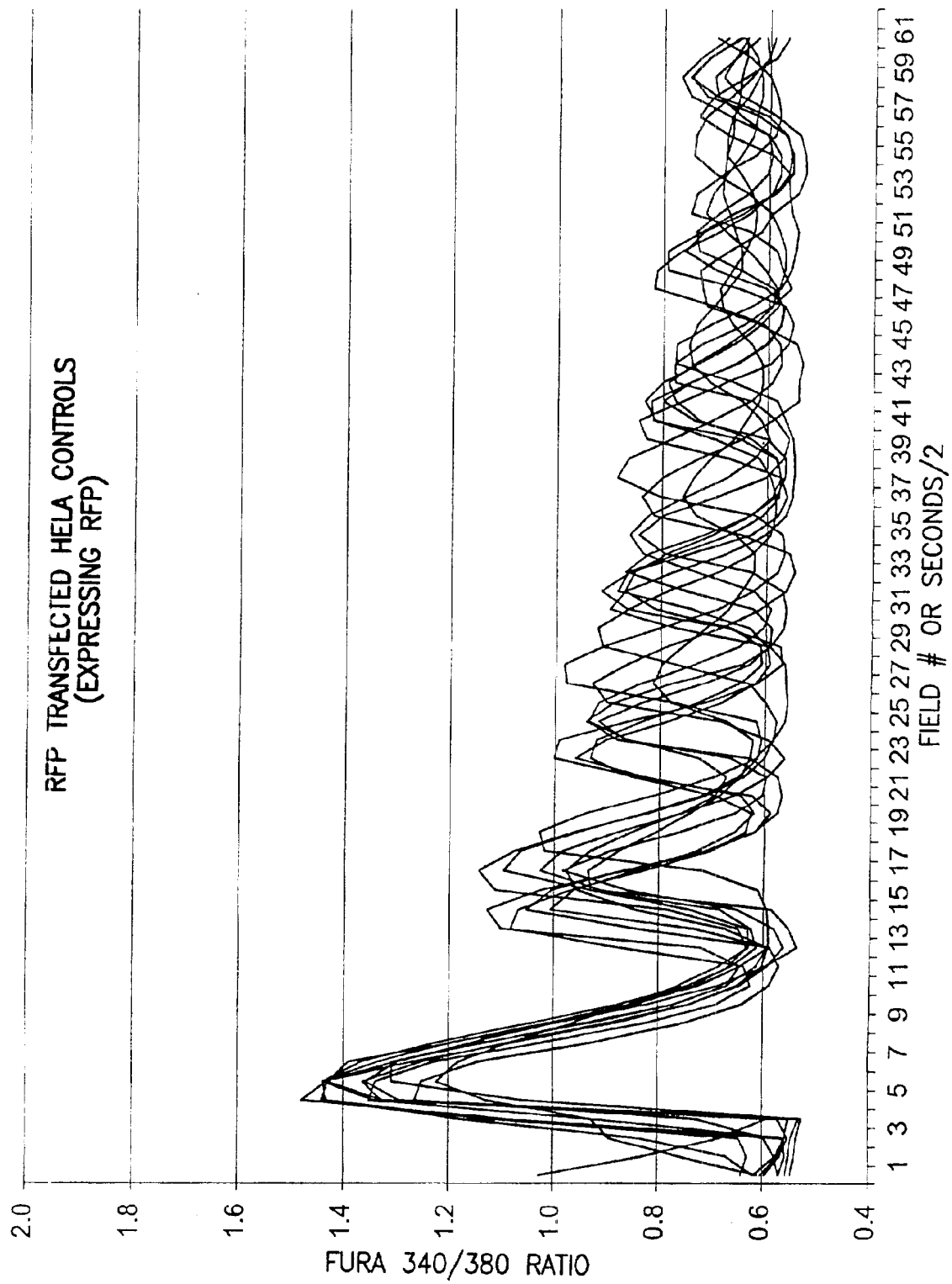
FIGS. 41–42 show $Ca^{2+}$ imaging of histamine induced oscillations in RFP-marker transfected HeLa cell controls, with graph A showing individual cells expressing RFP and graph B showing individual cells not expressing RFP.
Figure 42:
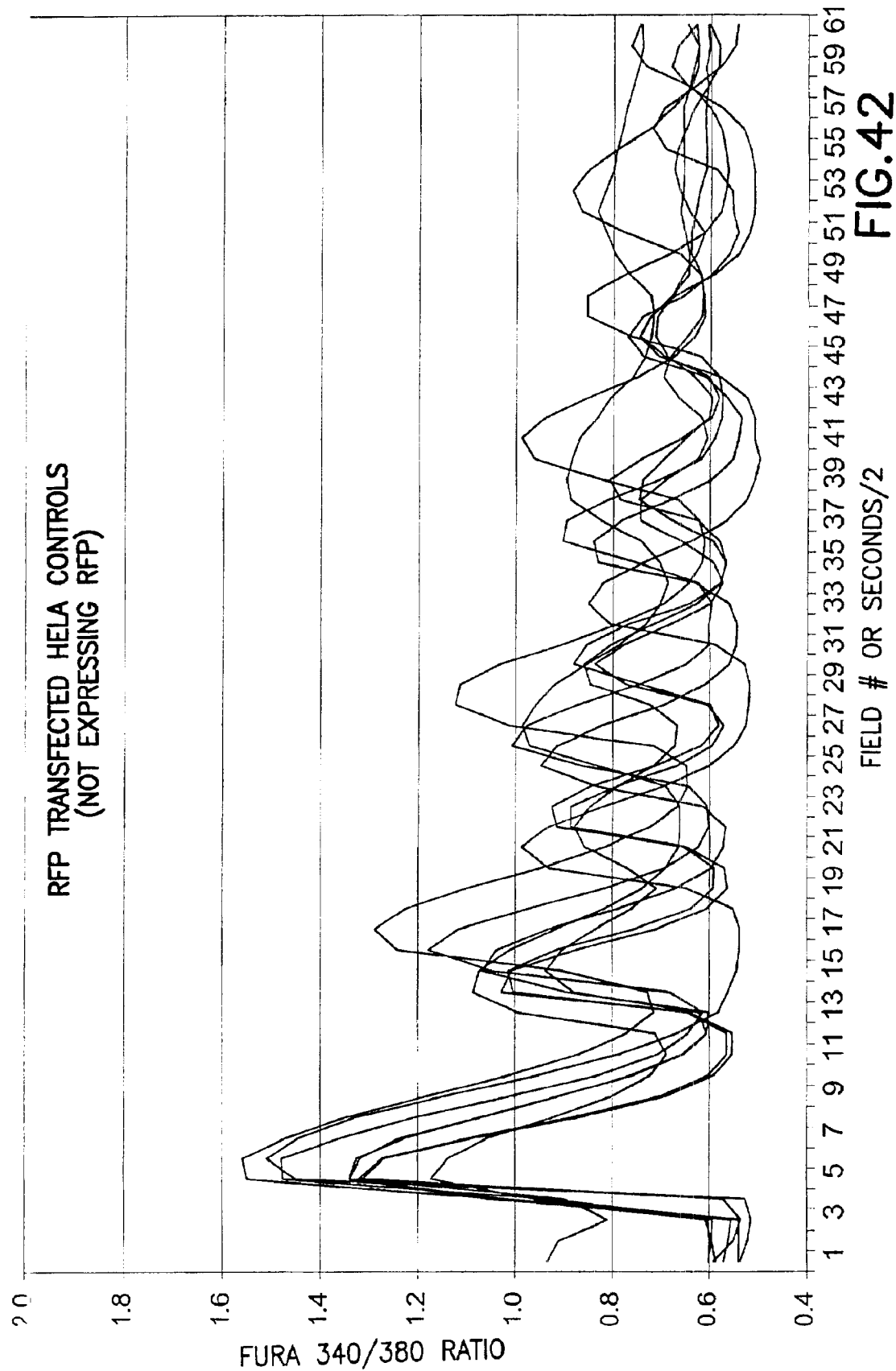
Figure 43:
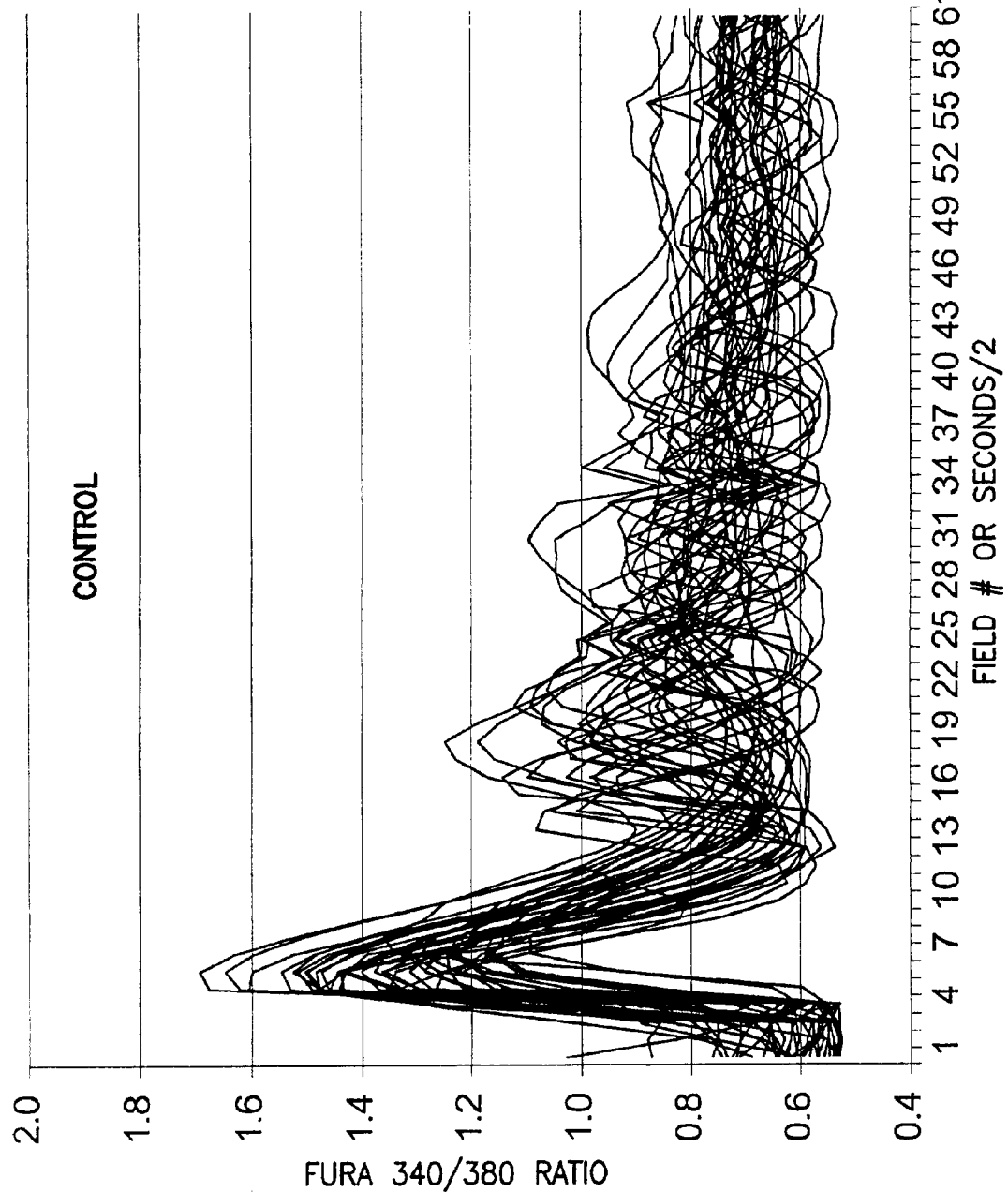
FIGS. 43–44 show the effects of calmyrin overexpression on histamine induced $Ca^{2+}$ release in HeLa cells, with graph A showing individual control cells and graph B showing individual calmyrin transfected cells.
Figure 44:
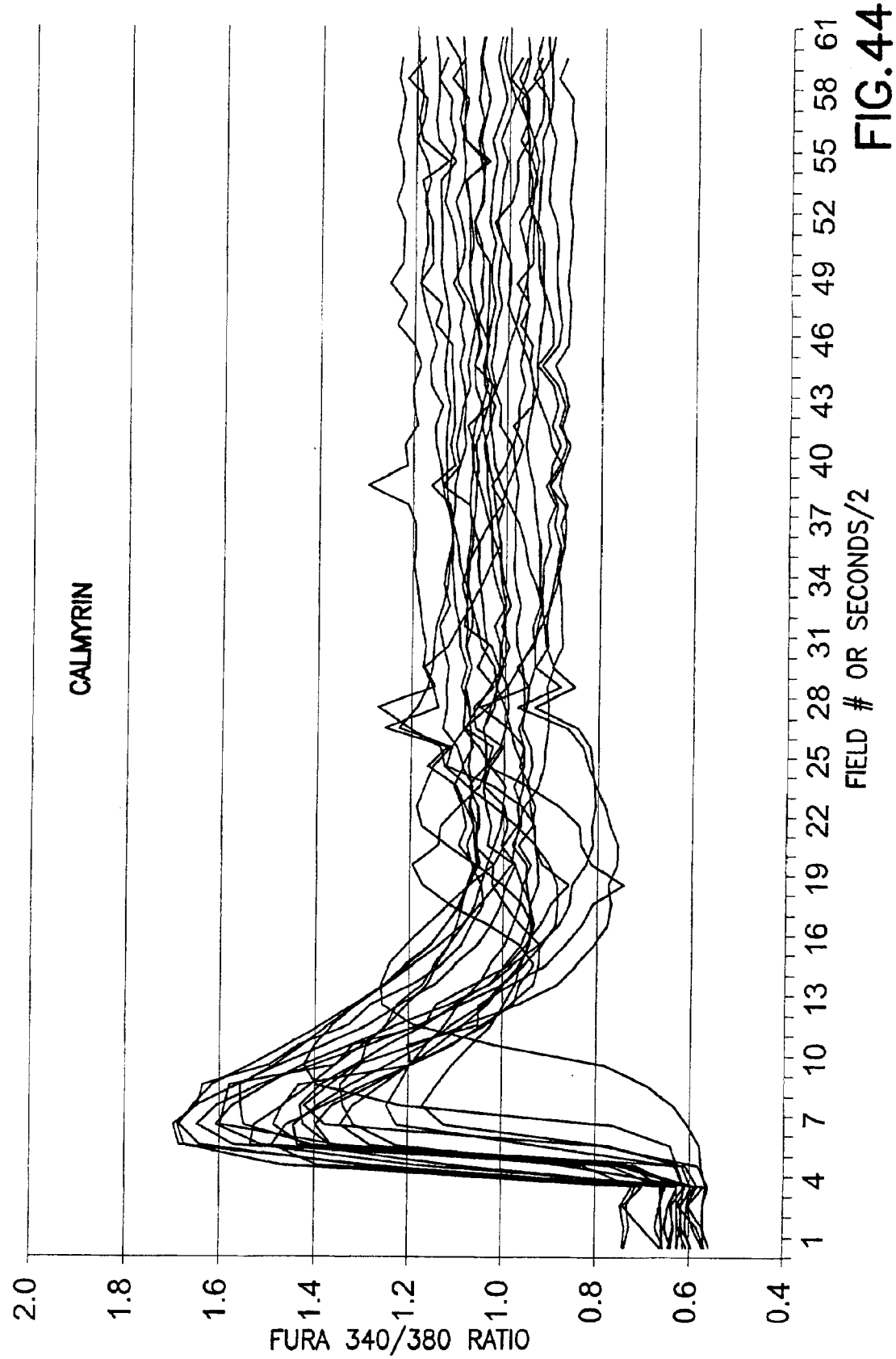
Figure 45:
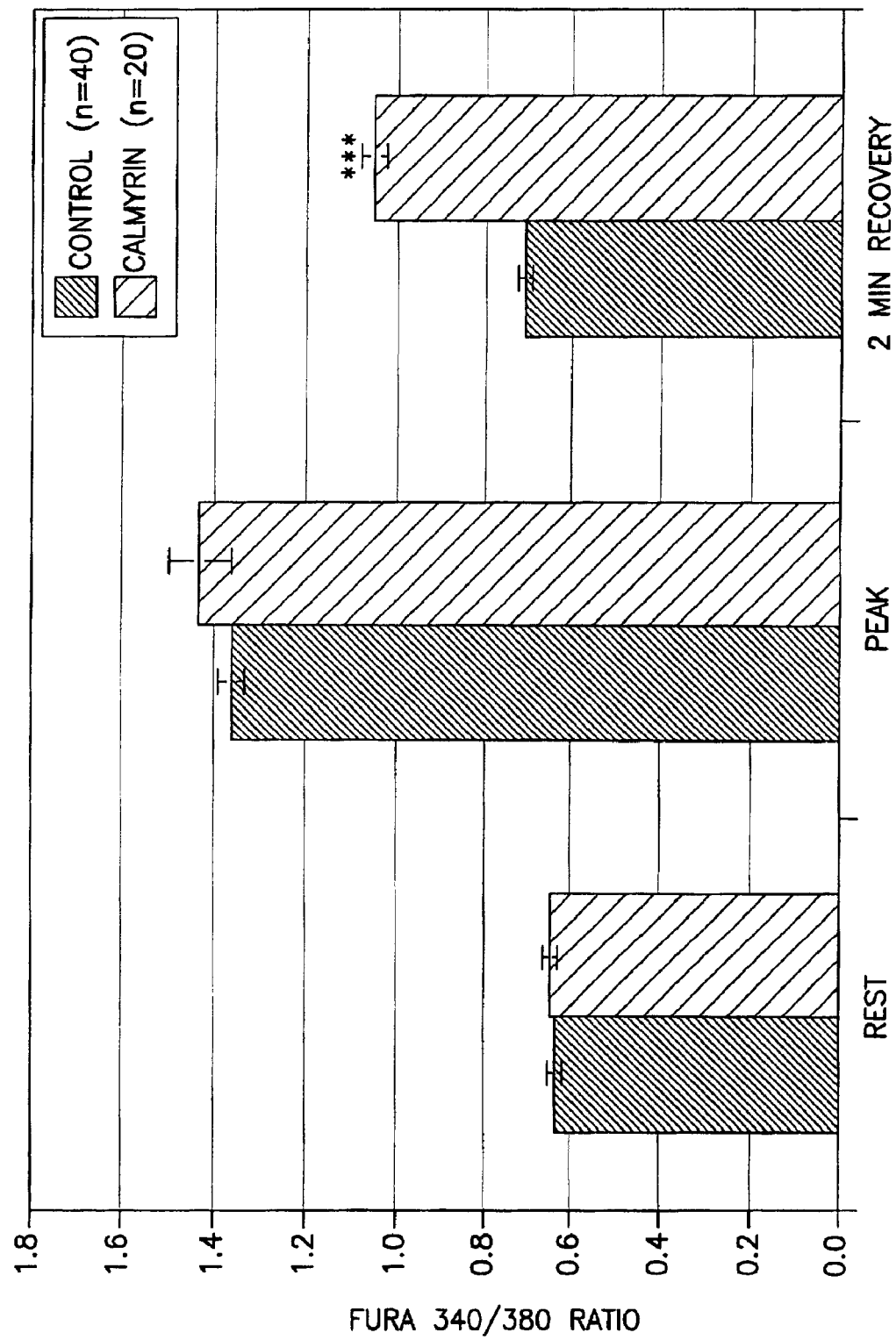
FIG. 45 is a graph showing resting, peak and recovery $Ca^{2+}$ levels in HeLa cells overexpressing calmyrin.
Figure 46:
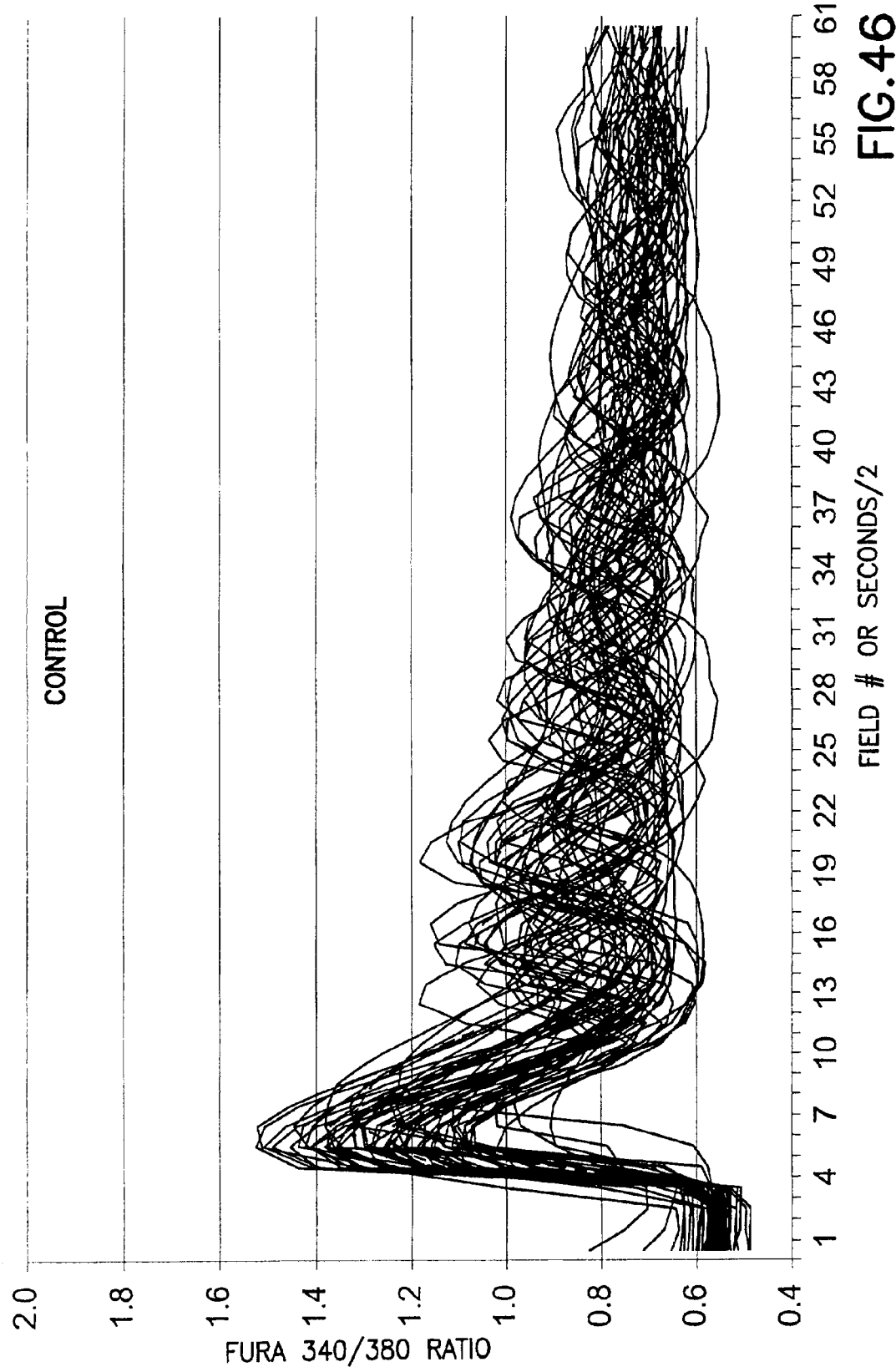
FIGS. 46–47 show the effects of unmyristoylated mutant calmyrin overexpression on histamine induced $Ca^{2+}$ release in HeLa cells, with graph A showing individual controls transfected cells and graph B showing individual calmyrin MYR mutant transfected cells.
Figure 47:
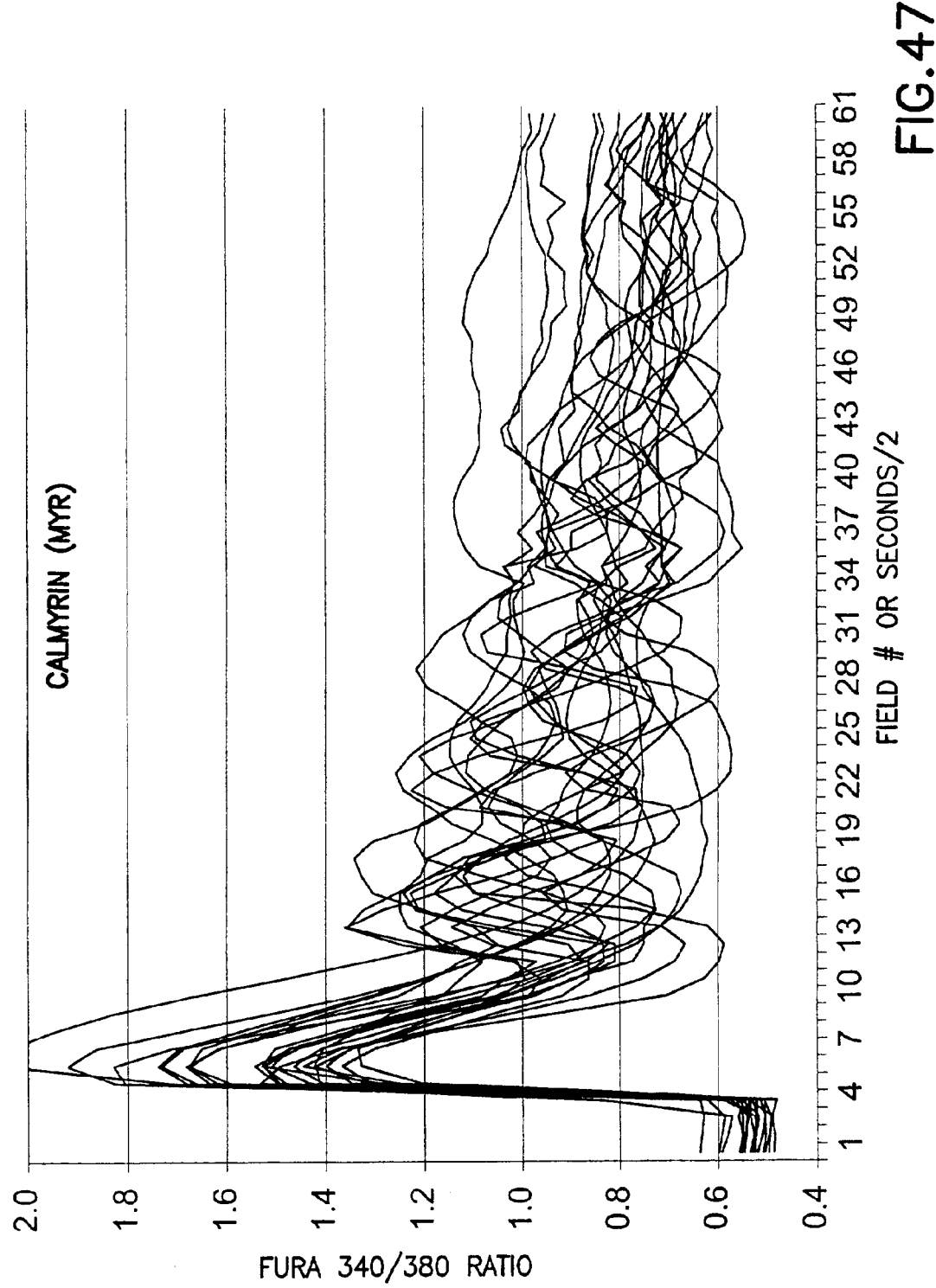
Figure 48:
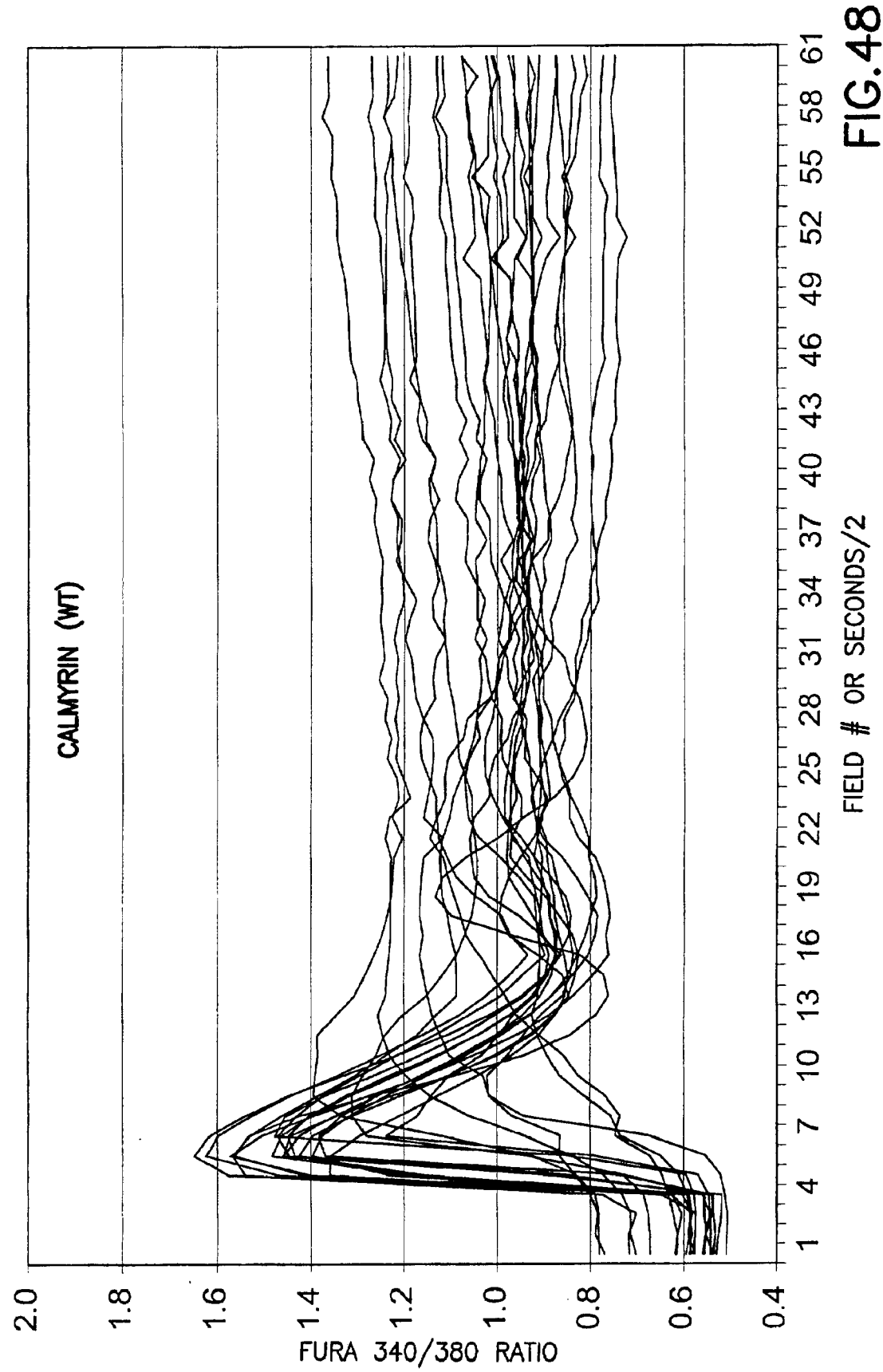
FIGS. 48–49 show the effects of EF-hand mutated calmyrin overexpression on histamine induced $Ca^{2+}$ release in HeLa cells, with graph A showing individual wild type calmyrin and graph B showing individual calmyrin EF-C mutant transfected cells.
Figure 49:
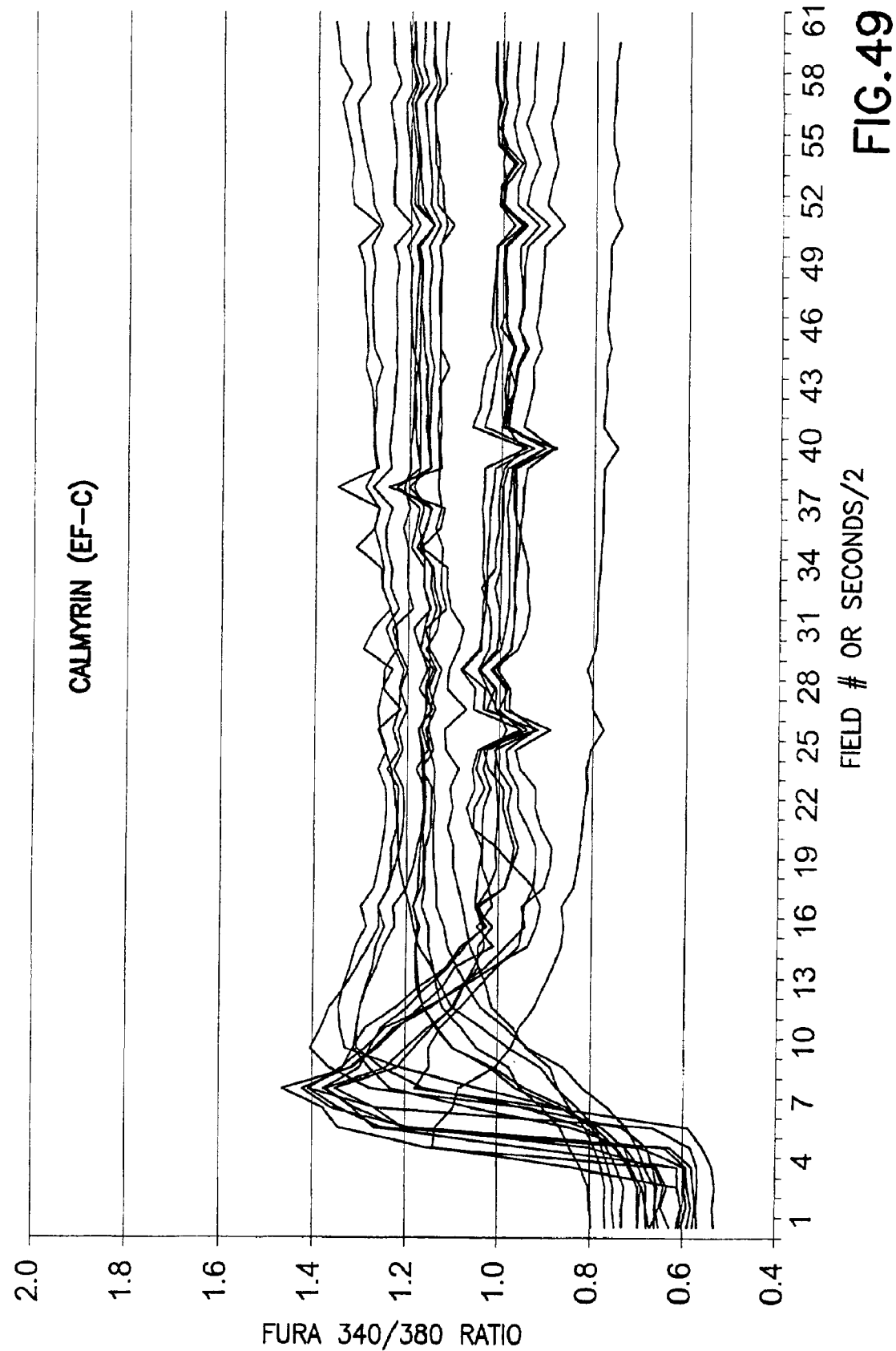
Figure 50:
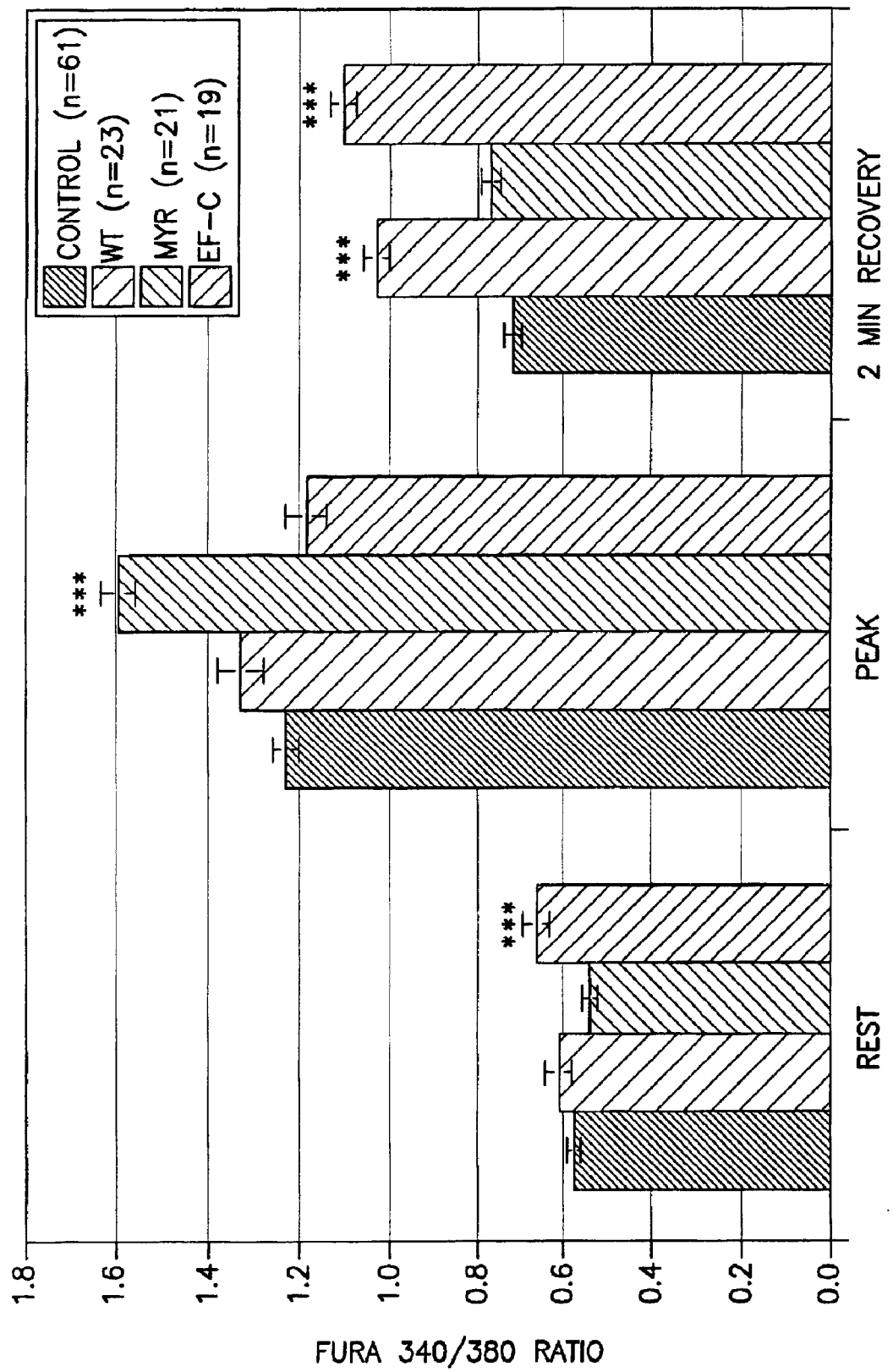
FIG. 50 shows resting, peak, and recovery $Ca^{2+}$ levels in HeLa cells overexpressing calmyrin mutants.

Histamine is known to induce $Ca^{2+}$ oscillations in HeLa cells via $InsP_3$ production. FIG. 41 shows the $Ca^{2+}$ oscillation pattern in individual red fluorescing cells in a field of HeLa controls (i.e. transfected only with the RFP marker) induced by 500 $\mu$M histamine observed for 2 minutes in a $Ca^{2+}$ free buffer containing 10 $\mu$M EGTA. In this example, all the cells displayed an oscillatory response with a frequency of approximately 3/minute and peak amplitudes that decreased with time. It is worth noting that the non-fluorescing cells from this same field (FIG. 42) or from mock transfections (data not shown) showed an analogous oscillatory pattern, indicating that this RFP (emission max at 583 nm) marker does not alter the $Ca^{2+}$ signaling or its detection. For all the subsequent $Ca^{2+}$ imaging, measurements were collected for only the 'marked' red fluorescing cells. FIGS. 43–44 show the $Ca^{2+}$ response to 500 mM histamine in $Ca^{2+}$-free buffer of control (43) and calmyrin (44) HeLa cells from several independent fields and stimulations. In the majority of controls, histamine induced $Ca^{2+}$ oscillations that returned to near baseline by 2 minutes. In contrast few, if any, cells transfected with calmyrin produced $Ca^{2+}$ oscillations, and furthermore, they maintained elevated $Ca^{2+}$ levels after 2 minutes. The mean fura ratios at rest (field 2), peak (field 6–8), and 2 minutes (field 60) for control versus calmyrin cells are graphed in FIG. 45. While the resting $Ca^{2+}$ and peak $Ca^{2+}$ release did not vary between control and calmyrin cells, the cytosolic $Ca^{2+}$ remained significantly elevated at 2 minutes in the calmyrin cells (1.04 vs. 0.70, p-value<0.0001). Clearly, overexpression of calmyrin perturbs the proper regulation of cytosolic $Ca^{2+}$. Next, the $Ca^{2+}$ response to histamine was examined in HeLa cells overexpressing the unmyristoylated calmyrin-MYR mutant and the $Ca^{2+}$-binding EF-hand calmyrin-EF-C mutant. FIGS. 46–47 show the $Ca^{2+}$ response to 500 mM histamine in $Ca^{2+}$-free buffer of control (46) and calmyrin-MYR (47) cells, FIG. 17 shows the $Ca^{2+}$ response of wild-type calmyrin (46) and calmyrin-EF-C (47) cells, and FIG. 50 plots this data as mean resting, peak, and recovery $Ca^{2+}$. The overall response patterns in the MYR mutants appear similar to the control cells such that most MYR cells oscillate at a frequency of 2–3/minute with $Ca^{2+}$ levels returning to near baseline by 2 minutes (0.76 vs. 0.71 for control). The only significant difference between MYR and control is the increased mean value at the peak of $Ca^{2+}$ release (1.58 vs. 1.21, p-value<0.0001). These results suggest that disrupting myristoylation severely cripples the function of calmyrin in altering $Ca^{2+}$ regulation after histamine stimulation, although a more subtle effect may still linger. Quite opposite to the MYR mutant, the EF-C mutant produces a non-oscillatory $Ca^{2+}$ response that mimics those seen in wild type calmyrin. At 2 minutes after stimulation these EF-C cells show sustained cytosolic $Ca^{2+}$ at levels (1.09) comparable to wild type calmyrin (1.01). Additionally, in this set of experiments a proportion (~¼) of the wild type and EF-C mutant calmyrin cells exhibited a delayed and more gradual rise in cytosolic $Ca^{2+}$ after stimulation with histamine. Thus, with regard to calmyrin's effect on histamine induced $Ca^{2+}$ responses in HeLa cells, myristoylations is required for the effect whereas reduction in $Ca^{2+}$ binding due to mutation of the C-terminal EF-hand is less disruptive.

Figure 51:
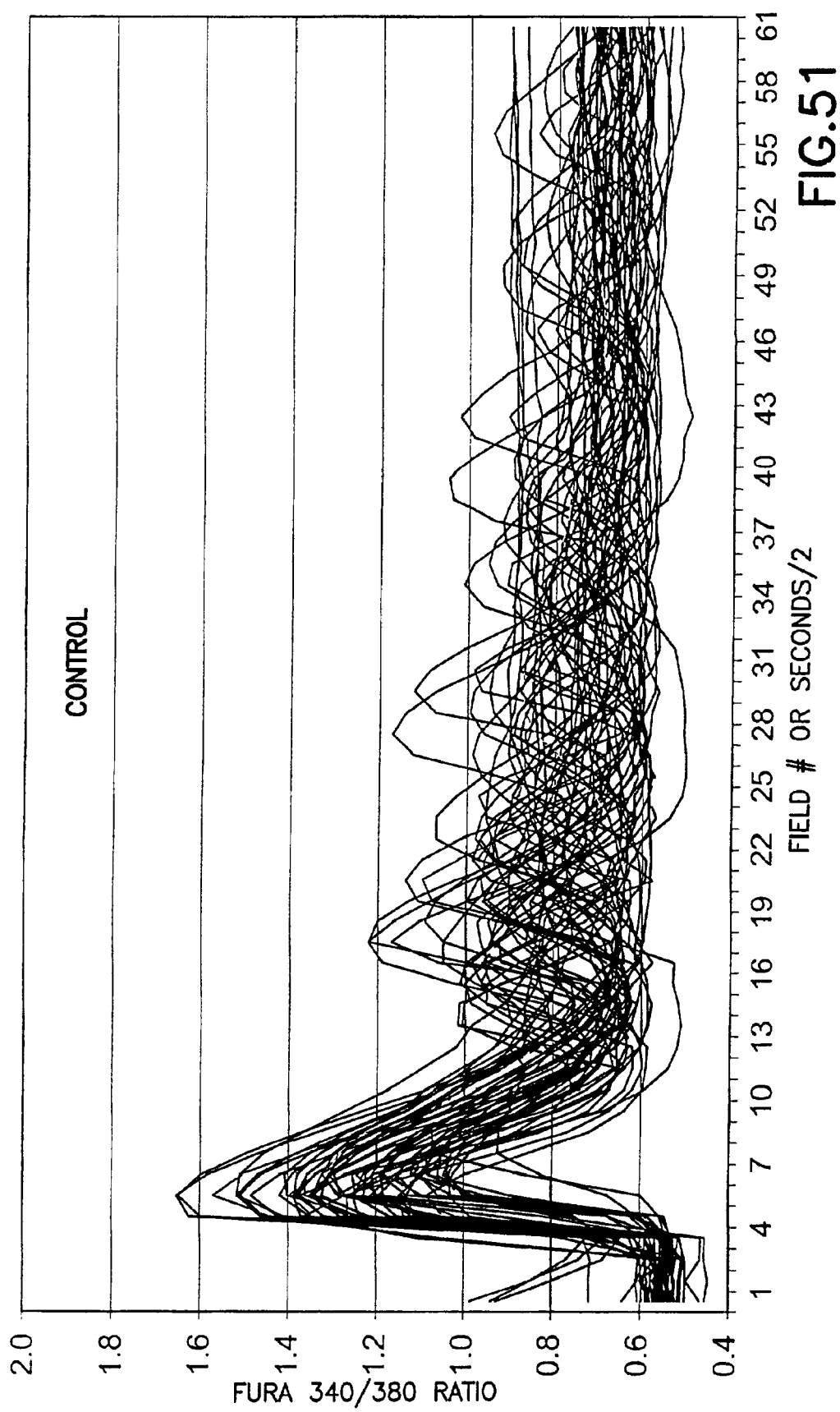
FIGS. 51–53 show the effects of presenilin overexpression on histamine induced $Ca^{2+}$ release in HeLa cells, with graph A showing individual control transfected cells, graph B showing individual PS1 transfected cells and C showing individual PS2 transfected cells.
Figure 52:
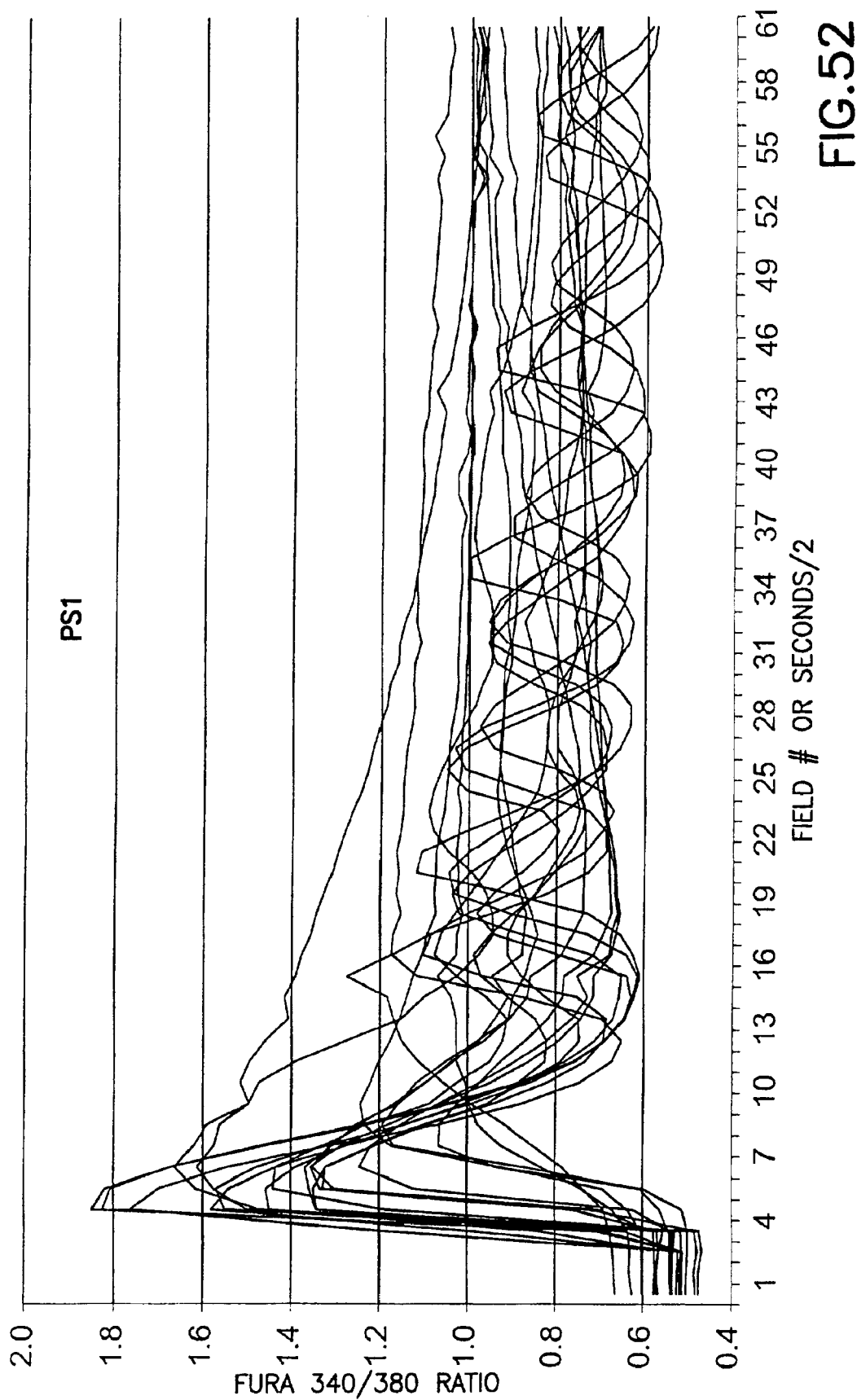
Figure 53:
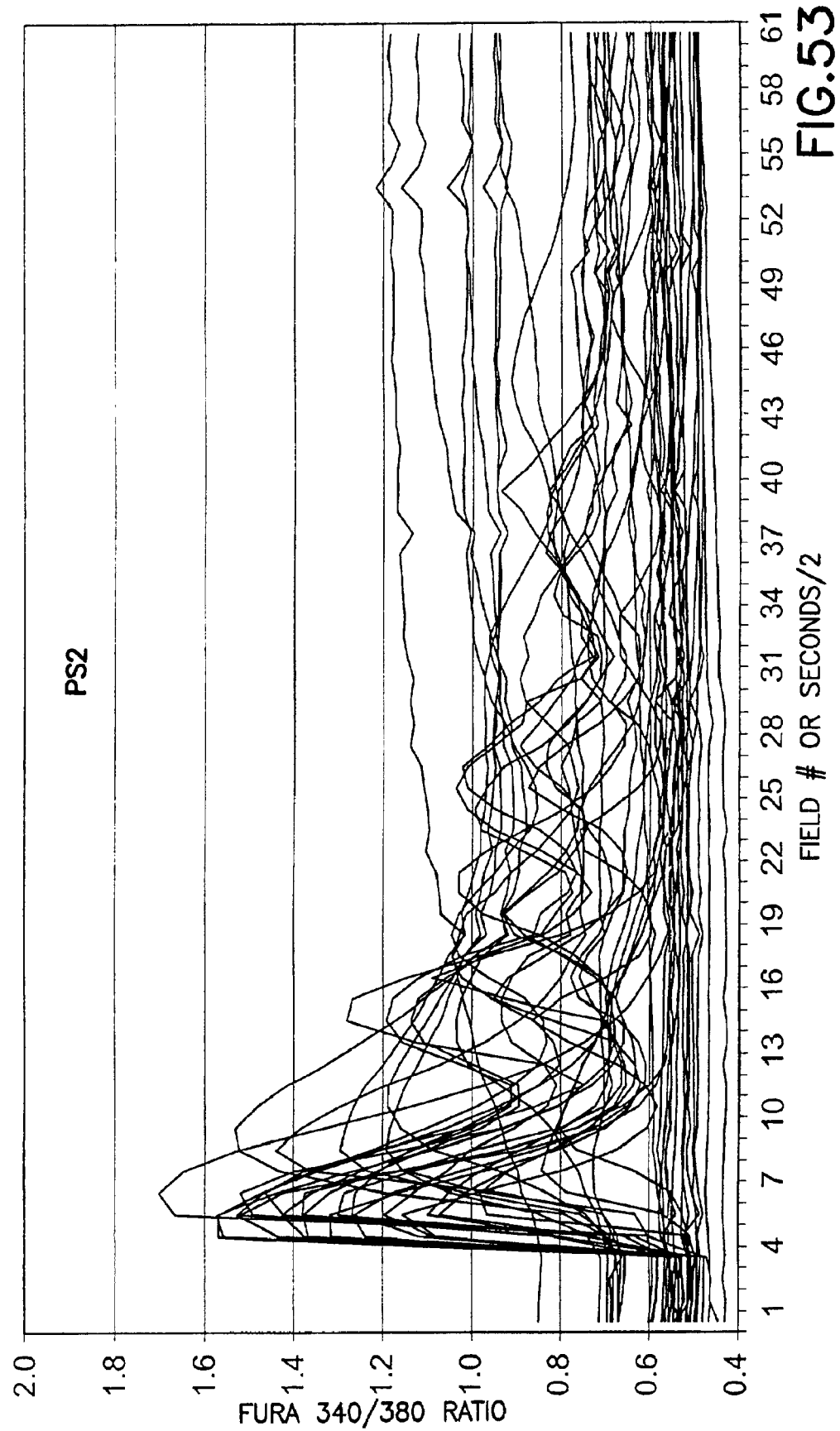
Figure 54:
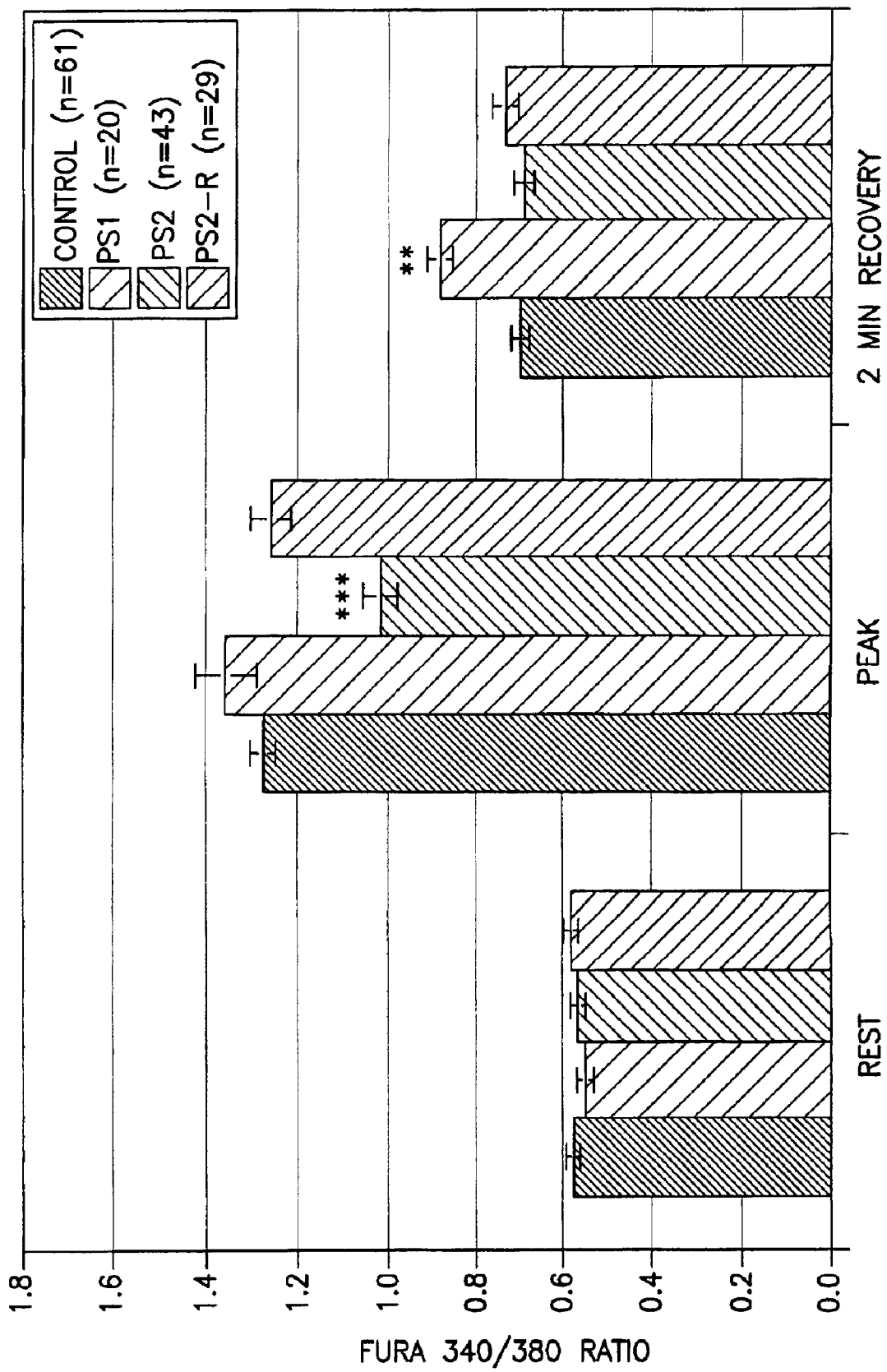
FIG. 54 show resting, peak, and recovery $Ca^{2+}$ levels in HeLa cells overexpressing the presenilins.

Analogous experiments were performed in HeLa cells overexpressing PS1 and PS2. FIGS. 51–52 show the $Ca^{2+}$ response to 500 mM histamine in $Ca^{2+}$-free buffer of control (51), PS1 (52), and PS2 (53) cells. Compared to control, the PS1 and PS2 cells demonstrated less uniformity in their responses with fewer than half of the cells oscillating. Additionally, the PS2 transfected cells had a unique pattern with over ⅓ of the cells failing to release any $Ca^{2+}$ following the addition of histamine. FIG. 54 graphs the resting, peak, and recovery means for control, PS1, PS2, and PS-R, the subset of PS2 cells that responded to histamine (i.e. the cells that never increased their $Ca^{2+}$ above baseline were excluded). Overexpression of PS1 did not alter resting cytosolic $Ca^{2+}$ or the mean peak of $Ca^{2+}$ release, but on average, $Ca^{2+}$ remained higher at 2 minutes (0.83 vs. 0.69, p-value=0.004). In the total sample of PS2 cells, the resting $Ca^{2+}$ and recovery $Ca^{2+}$ means were not altered from controls, however the mean of the peak dropped (1.00 vs. 1.26, p-value<0.0001). When only the histamine responsive cells (PS2-R) were averaged, the mean peak of $Ca^{2+}$ release increased to 1.25, demonstrating that the total PS2 average was skewed due to the low values from the non-responders. It is interesting that overexpression of PS2 (but not PS1 or calmyrin) can completely prevent the release of $Ca^{2+}$ after addition of 500 $\mu$M histamine.

Figure 55:
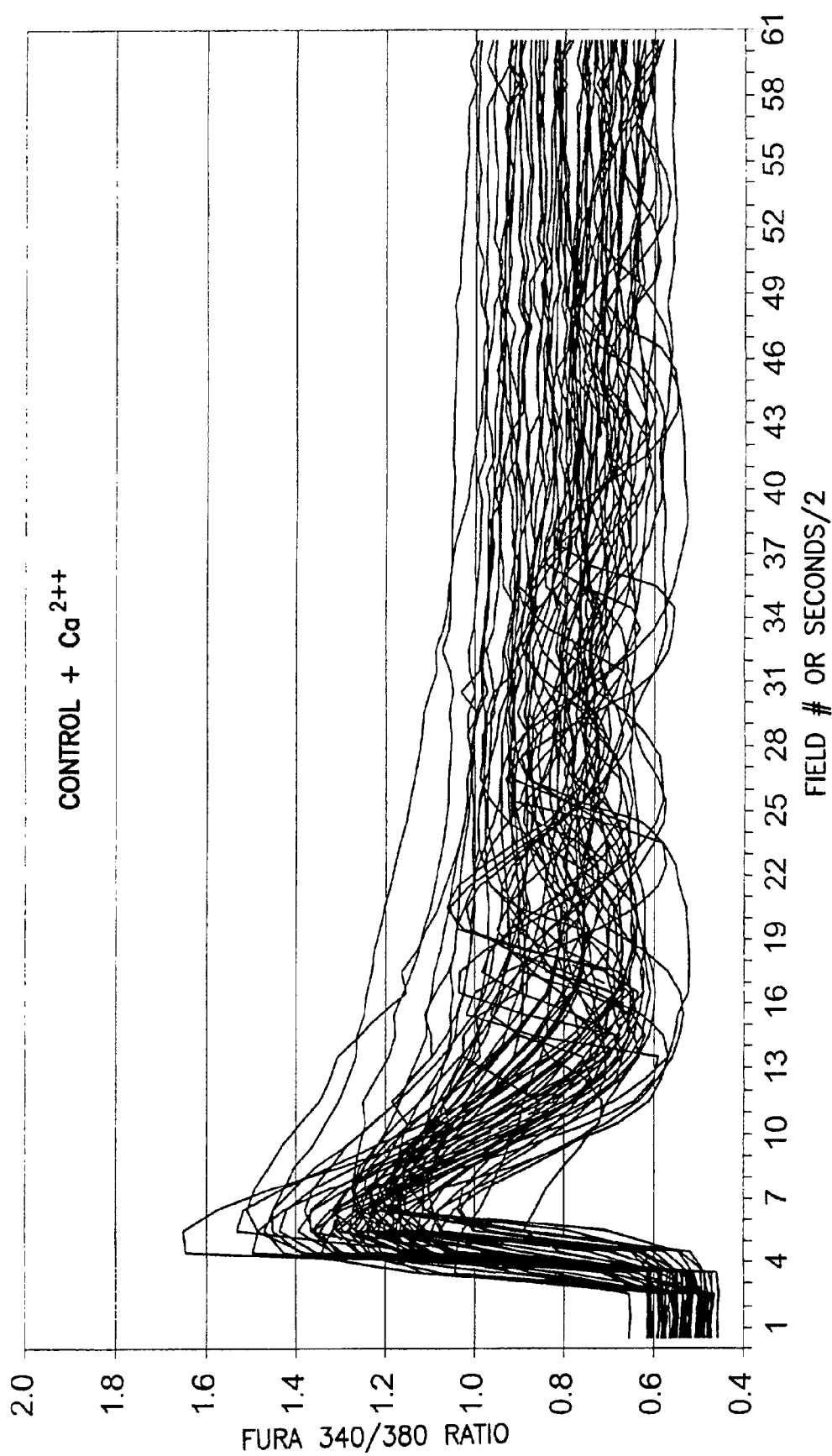
FIGS. 55–57 show the effects of calmyrin or PS2 overexpression on HeLa cell histamine induced $Ca^{2+}$ signaling in $Ca^{2+}$ containing buffer, with graph A showing individual control transfected cells, graph B showing individual calmyrin transfected cells and graph C showing individual PS2 transfected cells.
Figure 56:
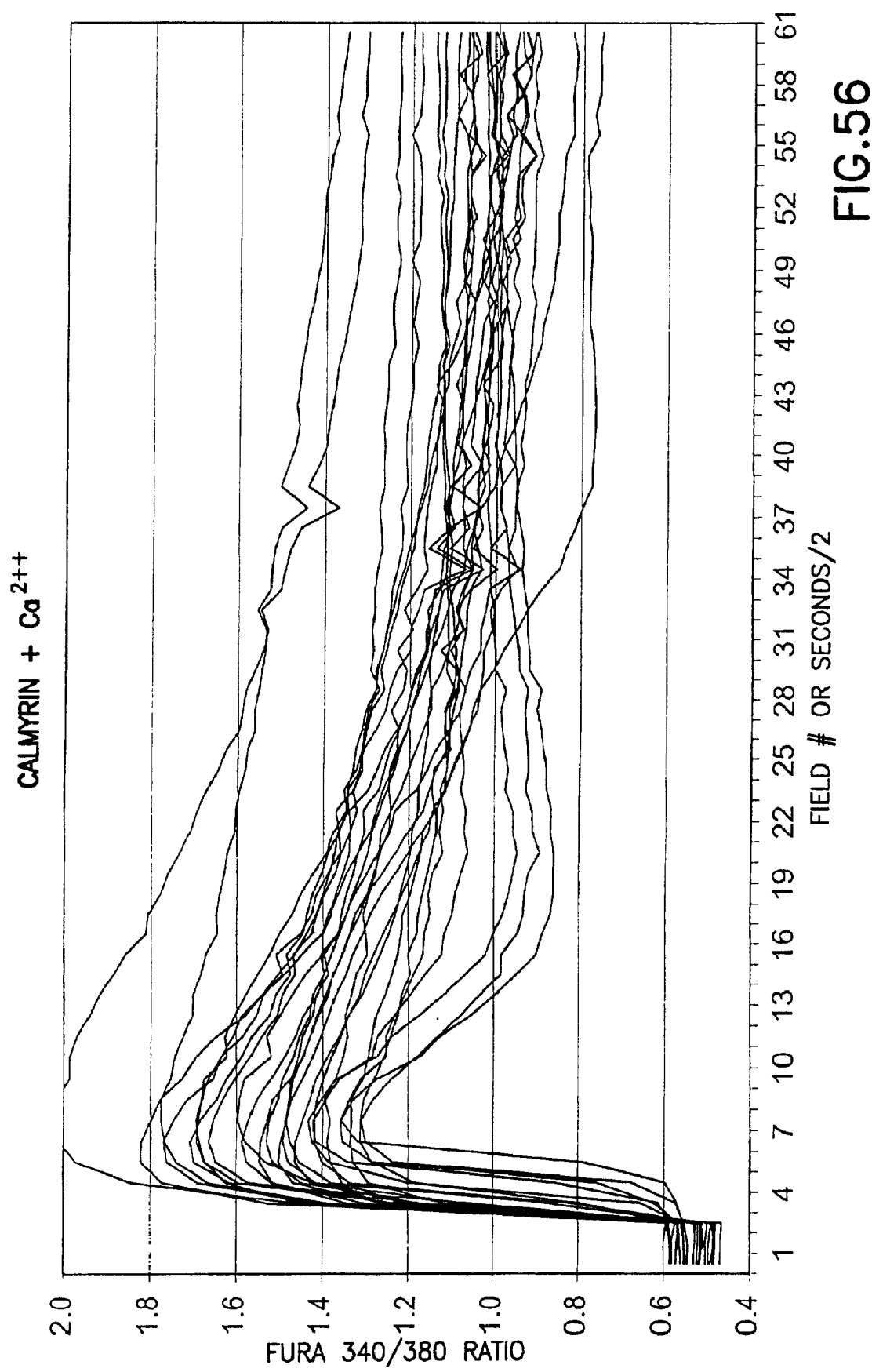
Figure 57:
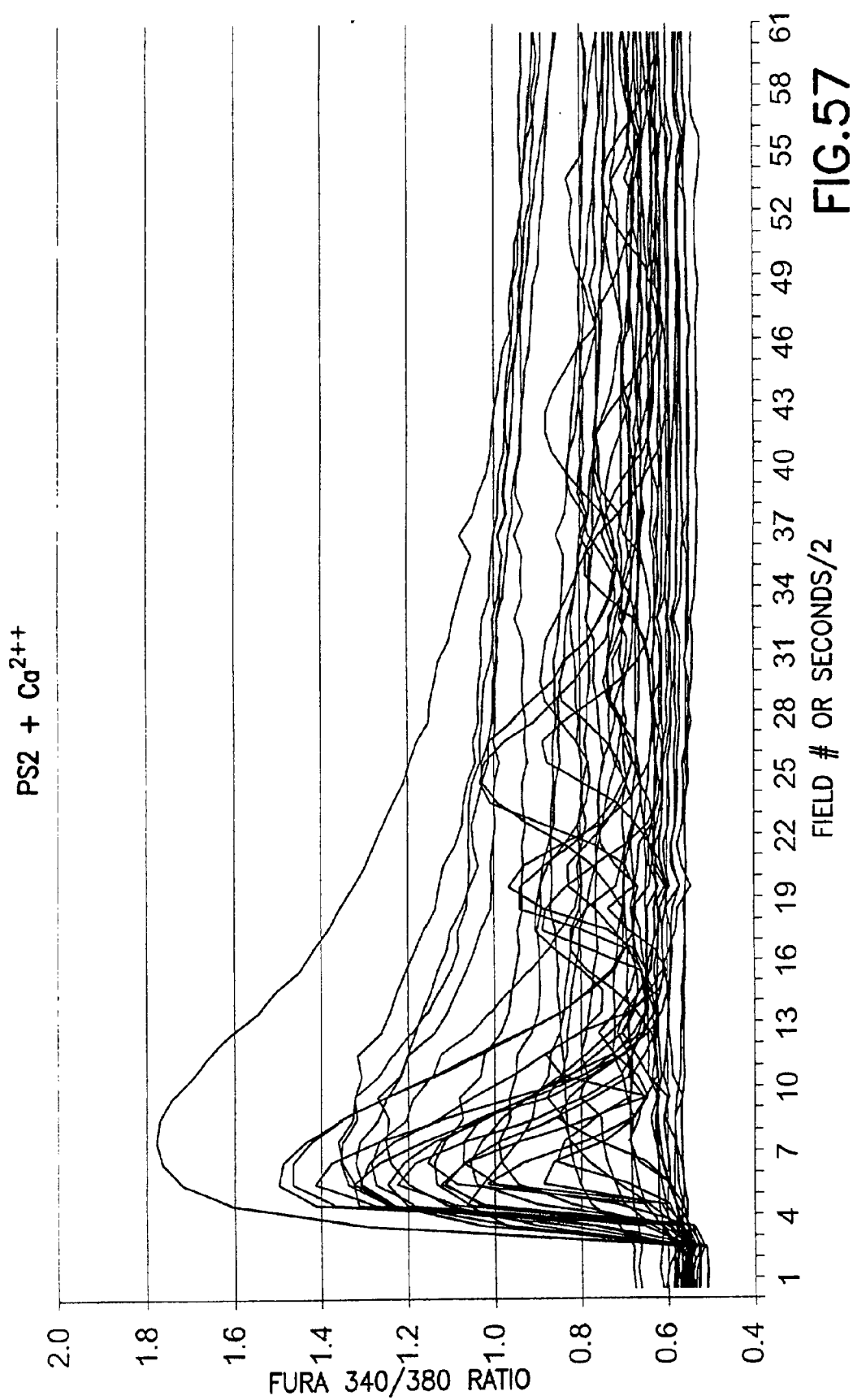
Figure 58:
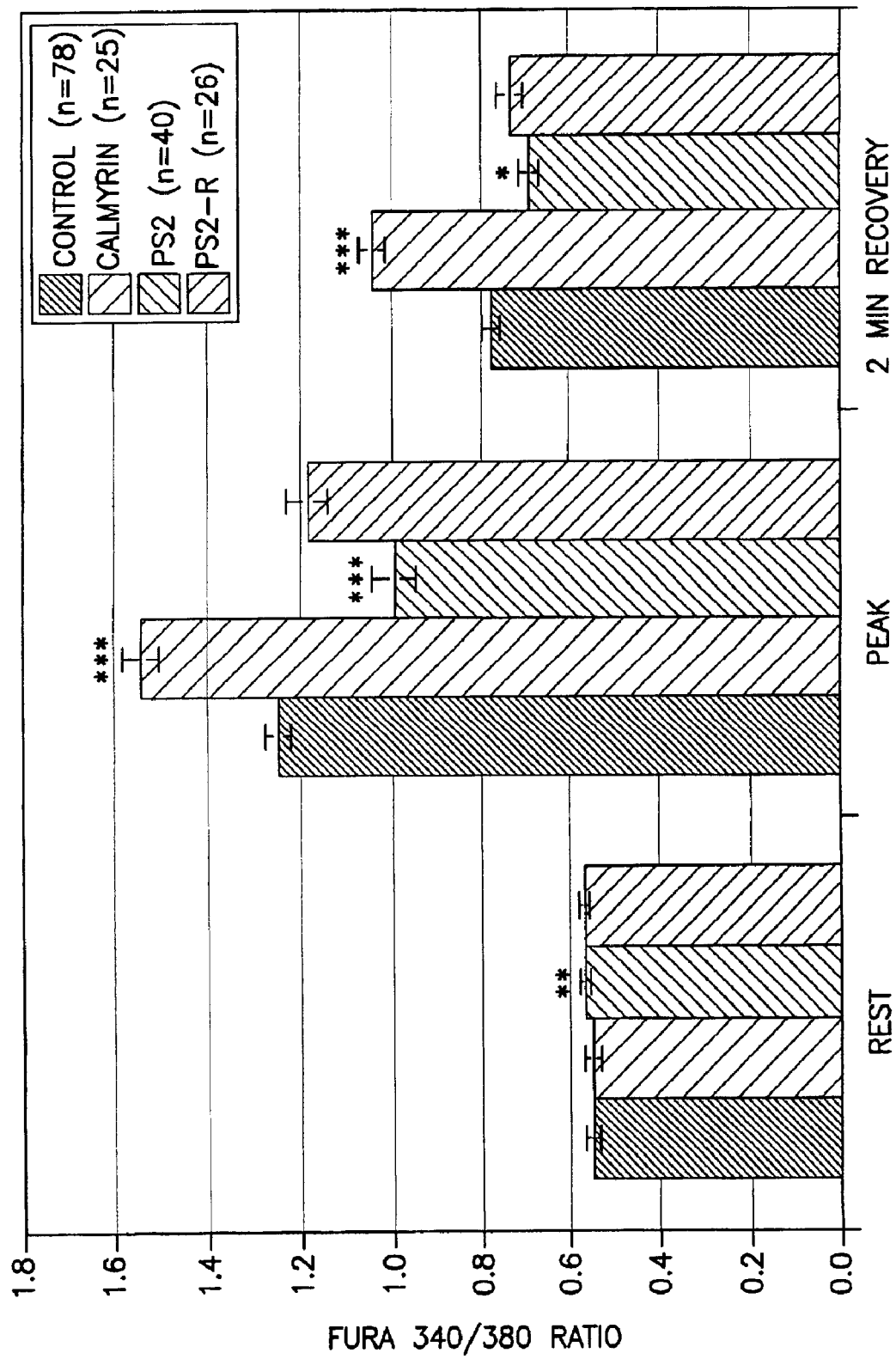
FIG. 58 is a graph showing resting, peak, and recovery $Ca^{2+}$ levels in calmyrin or PS2 overexpressing HeLa cells in $Ca^{2+}$ containing buffer.

All the histamine responses described previously were of cells incubated in buffer lacking $Ca^{2+}$. To determine how extracellular $Ca^{2+}$ affects these responses, calmyrin and PS2 overexpressing HeLa cells were also stimulated by 500 $\mu$M histamine in buffer that contained 1.8 mM $Ca^{2+}$. In control cells the presence of extracellular $Ca^{2+}$ did not affect the initial $Ca^{2+}$ release induced by histamine. However, the majority of these cells decreased their $Ca^{2+}$ levels more gradually then seen in $Ca^{2+}$ free buffer and far fewer cells displayed $Ca^{2+}$ oscillations (FIG. 55). This pattern suggests that these control HeLa cells may be somewhat "leaky" to $Ca^{2+}$ through plasma membrane channels. Even so, a difference in the cytosolic $Ca^{2+}$ pattern between controls and calmyrin expressers was still evident. For instance, in the controls all but 4 of 78 cells had returned below a fura ratio of 1.0 at one minute, whereas, only 4 of 25 calmyrin cells had recovered to that same 1.0 level by one minute (FIG. 55 and 56). As seen in FIG. 58, not only did the mean $Ca^{2+}$ level at 2 minutes remain significantly elevated above control (1.03 vs. 0.77, p-value<0.0001), but the mean peak of $Ca^{2+}$ release was also increased above control (1.55 vs. 1.24, p-value<0.0001) which is a difference not observed previously in the absence of $Ca^{2+}$. In the presence of extracellular $Ca^{2+}$, cells overexpressing PS2 showed highly variable responses similar to the patterns displayed in $Ca^{2+}$ free solution, and once again, about one third of the cells failed to respond to the addition of histamine (FIG. 57). As seen before, when $Ca^{2+}$ levels from only the responsive PS2 cells are averaged, the means are the same as for control cells (FIG. 58), thus it is likely that the non-responsive cells were high PS2 expressers while the control-like responding cells had low or no PS2 due to the inherent variation of expression levels with transient transfections.

Figure 59:
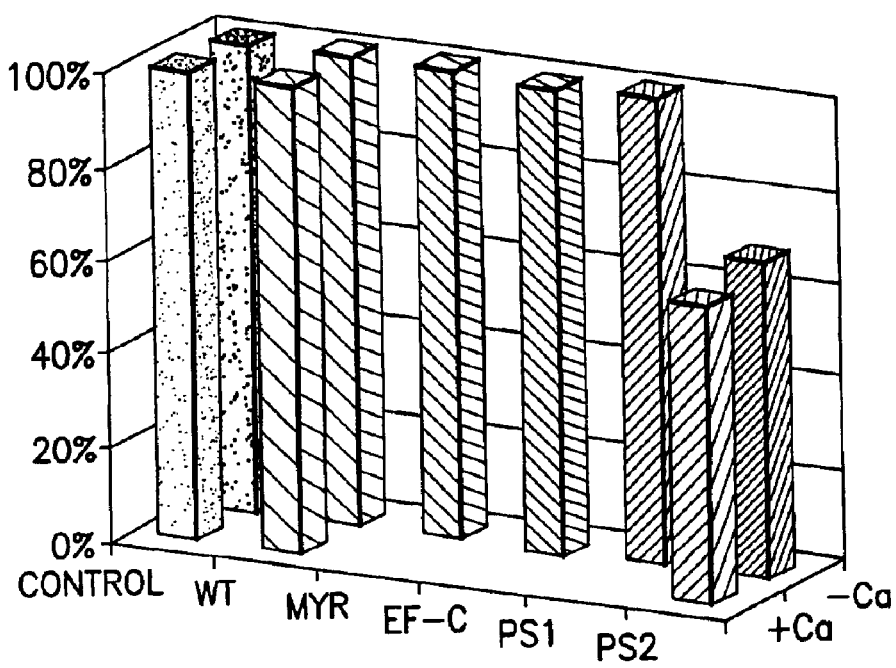
FIGS. 59–60 are bar graphs that summarize histamine induced $Ca^{2+}$ responses in HeLa cells expressing calmyrin and presenilin constructs with graph A showing the percentage of cells that responded to histamine and graph B showing the percentage of cells that oscillated in response to histamine.
Figure 60:
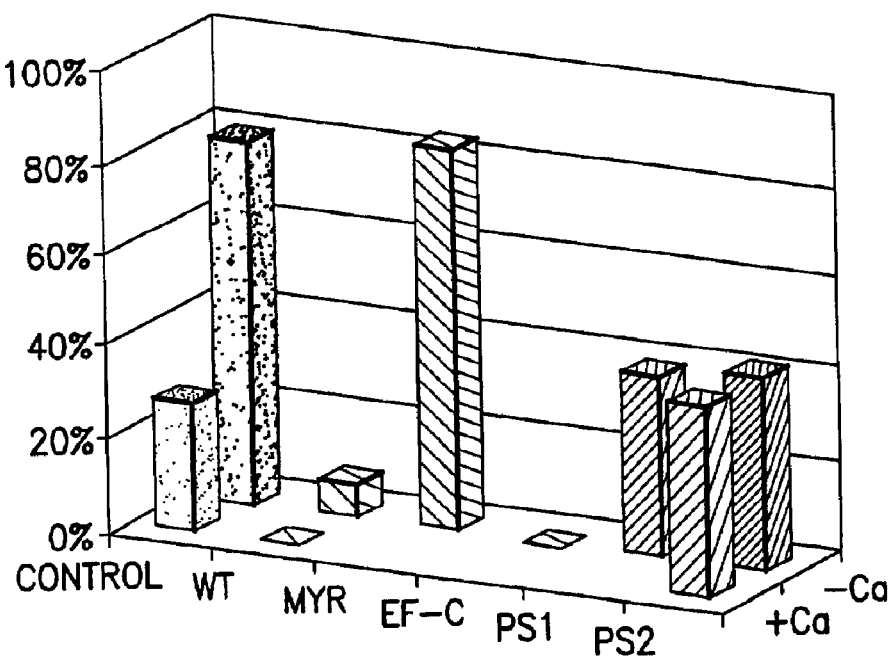

When considered in total, these results indicate that overexpressing calmyrin or the presenilins did not alter resting cytosolic $Ca^{2+}$ levels, but did perturb the regulation of histamine induced $Ca^{2+}$ release. To once more highlight the major effects, all the $Ca^{2+}$ imaging data was pooled and summarized in FIGS. 59–60. FIG. 59 demonstrates the notable and highly specific consequence of overexpressing PS2. Whereas, 100% of the HeLa cells expressing control, calmyrin or PS1 constructs released $Ca^{2+}$ in response to histamine, approximately one third of the PS2 cells (in both $Ca^{2+}$ free and $Ca^{2+}$ containing solutions) failed to release any $Ca^2$. Even though all the calmyrin cells released $Ca^{2+}$ in response to histamine, in the absence of $Ca^{2+}$ there was a striking and highly significant (p-value<0.00001) decrease in the oscillatory pattern that was common in control cells (FIG. 60). Also obvious in this graph are the similarity of the calmyrin-MYR mutant to the oscillatory control response and the similarity of the calmyrin-EF-C mutant to the non-oscillatory wild type calmyrin response. Thus, disrupting the myristoylation site on calmyrin prevented the protein from altering $Ca^{2+}$ regulation, whereas, mutating the $Ca^{2+}$-binding affinity nevertheless produced a wild type-like functional protein. Thus, it has been demonstrated that calmyrin binds to and colocalizes with PS2 and both of these proteins influence apoptosis and alter $Ca^{2+}$ response to histamine when overexpressed in HeLa cells. Accordingly, it is believed that the results of myristoylation and EF-hand mutants indicate that calmyrin and PS2 interact to trigger a signaling pathway leading to $Ca^{2+}$ release/recovery alterations and an ultimate end point of cell death. Furthermore, due to the numerous and varied proteins that interact with the presenilins and calmyrin, the presenilins may function to integrate a multitude of cellular signals, including but not limited to $Ca^{2+}$ signaling, to coordinate a "threshold" for programmed cell death.

Consistent with other reports (Janicki and Monteiro, 1997), overexpression of PS2 increased apoptosis in a dose-dependent manner. Likewise, as shown herein overexpressing calmyrin also increased apoptosis, however, mutating the myristoylation site or EF-hands significantly reduced this functional outcome. Unmyristoylated calmyrin inappropriately accumulates in the nucleus and fails to trigger apoptosis. The absence of the hydrophobic myristic acid may force calmyrin into an inactive conformation or it may simply decrease its ability to associate with the ER membrane with only minor structural consequences. If the latter case is true, it would indicate that targeting to the ER is essential for calmyrin's proapoptotic function. Localization to the ER is not a problem for the EF-C mutant, in fact it may even be enhanced, and aptly, apoptosis was induced. However, the level of apoptosis was noticeably less than that brought on by overexpressed wild type, even though the EF-C protein was expressed at slightly higher levels. This suggests that the putative reduction in affinity for $Ca^{2+}$ weakens calmyrin's ability to elicit apoptosis. While the EF-N mutant shows ER localization similar to EF-C, it produces an even smaller effect on apoptosis, which may be explained by its decreased stability (~50% of EF-C).

Coexpressing the calmyrin mutants with PS2 provided compelling evidence that these two proteins act in concert to signal cell death. Overexpressing both PS2 and calmyrin increases apoptosis additively. However, in contrast, overexpressing any of the three calmyrin mutants with PS2 partially or completely protected the cells from PS2 mediated apoptosis.

Considering the most extreme case of EF-C and PS2 first. At initial consideration it seemed surprising that two proteins that increase apoptosis individually, would fail to trigger apoptosis when coexpressed. This result implies that EF-C has a dominant-negative effect on PS2 function. To fully understand this finding it is important to remember that HeLa cells do expresses calmyrin endogenously, albeit at low levels. Therefore, the apoptosis generated by overexpressing PS2 individually, may actually have required PS2 to interact with endogenous calmyrin. And if so, overexpressing a functionally crippled calmyrin could compete with the much lower level endogenous protein, perhaps by retaining the ability to bind to PS2 (as seen with immunofluorescent staining, this mutant shows the appropriate subcellular localization to interact with PS2) yet being unable to transduce the cell death signal. It is difficult to imagine how the coexpression of two individually proapoptotic proteins could lead to only background levels of cell death, unless they directly interact in the same pathway. This explanation would also account for the EF-N data. Even though this mutation makes calmyrin less stable, the EF-N protein is still expressed at levels several times higher than the endogenous calmyrin allowing it to compete away the fully functional calmyrin. In contrast, overexpressing PS2 and the unmyristoylated (individually inactive) form of calmyrin produced a less dramatic effect on apoptosis, inducing levels that fall between PS2 alone and background. As this calmyrin mutant accumulates in the nucleus, it would be expected to compete less well for binding to the ER resident PS2, and thus, interfere only minimally with PS2 mediated apoptosis.

Thus, data shows convincing evidence that PS2 is involved in the apoptotic process and that calmyrin plays an active role in this presenilin function. Quantifying cell death measures an end point but it provides very little information about the original event or pathway that ultimately led to this most terminal of outcomes. Therefore, in an attempted to search more mechanistically upstream, the effect of calmyrin and PS2 on $Ca^{2+}$ signaling was also explored in view of the fact that calmyrin is a $Ca^{2+}$ binding protein and numerous studies had indicated that PS 1 mutations alter $Ca^{2+}$ signaling, yet only two published reports explored the role of PS2 in $Ca^{2+}$ regulation (Lessring et al., 1999; Yoo et al., 2000). To maintain consistency with localization and apoptosis findings, HeLa cells were also used for the $Ca^{2+}$ imaging studies. HeLa cells express plasma membrane histamine receptors that upon binding agonist signal via the $IP_3$ mediated pathway to release $Ca^{2+}$ from ER stores generating cytosolic $Ca^{2+}$ oscillations (Thorn, 1995). When calmyrin was overexpressed in HeLa cells, the $Ca^{2+}$ release pattern triggered by histamine was strikingly different. The most obvious difference being that after releasing a peak of $Ca^{2+}$, the cells overexpressing calmyrin maintained a plateau of cytosolic $Ca^{2+}$ above baseline and failed to oscillate. Furthermore, a small proportion of the calmyrin cells exhibited a delayed and more gradual rise in cytosolic $Ca^{2+}$ after stimulation with histamine. Even though the presented response curves and bar graphs convincingly demonstrate that overexpressing calmyrin alters histamine induced $Ca^{2+}$ signaling, the mechanistic origin of these alterations is less apparent.

Regardless of the exact mechanism involved, the $C^{2+}$ signaling patterns produced in cells overexpressing the various calmyrin mutants were particularly satisfying because they correlated with the apoptotic findings. Specifically, the nonmyristoylated calmyrin mutant that was compromised in inducing apoptosis, exhibited a $Ca^{2+}$ release pattern that was most similar to that of control HeLa cells. While the majority of MYR mutant cells oscillated in a manner similar to control cells, the peak of initial $Ca^{2+}$ release was significantly increased (above controls, wild type, and EF-C). This observation may imply that the ER stores contain higher levels of $Ca^{2+}$. On the other hand, the EF-C mutant, previously shown to be apoptotically competent, exhibited a $Ca^{2+}$ release pattern that was somewhat similar to that of wild type calmyrin. None of the transfected EF-C cells oscillated, and furthermore, a substantial proportion had slightly elevated levels of basal $Ca^{2+}$, which correlated with a reduction in the initial $Ca^{2+}$ release peak that was induced by histamine addition. As proposed earlier, these results may also suggest that localization of the overexpressed calmyrin protein (whether it be wild type or mutant) to the ER is essential for it to alter $Ca^{2+}$ signaling and increase apoptosis.

K. Method of Treatment

An important aspect of the biochemical studies using the genetic information of this invention is the development of therapies to circumvent or overcome the interaction of PS2 and calmyrin, and thus prevent, treat, control the deleterious effects of this interaction including apoptosis. Alzheimer's Disease manifests itself as a neurological disorder but such manifestation may be caused by the mutations affecting other organ tissues, such as the liver, releasing factors which affect brain activity and ultimately cause Alzheimer's Disease. Hence, in considering various therapies, it is understood that such therapies may be targeted at tissue other than the brain, such as heart, placenta, lung, liver, skeletal muscle, kidney and pancreas, where PS2 and calmyrin are also expressed.

The present invention provides a basis for therapeutic intervention in diseases which are caused by protein-protein interactions with presenilin 2. Therapies to treat presenilin-2 associated diseases such as AD may be based upon (1) gene therapy with mutant PS2 genes that encode a mutant protein that does not react with normal calmyrin, (2) gene therapy with mutant calmyrin genes that encode for mutant proteins that compete with wild-type calmyrin proteins, (3) gene therapy based upon sequences which encode a protein which blocks or corrects the deleterious effects of PS2, (4) immunotherapy based upon antibodies to normal calmyrin, or (5) small molecules (drugs) which block interactions between PS2 and calmyrin Protein Therapy treatment of presenilin-related Alzheimer's Disease, or other disorders resulting from protein-protein inaction between presenilin 2 and calmyrin, may be accomplished by replacing normal PS2 protein and/or calmyrin proteins with mutant non-binding proteins, by modulating the function of the normal protein, or by providing an excess of mutant PS2 or calmyrin protein to reduce the functional effect of the normal proteins. To replace the normal protein with a protein bearing a deliberate counterbalancing mutation it is necessary to obtain large amounts of pure PS2 or calmyrin protein from cultured cell systems which can express the protein. Delivery of the protein to the affected brain areas or other tissues can then be accomplished using appropriate packaging or administrating systems.

Gene therapy may also be employed in which mutant copies of a mutant PS2 gene or mutant calmyrin gene are introduced into patients to code successfully for mutant proteins in one or more different affected cell types. The gene must be delivered to those cells in a form in which it can be taken up and code for sufficient protein to provide effective function. Thus, it is preferred that the recombinant gene be operably joined to a strong promote so as to provide a high level of expression which will compensate for, or out-compete, the normal proteins. The recombinant construct may contain endogenous or exogenous regulatory elements, inducible or repressible regulatory elements, or tissue-specific regulatory elements.

In another series of embodiments, gene therapy may be used to introduce a recombinant construct encoding a protein or peptide which blocks the function of the presenilin 2 gene. In one embodiment, the recombinant gene may encode a peptide which corresponds to a favorable mutant domain of a presenilin 2 which has been found to reduce interaction with normal calmyrin. Thus, for example, if a mutant domain on presenilin 2 is found to reduce interaction with calmyrin, gene therapy may be employed to provide an excess of the mutant presenilin domain which may compete with the normal protein and inhibit or block the interaction with normal calmyrin.

Retroviral vectors can be used for somatic cell gene therapy especially because of their high efficiency of infection and stable integration and expression. The targeted cells however must be able to divide and the expression of the levels of normal protein should be high because the disease is a dominant one. The full length calmyrin or PS2 genes, subsequences encoding functional domains of the proteins, or any of the other therapeutic peptides described above, can be cloned into a retroviral vector and driven from its endogenous promoter, from the retroviral long terminal repeat, or from a promoter specific for the target cell type of interest (e.g., neurons). Other viral vectors which can be used include adeno-associated virus, vaccinia virus, bovine papilloma virus, or a herpes virus such as Epstein-Barr virus.

In another series of embodiments, antisense gene therapy may be employed. The antisense therapy is based on the fact that sequence-specific suppression of gene expression can be achieved by intracellular hybridization between mRNA or DNA and a complementary antisense species. The formation of a hybrid duplex may then interfere with the transcription of the gene and/or the processing, transport, translation and/or stability of the target calmyrin mRNA. Antisense strategies may use a variety of approaches including the administration of antisense oligonucleotides or antisense oligonucleotide analogs (e.g., analogs with phosphorothioate backbones) or transfection with antisense RNA expression vectors. Again, such vectors may include exogenous or endogenous regulatory regions, inducible or repressible regulatory elements, or tissue-specific regulatory elements.

Immunotherapy is also possible for Alzheimer's Disease. Antibodies may be raised to reactive sites on the calmyrin and/or PS2 protein (or a portion thereof) and administered to the patient to bind or block protein-protein interaction and reduce its deleterious effects. Simultaneously, expression of the mutant calmyrin protein product could be encouraged.

Antibodies to reactive sites or epitopes within the normal PS2 or calmyrin proteins can be raised to provide information on the characteristics of the proteins. Generation of antibodies enables the visualization of the protein in cells and tissues using Western blotting. In this technique, proteins are separated by polyacrylamide gel electrophoresis and transferred to nitrocellulose membranes. These membranes are then incubated in the presence of a primary antibody, washed and incubated with a secondary antibody to detect the protein-primary antibody complex. Following repeated washing, the entire complex is visualized using colourimetric or chemiluminescent methods.

In order to prepare polyclonal antibodies, fusion proteins containing defined portions or all of the PS2 or calmyrin proteins may be synthesized in bacteria by expression of corresponding DNA sequences in a suitable cloning vehicle, as described herein. The protein is then purified, coupled to a carrier protein, mixed with Freund's adjuvant (to help stimulate the antigenic response) and injected into rabbits or other suitable animals. Alternatively, protein can be isolated from cultured cells expressing the protein. Following booster injections at bi-weekly intervals, the rabbits or other suitable animals are bled and the sera isolated. Sera are used directly or purified prior to use, by various methods including affinity chromatography, Protein A-Sepharose, Antigen Sepharose, Anti-mouse-Ig-Sepharose. Further, antibodies may be obtained by making synthetic peptides corresponding to antigenic portions of the proteins and injecting these into rabbits or other suitable animals.

To produce monoclonal PS2 or calmyrin antibodies, cells actively expressing the protein are cultured or isolated from tissues and the cell membranes isolated. The membranes, extracts, or recombinant protein extracts containing the proteins are injected in Freund's adjuvant into mice. After receiving 9 injections over a three week period, the mice are sacrificed and their spleens are removed and resuspended in phosphate buffered saline (PBS). The spleen cells serve as a source of lymphocytes, some of which are producing antibody of the appropriate specificity. These cells are then fused with a permanently growing myeloma partner cell, and the products of the fusion are plated into a number of tissue culture wells in the presence of a selective agent such as HAT. The wells are screened by ELISA to identify those containing cells making useful antibody and these cells are freshly plated. After a period of growth, these cells are again screened to identify antibody-producing cells. Several cloning procedures are carried out until over 90% of the wells contain single clones which are positive for antibody production. By this procedure, a stable line of monoclonal antibody-producing clones is established. Monoclonal antibody produced by such clones is purified by methods such as affinity chromatography using Protein A Sepharose or ion-exchange chromatography or by variations and combinations of these techniques.

Antibodies may also be used coupled to other compounds or materials for diagnostic and/or therapeutic uses. For example, they may be coupled to radionuclides for imaging and therapy, or to liposomes for the targeting of compounds contained in the liposomes to a specific tissue location.

A further approach is to stimulate endogenous antibody production to the specific active regions of both wild-type presenilin 2 and calmyrin. For instance, reactive sites may included position 287, 288 and/or 297 of SEQ ID NO: 1 and positions within the calcium-binding EF-hands and/or in a penultimate N-terminal residue of SEQ ID NO: 2. Administration could be in the form of a one time immunogenic preparation or vaccine immunization. An immunogenic composition may be prepared as injectables, as liquid solutions or emulsions. The calmyrin protein or other antigen may be mixed with pharmaceutically acceptable excipients compatible with the protein. Such excipients may include water, saline, dextrose, glycerol, ethanol and combinations thereof. The immunogenic composition and vaccine may further contain auxiliary substances such as emulsifying agents or adjuvants to enhance effectiveness. Immunogenic compositions and vaccines may be administered parenterally by injection subcutaneously or intramuscularly. The immunogenic preparations and vaccines are administered in such amount as will be therapeutically effective, protective and immunogenic. Dosage depends on the route of administration and will vary according to the size of the host.

The PS2 and calmyrin DNA sequence can be altered using procedures such as restriction enzyme digestion, fill-in with DNA polymerase, deletion by exonuclease, extension by terminal deoxynucleotide transferase, ligation of synthetic or cloned DNA sequences and site-directed sequence alteration with the use of specific oligonucleotides together with PCR. The cDNA sequence or portions thereof, or a mini gene consisting of a cDNA with an intron and its own promoter, may be introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. Different promoters within vectors have different activities which alters the level of expression of the cDNA.

Some of the vectors listed contain selectable markers or neo bacterial genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene product is produced on a continuous basis.

Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors.

Using the techniques mentioned, the expression vectors containing the PS2 or calmyrin gene or portions thereof can be introduced into a variety of mammalian cells from other species or into non-mammalian cells. The recombinant expression vector, according to this invention, comprises the selected DNA of the DNA sequences of this invention for expression in a suitable host. The DNA is operatively joined in the vector to an expression control sequence in the recombinant DNA molecule so that the mutant PS2 or calmyrin protein can be expressed. The expression control sequence may be selected from the group consisting of sequences that control the expression of genes of prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

The host cells to be transfected with the vectors of this invention may be from a host selected from the group consisting of *E.coli, Pseudomonas, Bacillus subtillus, Bacillus stearothermophilus*, or other bacilli, other bacteria, yeasts, fungi, insects, mice or other animals or plant hosts or may be human tissue cells.

Treatment of Alzheimer's Disease can be performed by replacing the mutant protein with normal protein, or by modulating the function of the mutant protein. Once the biological pathway of the PS2 protein with calmyrin has been completely understood, it may also be possible to modify the pathophysiologic pathway or pathways (eg. a signal transduction pathway) in which these proteins participate, in order to correct the physiological defect.

Antisense based strategies can be employed to explore calmyrin gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target calmyrin mRNA. Hybridization is required for the antisense effect to occur, however the efficiency of intracellular hybridization is low and therefore the consequences of such an event may not be very successful. Antisense strategies may use a variety of approaches including the use of antisense oligonucleotides, injection of antisense RNA and transfection of antisense RNA expression vectors. Antisense effects can be induced by control (sense) sequences, however, the extent of phenotypic changes are highly variable. Phenotypic effects induced by antisense effects are based on changes in criteria such as protein levels, protein activity measurement, and target mRNA levels. Multidrug resistance is a useful model to study molecular events associated with phenotypic changes due to antisense effects, since the multidrug resistance phenotype can be established by expression of a single gene mdrl(MDR gene) encoding for P-glycoprotein.

It is further contemplated that a synthesized chain of nucleotides specific to code for a mutant presenilin 2 and or calmyrin may be used for immunization compositions. Recently, immunization techniques in which DNA constructs are introduced directly into mammalian tissue in vivo have been developed. Known as DNA vaccines, they use eukaryotic expression vectors to produce immunizing proteins in the vaccinated host. Methods of delivery include intramuscular and intradermal saline injections of DNA or gene gun bombardment of skin with DNA-coated gold beads. Mechanistically, gene gun-delivered DNA initiates responses by transfected or antigen-bearing epidermal Langerhans cells that move in lymph from bombarded skin to the draining lymph nodes. Following intramuscular injections, the functional DNA appears to move as free DNA through blood to the spleen where professional antigen presenting cells initiate responses. These methods are described inter alia in Robinson, *Sources in Immunology*, 9(5): 271–283, (1997 October) and Fynan et al, *Proc. Natl. Acad. Sci. USA.*, 90:11478–11482 (1993) and incorporated herein by reference.

References

All publications mentioned herein are incorporated herein by reference for all purposes.

Blacker, D., M. A. Wilcox, N. M. Laird, L. Rodes, S. M. Horvath, R. C. Go, R. Perry, B. J. Watson, 5.5. Bassett, M. G. McInnis, et al. 1998. Alpha-2 macroglobulin is genetically associated with Alzheimer disease. *Nat. Gene.* 19:357–360.

Buscigho, J., H. Hartmann, A. Lorenzo, C. Wong, K. Baumarn, B. Sommer, M. Staufenbiel, and B. A. Yanlcner. 1997. Neuronal localization of presenilin-1 and association with amyloid plaques and neurofibrillary tangles in AD. *J Neurosci.* 17:5101–5107.

Capell, A., R. Saffrich, J. C. Olivo, L. Meyn, J. Walter, J. Orunberg, P. Mathews, R. Nixon, C. Dotti, and C. Haass. 1997. Cellular expression and proteolytic processing of presenilin proteins is developmentally regulated during neuronal differentiation. *J Neurochem.* 69:2432–2440.

Caulin, C., G. S. Salvesen, and R. G. Oshima. 1997. Caspase cleavage of keratin 18 and reorganization of intermediate filaments during epithelial cell apoptosis. *J Cell Biol.* 138:1379–1394.

Corder, E. H., A. M. Saunders, W. J. Strittmatter, D. F. Schmechel, P. C. Gaskell, G. W. Small, A. D. Roses, J. L. Haines, and M. A. Pericak-Vance. 1993. Gene dose apolipoprotein E type 4 allele and the risk of AD in late onset families. *Science* 261:921–923.

Deng, G., C. J. Pike, and C. W. Cotman. 1996. Alzheimer-associated presenilin-2 confers increased sensitivity to apoptosis in PC12 cell. *FEBS Letts.* 397:50–54.

Dewji, N. N., C. Do, and S. J. Singer. 1997. On the spurious endoproteolytic processing of the presenilin proteins in cultured cells and tissues. *Proc. Natl Acad Sci.* 94:14031–14036.

Dewji, N. N., and S. J. Singer. 1997. Cell surface expression of the Alzheimer disease-related presenilin proteins. *Proc. Natl. Acad Sci. USA* 94:9926–9931.

Golemis, E., J. Gynris, and R. Brent. 1996. Interaction trap/two-hybrid system to identify interacting proteins. In Current Protocols in Molecular Biology, R. B. F. A. Ausubel, R. E. Kingston, D. D. Moore, J. G. Seidman, J. A. Smith, K, StruhI, ed. (New York: John Wiley & Sons), pp.20.1.1–20.1.28.

Guo, Q., K. Furukawa, B. L. Sopher, D. G. Pham, J. Xie, N. Robinson, G. M. Martin, and M. P. Mattson. 1996. Alzheimer's PS-1 mutation perturbs calcium homeostasis and sensitizes PC 12 cells to death induced by amyloid β peptide. *Neuroreport* 8:379–383.

Guo, Q., B. L. Sopher, K. Furukawa, D. G. Pham, N. Robinson, G. M. Martin, and M. P. Mattson. 1997. Alzheimer's presenilin mutation sensitizes neural cells to apoptosis induced by trophic factor withdrawal and amyloid beta-peptide: involvement of calcium and oxyradicals. *J Neurosci.* 17:4212–4222.

Guo, Q., N. Robinson, and M. Mattson. 1998. Secreted p-amyloid precursor protein counteracts the proapoptotic action of mutant presenilin-1 by activation of NF-κβ and stabilization of calcium homeostasis. *J Biol. Chem.* 273:12341–12351.

Guo, Q., S. Christakos, N. Robinson, and M. P. Mattson. 1998. Calbindin D28k blocks the proapoptotic actions of mutant presenilin 1: reduced oxidative stress and preserved mitochondrial function. *Proc. Natl. Acad Sci. USA* 95:3227–3232.

Haass, C. 1997. Presenilins: Genes for life and death. *Neuron* 18:687–690.

Hardy, J. 1997. Amyloid, the presenilins and Alzheimer's disease. *TINS* 20:155–159.

Janicki, S., and M. J. Monteiro. 1997. Increased apoptosis arising from increased expression of the Alzheimer's disease-associated presenilin-2 mutation (N1411). *J Cell Biol.* 139:485495.

Janicki, S., and M. J. Monteiro. 1999. Presenilin overexpression arrests cells in the Gi phase of the cell cycle: arrest potentiated by the Alzheimer's disease PS2 (N1411) mutant. *Am. J Pathol,* 155, 135–144.

Janicki, S. M., S. M. Stabler, and M. J. Monteiro. 2000. Familial Alzheimer's disease presenilin-1 mutants potentiate cell cycle arrest. *Neurobiol Aging.* 21:829–36.

Keller, J. N., Q. Guo, F. W. Holtsberg, A. J. Bruce-Keller, and M. P. Mattson. 1998. Increased sensitivity to mitochondrial toxin-induced apoptosis in neural cells expressing mutant presenilin-1 is linked to perturbed calcium homeostasis and enhanced oxyradical production. *J Neurosci.* 18:4439–4450. 3318.

Kim, T. W., W. R. Pettingell, Y. K. Jung, D. M. Kovacs, R E. Tanzi. 1997. Alternative cleavage of Alzheimer-associated presenilins during apoptosis by a caspase-3 family protease. *Science* 277:373–376.

Kobayashi, M., K. Takamatsu, S. Saitoh, and T. Noguchi. 1993. Myristoylation of hippocalcin is linked to it calcium-dependent membrane association properties. *J Biol. Chem.* 268(25):18898–18904.

Kovacs, D. M., H. J. Fausett, K. J. Page, T.-W. Kim, W. D. Moir, D. E. Merriam, R. D. Hollister, O. G. Hallmark, R. Mancini, K. M. Felsenstein, et al. 1996. Alzheimer-associated presenilins 1 and 2: neuronal expression in brain and localization to intracellular membranes in mammalian cells. *Nature Med* 2:224–229.

Lee, M. K., Z. Xu, P. C. Wong, and D. W. Cleveland. 1993. Neurofilaments are obligate heteropolymers in vivo. *J Cell Biol.* 122:1337–1350.

Leissring, M. A., B. A. Paul, 1. Parker, C. W. Cotman, and F. M. LaFerla. 1999. Alzheimer's presenilin-1 mutation potentiates inositol 1,4,5-trisphosphate-mediated calcium signaling in Xenopus ooctyes. *J Neurochem.* 72:1061–1068.

Leissring, M A, Parker, I, and LaFerla, F M, 1999. Presenilin-2 mutations modulate amplitude and kinetics of inositol 1,4,5-trisphosphate-mediated calcium signals. *J Biol. Chem,* 274, 32535–32538.

Li, J., M. Xu, H. Thou, J. Ma, and H. Potter. 1997. Alzheimer presenilins in the nuclear membrane, interphase kinetochores, and centrosomes suggest a role in chromosome segregation. *Cell* 90:917–927.

Loetscher, H., U. Deuschle, M. Broclchaus, D. Reinbardt, P. Nelboeck, J. Mous, J. Grunberg, C. Haass, H. Jacobsen. 1997. Presenilins are processed by caspase-type proteases. *J Biol. Chem.* 272(33):20655–20659.

Mical, T. I., and M. J. Monteiro. 1998. The role of sequences unique to nuclear intermediate filaments in the targeting and assembly of human lamin B: Evidence for lack of interaction of lamin B with its putative receptor. *J Cell Sci.* 111:3471–3485.

Monteiro, M. J., C. Hicks, L. Gu, and S. Janicki. 1994. Determinants for intracellular sorting of cytoplasmic and nuclear intermediate filaments. *J Cell Biol* 127:1327–1343.

Monteiro, M. J., and T. Mical. 1996. Resolution of kinase activities during the HeLa cell cycle: Identification of kinases with cyclic activities. *Exp. Cell Res.* 223:443451.

Montoya, S. F., C. F. Aston, S. T. DeKosky, M. Ilyas Kamboh, J. S. Lazo, and R E. Ferrell. 1998. Bleomycin hydrolase is associated with risk of sporadic Alzheimer's disease. *Nature Genet.* 18:211–212.

Naik, U. P., P. M. Patel, and L. V. Parise. 1997. Identification of a novel calcium-binding protein that interacts with the integrin alphaIIb cytoplasmic domain. *J Biol. Chem* 272:4651–4654.

Olshevskaya, E. V., R. E. Hughes, J. B. Hurley, and A. M. Dizhoor. 1997. Calcium binding, but not a calcium-myristoyl switch, controls the ability of guanylyl cyclase-activating protein GCAP-2 to regulate photoreceptor guanylyl cyclase. *J Biol. Chem.* 272:14327–14333.

Pack-Chung, E, Myers, M B, Pettingell, W P, Cheng, I, Moir, R D, Brownawell, A M, Tanzi, R E, and Kim, T-W, 2000. Presenilin 2 interacts with sorcin, a modulator of the ryanodine receptor. *J Biochem* 275:14440–14445.

Payami, H., G. D. Schellenberg, S. Zareparsi, J. Kaye, G. J. Sexton, M. A. Head, S. S. Matsuyama, L. F. Jarvik, B. Miller, D. Q. McManus et al. 1997. Evidence for association of HLA-A2 allele with onset age of Alzheimer's disease. *Neurology* 49, 512–518.

Pericak-Vance, M. A., M. P. Bass, L. H. Yammaoka, P. C. Gaskell, W. K. Scott, R. A. Terwedow, M. M. Menold, P. M. Conneally, G. W. Small, J. M. Vance, et al. 1997. Complete genomic screen in late-onset familial Alzheimer disease. Evidence for a new locus on chromosome 12. *JAMA* 278:1237–1241.

Peruz-Tur, J., S. Froelich, G. Prihar, R. Crook, M. Baker, K. Duff, M. Wragg, F. Busfield, C. Lendon, R. F. Clark et al. 1995. A mutation in Alzheimer's disease destroying a splice acceptor site in the presenilin-1 gene. *Neuroreport* 7:297–301.

Reynolds, A., and V. Lundblad. 1989. Yeast vectors and assays for expression of cloned genes. in Current Protocols in Molecular Biology, R. B. F. A. Ausubel, R. E. Kingston, D. D. Moore, J. G. Seidman, J. A. Smith, K, Struhi, ed. (New York: John Wiley & Sons), pp.13.6.1–13.6.4.

Stabler, Stacy M., Identification and Characterization of Calmyrin, a Presenilin 2 Interactor that Modulates Calcium Signaling and Apoptosis. PhD. Dissertation, April 2001.

Smine, A., X. Xu, K. Nishiyama, T. Katada, P. Gambetti, S. P. Yadav, X. Wu, Y. C. Shi, S. Yasuhara, V. Homburger, and T. Okamoto. 1998. Regulation of brain G-protein Go by Alzheimer's disease gene presenilin-1. *J Biol. Chem.* 273:16281–16288.

Thinakaran, G., D. R. Borchelt, M. K. Lee, H. H. Slunt, L. Spitaer, G. Kim, T. Ratovitsky, F. Davenport, C. Nordstedt, M. Seeger, et al. 1996. Endoproteolysis of presenilin 1 and accumulation of processed derivatives in vivo. *Neuron* 17:181 –190.

Vito, P., E. Lacana, and L. D. D'Adamio. 1996a. interfering with apoptosis: $Ca^{2+}$-binding protein ALG-2 and Alzheimer's disease gene ALG-3. *Science* 271:521–525.

Vito, P., B. Wolozin, J. K. Ganjei, K. Iwasaki, B. Lacana, and L. D. D'Adamio. 1996b. Requirement of the familial Alzheimer's disease gene P52 for apoptosis. *J Biol Chem.* 271:31025–31028.

Vito, P., et al. 1997. Generation of anti-apoptotic presenilin-2 polypeptides by alternative transcription, proteolysis, and caspase-3 cleavage. *J Biol. Chem.* 272:28315–28320.

Wilcox, C., J. S. Hu, and E. N. Olson. 1987. Acylation of proteins with myristic acid occurs cotranslationally. *Science* 238:1275–1278.

Wolozin, B., P. Alexander, and J. Palacino. 1998. Regulation of apoptosis by presenilin 1. *Neurobiol. Aging* 19: S23–S27.

Wolozin, B., K. Iwasaki, P. Vito, J. K Ganjei, B. Lacana, T. Sunderland, B. Zhao, J. W. Kusiak, Wasco, W., and L. D'Adamio. 1996. Participation of presenilin 2 in Apoptosis: enhanced basal activity conferred by an AD mutation. *Science* 274:1710–1713.

Woo, R. A., K. G. McLure, S. P. Lees-Miller, D. E. Rancourt, P. W. K. Lee. 1998. DNA-dependent protein kinase acts upstream of p53 in response to DNA damage. *Nature* 394:700–704.

Wu, J. M., Y. Chen, S. M, L. Perruccio, M. Adbel-Ghany, and T. H. Carter. 1993. Phosphorylation of protein tau by double-stranded DNA-dependent protein kinase. *Biochem. Biophys. Res. Commun.* 193(1):13–18.

Ye, Y., and M. E. Fortini. 1998. Characterization of Drosophila Presenilin and its colocalization with Notch during development. *Mech. Dev.* 79:199–21.

---

That which is claimed is:

1. A purified mutant calcium-binding protein consisting of a polypeptide comprising the amino acid sequence as set forth in SEQ ID NO: 2 conservatively substituted at acidic residue 127 or 172.

2. The purified mutant calcium-binding protein according to claim 1, wherein said substitution is the substitution of the acidic residue with its amine counterpart.

3. The purified mutant calcium-binding protein according to claim 2, wherein said substitution is at amino acid residue position 127.

4. The purified mutant calcium-binding protein according to claim 3, wherein said substitution is also at amino acid residue 172.

5. A purified mutant calcium-binding protein consisting of a polypeptide comprising the amino acid sequence as set forth in SEQ ID NO: 2 conservatively substituted at acidic residue 172 and wherein said acidic residue is replaced with its amine counterpart.

6. A purified mutant calcium-binding protein consisting of a polypeptide comprising the amino acid sequence as set forth in SEQ ID NO: 2 conservatively substituted at acidic residue 127 and wherein said acidic residue is replaced with its amine counterpart.

* * * * *